(12) United States Patent
Gaxiola et al.

(10) Patent No.: US 8,003,852 B2
(45) Date of Patent: *Aug. 23, 2011

(54) TRANSGENIC PLANTS OVEREXPRESSING A PLANT VACUOLAR PYROPHOSPHATASE

(75) Inventors: Roberto A. Gaxiola, Tempe, AZ (US); Gerald R. Fink, Chestnut Hill, MA (US); Seth L. Alper, Boston, MA (US)

(73) Assignees: University of Connecticut, Farmington, CT (US); Whitehead Institute for Biomedical Research, Cambridge, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/384,115

(22) Filed: Mar. 31, 2009

(65) Prior Publication Data

US 2009/0288222 A1  Nov. 19, 2009

Related U.S. Application Data

(63) Continuation of application No. 10/344,658, filed as application No. PCT/US01/09548 on Mar. 24, 2001, now Pat. No. 7,534,933.

(60) Provisional application No. 60/226,223, filed on Aug. 18, 2000, provisional application No. 60/164,808, filed on Nov. 10, 1999.

(51) Int. Cl.
*A01H 5/00* (2006.01)
*C12N 15/82* (2006.01)
*C12N 5/04* (2006.01)

(52) U.S. Cl. ........ 800/295; 800/298; 800/278; 800/289; 800/290; 435/419

(58) Field of Classification Search .......................... None
See application file for complete search history.

(56) References Cited

U.S. PATENT DOCUMENTS

| | | | |
|---|---|---|---|
| 4,707,359 A | 11/1987 | McMullen | |
| 4,945,050 A | 7/1990 | Sanford | |
| 5,071,962 A | 12/1991 | Morrison | |
| 5,100,792 A | 3/1992 | Sanford | |
| 5,294,593 A * | 3/1994 | Khan | 504/100 |
| 5,310,673 A | 5/1994 | Shibata | |
| 5,451,240 A | 9/1995 | Trowbridge | |
| 5,538,877 A * | 7/1996 | Lundquist et al. | 800/265 |
| 5,750,862 A | 5/1998 | John | |
| 5,837,545 A | 11/1998 | Guy et al. | |
| 5,859,338 A | 1/1999 | Meyerowitz | |
| 5,977,441 A | 11/1999 | Oliver | |
| 6,063,731 A | 5/2000 | Back | |
| 6,069,009 A | 5/2000 | Pepin | |
| 6,087,175 A | 7/2000 | John | |
| 6,087,176 A | 7/2000 | Durzan | |
| 6,198,026 B1 | 3/2001 | Fabijanski | |
| 6,200,808 B1 | 3/2001 | Simmonds | |
| 6,239,327 B1 | 5/2001 | Grossniklaus | |
| 6,248,935 B1 | 6/2001 | Cigan | |
| 6,255,564 B1 | 7/2001 | Fabijanski | |
| 6,936,750 B2 * | 8/2005 | Blumwald et al. | 800/298 |
| RE39,114 E | 5/2006 | Barry | |
| 7,041,875 B1 | 5/2006 | Blumwald | |
| 7,071,378 B1 | 7/2006 | Bonello | |
| 7,071,382 B2 | 7/2006 | Cahoon | |
| 7,534,933 B2 | 5/2009 | Gaxiola et al. | |
| 2002/0023282 A1 | 2/2002 | Gaxiola | |
| 2002/0178464 A1 | 11/2002 | Gaxiola et al. | |
| 2003/0213015 A1 | 11/2003 | Gaxiola | |
| 2005/0262598 A1 * | 11/2005 | Gaxiola et al. | 800/289 |
| 2005/0278808 A1 * | 12/2005 | Gaxiola et al. | 800/287 |
| 2008/0104733 A1 | 5/2008 | Gaxiola et al. | |

FOREIGN PATENT DOCUMENTS

| | | |
|---|---|---|
| WO | WO 97/26365 | 7/1997 |
| WO | WO 99/05902 | 2/1999 |
| WO | WO 99/47679 | 9/1999 |
| WO | WO 99/61616 | 12/1999 |
| WO | WO 00/75330 | 12/2000 |
| WO | WO 01/33945 | 5/2001 |
| WO | WO 01/45494 | 6/2001 |
| WO | WO 02/15674 | 2/2002 |
| WO | WO 02/16558 | 2/2002 |
| WO | WO 02/072849 | 9/2002 |
| WO | WO 2007/049275 | 5/2007 |
| WO | WO 2007/053974 | 5/2007 |
| WO | WO 2009/020528 A1 | 2/2009 |

OTHER PUBLICATIONS

Barkla et al. Physiology of ion transport across the tonoplast of higher plants. (1996) Annu. Rev. Plant Physiol. Plant Mol. Biol.; vol. 47, pp. 159-184.*

Rausch et al. Salt stress responses of higher plants: the role of proton pumps and Na+/H+-antiporters. (1996) J. Plant Physiol.; vol. 148, pp. 425-433.*

Kay et al. Duplication of CaMV 35S promoter sequences creates a strong enhancer for plant genes. (1987) Science; vol. 236, pp. 1299-1302.* Tanaka et al. Molecular cloning of cDNA for vacuolar membrane proton-translocating inorganic pyrophosphatase in *Hordeum vulgare*. (1993) Biochem. and Biophys. Res. Comm.; vol. 190; pp. 1110-1114.*

Drozdowicz et al. Vacuolar H+ pyrophosphatases: from the evolutionary backwaters into the mainstream. (2001) Trends in Plant Science; vol. 5; pp. 206-211.*

Abdullah, R., et al., "Efficient Plant Regeneration From Rice Protoplasts Through Somatic Embryogenesis,"*Bio/Technology*, 4:1087-1090 (1986).

Abel, S., et al., "Phosphate Sensing in Higher Plants," *Physiol. Plant.*, 115:1-8 (2002).

Al-Awqati, Q., "Chloride channels of intracellular organelles," *Current Opinion in Cell Biology 1995*, 7 :504-508.

Altschul, S.F., et al., "Gapped BLAST and PSI-BLAST: A New Generation of Protein Database Search Programs," *Nucleic Acids Research*, 25(17):3389-3402, (1997).

(Continued)

*Primary Examiner* — Cathy Kingdon Worley

(74) *Attorney, Agent, or Firm* — Hamilton, Brook, Smith & Reynolds, P.C.

(57) ABSTRACT

Transgenic plants are described which are engineered to overexpress vacuolar H+-PPase. Plants such as tobacco and petunia transformed with *A. Thaliana* AVP-1 are shown to have increased meristematic activity resulting in larger leaves, stem, flower, fruit, root structures, increased salt tolerance, enhanced drought and freeze tolerance. Methods of making such plants are also described.

13 Claims, 18 Drawing Sheets

OTHER PUBLICATIONS

Antebi, A. and Fink, G. R., "The Yeast $Ca^{2+}$-ATPase Homologue, PMR1, is Required for Normal Golgi Function and Localizes in a Novel Golgi-Like Distribution," *Mol. Biol. Cell*, 3:633-654, (1992).

Apse, M.P., et al., "Salt Tolerance Conferred by Overexpression of a Vacuolar Na+/H+ Antiport in *Arabidopsis*," *Science* 285: 1256-1258 (Aug. 20, 1999).

Arango, M., et al., "The Plasma Membrane Proton Pump ATPase: The Significance of Gene Subfamilies," *Planta*, 216:355-365 (2003).

Ballester, R., et al., "Genetic Analysis of Mammalian GAP Expressed in Yeast," *Cell*, 59:681-686, (1989).

Ballesteros, E., et al., "Na+/H+ antiport activity in tonoplast vesicles isolated from sunflower roots induced by NaCl stress," *Physiol. Plant.*, 99:328-334 (1997).

Baltscheffsky, M., et al., "$H^+$-Proton-Pumping Inorganic Pyrophosphatase: A Tightly Membrane-Bound Family," *FEBS Letters*, 452:121-127, (1999).

Barkla, B.J. and Pantoja, O., "Physiology of Ion Transport across the Tonoplast of Higher Plants," *Annu. Rev. Plant Physiol. Plant Mol. Biol.*, 47:159-184 (1996).

Barkla, B.J., et al., "The Plant Vacuolar $Na^+/H^+$ Antiport," *Symp. Soc. Exp. Biol.*, 48:141-153, (1994).

Barkla, B.J., et al., "Tonoplast $Na^+/H^+$ Antiport Activity and Its Energization by the Vacuolar $H^+$-ATPase in the Halophytic Plant Mesembryanthemum Crystallinum $L^1$," *Plant Physiol.*, 109:549-556, (1995).

Bassham, D.C. and Raikhel, N.V., "An Arabidopsis VPS45p Homolog Implicated in Protein Transport to the Vacuole," *Plant Physiol.*, 117:407-415, (1998).

Bechtold, N., et al., "In Planta Agrobacterium Mediated Gene Transfer by Infiltration of Adult Arabidopsis Plants," *C.R. Jances Acad. Sci. Ser. III Sci. Vie*, 361:1194-1199, (1993).

Becker, D., "Bynary Vectors Which Allow the Exchange of Plant Selectable Markers and Reporter Genes," *Nucleic Acids Research*, 18: pp. 203, (1990).

Bidonde, S., et al., "Expression and Characterization of Three Tomato 1-Aminocyclopropane-1-Carboxylate Oxidase cDNA in Yeast," *Eur. J. Biochem.*, 253:20-26, (1998).

Bouche-Pillon, et al., "Immunolocalization of the Plasma Membrane H+-ATPase in Minor Veins of *Vicia faba* in Relation to Phloem Loading," *Plant Physiol.*, 105:691-697 (1994).

Bremberger, C., et al., "Separation and purification of the tonoplast ATPase and pyrophosphatase from plants with constitutive and inducible Crassulacean acid metabolism", *Planta*, vol. 175, Springer-Verlag, pp. 465-470, 1988.

Brini, F., et al., "Cloning and Characterization of a Wheat Vacuolar Cation/Proton Antiporter and Pyrophosphatase Proton Pump," *Plant Physiology and Biochemistry*, 43(4): 347-354 (Apr. 2005).

Burbidge, A., et al., "Structure and expression of a cDNA encoding a putative neoxanthin cleavage enzyme (NCE), isolated from a wilt-related tomato (*Lycopersicon esculentum Mill.*) Library," *J. of Exp. Botany*, 47(317):2111-2112 (1997).

Cao, J., et al., "Regeneration of Herbicide Resistant Transgenic Rice Plant Following Microprojectilemediated Transformation of Suspension Culture Cells," *Plant Cell Rep.*, 11:589-591 (1992).

Carystinos, G.D., et al. "Vacuolar $H^+$-Translocating Pyrophosphatase Is Induced by Anoxia or Chilling in Seedlings of Rice$^1$ ," *Plant Physiol*, 108:641-649, (1995).

Clough, S.J. and Bent, A.F. "Floral Dip: A Simplified Method for Agrobacterium-Mediated Transformation of *Arabidopsis thaliana*," *Plant J.*, 16:735-743 (1998).

Counillon, L., et al., "A Point Mutation of the $Na^+/H^+$ Exchanger Gene (NHE1) and Amplification of the Mutated Allele confer Amiloride Resistance Upon Chronic Acidosis," *Proc. Natl. Acad. Sci. USA*, 90:4508-4512, (1993).

Cunningham, S.D., and Ow., D.W., "Promises and Prospects of Phytoremediation," *Plant Physiol.*, 110:715-719, (1996).

Darley, C.P., et al., "Chill-Induced Changes in the Activity and Abundance of the Vacuolar Proton-Pumping Pyrophosphatase From Mung Bean Hypocotyls," *Plant Physiol.*, 109:659-665, (1995).

Davies, J. M., "Vacuolar Energization: Pumps, Shunts and Stress," *Journal of Experimental Botany*, 48(308):633-641, (Mar. 1997).

Davies, J.M., "The Bioenergetics of Vacuolar H+ Pumps," In: Leigh RA, Sanders D (eds) The Plant Vacuole, 25:340-363. Academic Press, San Diego, (1997).

Drozdowicz, Y.M. and Rea, P.A., "Vacuolar H+-Pyrophosphatases: From Evolutionary Backwaters Into Mainstream," *Trends Plant Sci.*, 6(5):206-211 (2001).

Drozdowicz, Y.M., et al., "AVP2, a Sequence-Divergent, $K^+$ -Insensitive $H^+$-Translocating Inorganic Pyrophosphatase from *Arabidopsis*," *Plant Physiol.*, 123:353-362, (2000).

Estelle, M. and Somerville, C., "Auxin-Resistant Mutants of *Arabidopsis thaliana* with an Altered Morphology," *Mol. Gen. Genet.*, 206:200-206 (1987).

Farré, E. M., et al., "Accceleration of Potato Tuber Sprouting by the Expression of a Bacterial Pyrophosphatase," *Nature Biotechnology*, 19: 268-272 (2001).

Fink, G., et al., "Increased Size, Salt and Drought Tolerance in *A. thaliana* Overexpressing AVP1 Vacuolar H+-Pyrophosphatase," *Plant Biology*, (Jul. 2001)[online]. Retrieved from the Internet: URL: <http://abstracts.aspb.org/pub2001/public/P32/0206.html>.

Gahoonia, T.S. and Nielsen, N.E., "Root Traits as Tools for Creating Phosphorus Efficient Crop Varieties," *Plant Soil*, 260:47-57 (2004).

Galway, et al., "Growth and Ultrastructure of *Arabidopsis* Root Hairs: The rhd3 Mutation Alters Vacuole Enlargement and Tip Growth," *Planta*, 201:209-218, (1997).

Gaxiola, et al., "Drought-and-Salt-Tolerant Plants result From Overexpression of the AVP1 $H^+$-Pump," *PNAS*, 98(20):11444-11449 (Sep. 2001).

Gaxiola, R., et al., "A Novel and Conserved Salt-Induced Protein is an Important Determinant of Salt Tolerance in Yeast," *EMBO J.* 11(9):3157-3164 (Sep. 1992).

Gaxiola, R., et al., "Ectopic Overexpression in Tomato of the *Arabidopsis* AVP1 Gene Results in Drought Tolerance," *Plant Biology*, (Jul. 2003) [online]. Retrieved from the Internet: URL: <http//abstracts.aspb.org/pb2003/public/P33/0948.html>.

Gaxiola, R.A., et al., "Plant Proton Pumps," *FEBS Lett.*, 581:2204-2214 (2007).

Gaxiola, R.A., et al., "The *Arabidosis thaliana* Proton Transporters, AtNhx1 and Avp1, Can Function in Cation Detoxification in Yeast," *Proc. Natl. Acad. Sci. USA* 96:1480-1485 (Feb. 1999).

Gaxiola, R.A., et al., "The Yeast CLC Chloride Channel Functions in Cation Homeostasis," *Proc. Natl. Acad. Sci. USA* 95(7):4046-4050 (Mar. 1998).

Gibeaut, D.M., et al., "Maximal Biomass of *Arabidopsis thaliana* Using a Simple, Low-Maintenance Hydroponic Method and Favorable Environmental Conditions," *Plant Physiol*. 115:317-319 (1997).

Gietz, D., et al., "Improved Method for high Efficiency Transformation of Intact Yeast Cells," *Nucl. Acids Res.*, 20:p. 1425, (1992).

Gillooly, J.F., et al., "The Metabolic Basis of Whole-Organism RNA and Phosphorus Content," *Proc. Natl. Acad. Sci. USA*, 102(33):11923-11927 (2005).

Gogarten, et al. "The Use of Antisence mRNA to Inhibit the Tonoplast $H^+$ ATPase in Carrot," *The Plant Cell*, 4:851-864, (1992).

Guiltinan, M.J. and McHenry, L., "Epitope Tagging for the Detection of Fusion Protein Expression in Transfenic Plants," *Methods Cell Biol.*, 49:143-151, (1995).

Guo, H.H., et al., "Protein Tolerance to Random Amino Acid Change," *PNAS*, 101(25):9205-9210, (2004).

Gupta, et al. "Maintenance of Photosynthesis at Low Leaf Water Potential in Wheat,", *Plant Physiol.*, 89:1358-1365, (1989).

Hajdukiewicz, Z., et al. "The Small, Versatile *pPZP* Family of *Agrobacterium* Binary Vectors for Plant Transformation," *Plant Molecular Biology*, 25:989-994, (1994).

Hammond, J.P., et al., "Genetic Responses to Phosphorus Deficiency," *Ann. Bot.*, 94:323-332 (2004).

Hartel, H., et al., "DGD1-Independent Biosynthesis of Extraplastidic Galactolipids After Phosphate Deprivation in *Arabidopsis?*," *Proc. Natl. Acad. Sci. USA*, 97(19):10649-10654 (2000).

Haughn, G.W. and Somerville, C., "Sulfonylurea-resistant Mutants of *Arabidopsis thaliana*," *Mol Gen Genet*, 204: 430-434 (1986).

Hechenberger, M., et al., "A Family of Putative Chloride Channels from *Arabidopsis* and Functional Complementation of a Yeast with a *CLC* Gene Disruption," *J. Biol. Chem.* 271(52):33632-33638 (Dec. 27, 1996).

Hermans, C., et al., "How Do Plants Respond to Nutrient Shortage by Biomass Allocation?," *Trends Plant Sci.*, 11(12):610-617 (2006).

Hill, M.A. and Preiss J., "Functional Analysis of Conserved Histidines in ADP-Glucose Pyrophosphorylase from *Escherichia coli*," *Biochemical and Biophysical Research Communications*, 244:573-577, (1998).

Hirschi, et al., "CAxl, an $H^+/Ca^{2+}$ Antiport From *Arabidopsis*," *Proc. Natl. Acad. Sci. USA*, 93:8782-8786, (1996).

Holford, I.C.R., "Soil Phosphorus: Its Measurements and Its Uptake by Plants," *Aust. J. Soil Res.*, 35:227-239 (1997).

Hong, B., et al., "Identification of a Calmodulin-Regulated $Ca^{2+}$-ATPase in Endoplasmic Reticulm," *Plant Physiology*, 119:1165-1175 (1999).

International Search Report, PCT/US2008/009091, Mail date: Oct. 30, 2008, pp. 5.

Jauh, G.Y., et al., "Tonoplast Intrinsic Protein Isoforms as Markers for Vacuolar Functions," *The Plant Cell*, 11:1867-1882, (1999).

Kausch, A.P., et al., "Effects of Microprojectile Bombardment on Embryogenic Suspension Cell Cultures of Maize (*Zea mays* L.) Used for Genetic Transformation," *Planta*, 196:501-509 (1995).

Kay, R., et al., "Duplication of CaMV 35S Promoter Sequences Creates a Strong Enhancer for Plant Genes," *Science*, 236:1299-1302 (1987).

Kennedy, B.K., et al., "Redistribution of Silencing Proteins From Telomeres to the Nucleolus Is Associated With Extension of Life Span in *S. cerevisiae*," *Cell*, 89:381-391, (1997).

Kieber, J.J., et al., "CTR1, a Negative Regulator of the Ethylene Response Pathway in *Arabidopsis*, Encodes a Member of the Rat Family of Protein Kinases," *Cell*, 72:427-441, (1993).

Kim, E.J., et al., "Heterologous expression of plant vacuolar pyrophosphatase in yeast demonstrates sufficiency of the substrate-binding subunit for proton transport," *Proc. Natl. Acad. Sci. USA*, 91:6128-6132 (1994).

Kim, Y., et al., "Isolation and Characterization of cDNAs Encoding the Vacuolar H+-Pyrophosphatase of *Beta vulgaris*," *Plant Physiol.*, 106:375-382 (1994).

Kirsch, M., et al., "Salt stress induces an increased expression of V-type H+ -ATPase in mature sugar beet leaves," *Plant Mol. Biol.*, 32:543-547 (1996).

Kochian, L., et al., "How Do Crop Plants Tolerate Acid Soils? Mechanisms of Aluminium Tolerance and Phosphorus Efficiency," *Annu. Rev. Plant Biol.*, 55:459-493 (2004).

Krysan, P.J., et al., "Identification of Transferred DNA Insertions Within *Arabidopsis* Genes Involved in Signal Transduction and Ion Transport," *Proc. Natl. Acad. Sci. USA*, 93:8145-8150, (1996).

Lazar, E., et al., "Transforming Growth Factor α: Mutation of Aspartic Acid 47 and Leucine 48 Results in Different Biological Activities," *Molecular and Cellular Biology*, 8(3):1247-1252, (1988).

Leigh, "Solute Composition of Vacuoles," *Advances in Botanical Research, The Plant Vacuole*, 25:171-194, (1997).

Lerchl, J., et al., "Molecular cloning, characterization and expression analysis of isoforms encoding tonoplast-bound proton-translocating inorganic pyrophosphatase in tobacco," *Plant Mol. Biol.*, 29:833-840 (1995).

Levi, M., et al., "Rapid Immunofluorescent Determination of Cells in the S Phase in Pea Root Meristems: An Alternative to Autoradiography," *Physiologic Plantarum*, 71: 68-72, (1987).

Li, J., et al., "*Arabidopsis* H+-PPase AVP1 Regulates Auxin-Mediated Organ Development," *Science*, 310:121-125, (2005).

Lopez-Bucio, et al., "Phosphate Availability Alters Architecture and Causes Changes in Hormone Sensitivity in the *Arabidopsis* Root System," *Plant Physiol.*, 129:244-256 (2002).

Madhani, H.D., et al., "MAP Kinases with Distinct Inhibitory Functions Impart Signaling Specificity During Yeast Differentiation," *Cell*, 91:673-684, (1997).

Madrid, R., et al., "Ectopic Potassium Uptake in trk1 trk2 Mutants of *Saccharomyces cerevisiae* Correlates With a Highly Hyperpolarized Membrane Potential," *The Journal of Biological Chemistry*, 272(24):14838-14844, (1998).

Maeshima, M., "Vacuolar H+-Pyrophosphatase,"*Biochimica et Biophysica Acta*, 1465:37-51 (2000).

Marty, F., "The Biogenesis of Vacuoles: Insights from Microscopy," In: Leight RA, Sanders D (eds) The Plant Vacuole, pp. 1-42. Academic Press, San Diego, (1997).

McCormick, S., "Transformation of tomato with *Agrobacterium tumerfaciens*," In: Lindsey, K. (ed) Plant Tissue Culture Manual, pp. 1-9. Kluwer Academic Publishers, Dordrecht, The Netherlands, (1991).

McCusker, J.H. et al., "Pleiotropic Plasma Membrane ATPase Mutations of *Saccharomyces cerevisiae*,"*Molecular and Cellular Biology*, 7(11):4082-4088, (1987).

McSteen, P. and Leyser, O., "Shoot Branching," *Annu. Rev. Plant Biol.*, 56:353-374 (2005).

Meyerowitz, E.M., et al., "In Situ Hybridization to RNA in Plant Tissue," *Plant Molec. Biol. Rep.*, 5:242-250, (1987).

Misson, J., et al., "A Genome-Wide Transcriptional Analysis Using *Arabidopsis thaliana* Affymetrix Gene Chips Determined Plant Responses to Phosphate Deprivation," *PNAS*, 102(33):11934-11939 (2005).

Mitsuda, N., et al., "Pollen-Specific Regulation of Vacuolar H+-PPase Expression by Multiple *cis*-Acting Elements," *Plant Molecular Biology*, 46: 185-192 (2001).

Muchhal, U.S., et al., "Phosphate Transporters From the Higher Plant *Arabidopsis thaliana*," *Proc. Natl. Acad. Sci. USA*, 93:10519-10523 (1996).

Mullen, R.T., et al., "Identification of the Peroxisomal Targeting Signal for Cottonseed Catalase," *The Plant Journal*, 12(2):313-322, (1997).

Murashige, T. and Skoog, F., "A Revised Medium for Rapid Growth and Bioassays With Tobacco Tissue Culture," *Physiol. Plant.*, 15:473-497 (1962).

Murguia, J.R., et al., "A Salt-Sensitive 3'('),5'-Bisphosphate Nucleotidase Involved in Sulfate Activation," *Science*, 267:232-234, (1995).

Murphy, A., Eisinger, et al., "Early Copper-Induced Leakage of K+ From *Arabidopsis* Seedlings Is Mediated by Ion Channels and Coupled to Citrate Efflux," *Plant Physiol.*, 121:1375-1382 (1999).

Murphy, J. and Riley, J.P., "A Modified Single Solution Method for the Determination of Phosphate in Natural Waters," *Anal. Chim. Acta*, 27:31-36 (1962).

Nakamura, Yoshiyuki, et al., "Stimulation of the Extrusion of Protons and H+-ATPase Activities with the Decline in Pyrophosphatase Activity of the Tonoplast in Intact Mung Bean Roots under High-NaCl Stress and Its Relation to External Levels of $Ca^{2+}$ Ions", *Plant Cell Physiol.*, vol. 33, No. 2, JSPP, pp. 139-149, 1992.

Nass, R., et al., "Intracellular Sequestration of Sodium by a Novel $Na^+/H^+$ Exchanger in Yeast Is Enhanced by Mutations in the Plasma Membrane H+-ATPase," *The Journal of Biological Chemistry*, 272(42):26145-26152, (Oct. 17, 1997).

Nass, R., et al., "Novel Localization of a Na+/H+ Exchanger in a Late Endosomal Compartment of Yeast," *J. Biol. Chem.* 273(33):21054-21060 (Aug. 14, 1998).

Neuhaus, J-M, and Rogers, J.C., "Sorting of proteins to vacuoles in plant cells," *Plant Mol. Biol.*, 38:127-144 (1998).

Niyogi, K.K. and Fink, G.R., "Two Anthranilate Synthase Genes in *Arabidopsis*: Defense-Related Regulation of the Tryptophan Pathway," *The Plant Cell*, 4:721-733, (1992).

Paris, N., et al., "Molecular Cloning and Further Characterization of a Probable Plant Vacuolar Sorting Receptor," *Plant Physiol.*, 115:29-39 (1997).

Park, S., et al., "Up-Regulation of a H+-Pyrophosphatase (H+-PPase) as a Strategy to Engineer Drought-Resistant Crop Plants," *PNAS 102* (52): 18830-18835 (2005).

Quesada, A., et al., "PCR-Identification of a Nicotiana Plymbaginifolia cDNA Homologous to the High-Affinity Nitrate Transporters of the crnA Family," *Plant Molecular Biology*, 34:265-274, (1997).

Raghothama, K.G., "Phosphate Acquisition," *Annu. Rev. Plant Physiol. Plant Mol. Biol.*, 50:665-693 (1999).

Randall, S.K. and Sze, H., "Properties of the Partially Purified Tonoplast H+-Pumping ATPase From Oat Roots," *The Journal of Biological Chemistry*, 261(3):1364-1371, (1986).

Rate, D.N., et al., "The Gain-of-Function *Arabidopsis* acd6 Mutant Reveals Novel Regulation and Function of the Salicylic Acid Signaling Pathway in Controlling Cell Death, Defenses, and Cell Growth," *The Plant Cell*, 11:1695-1708, (1999).

Rausch, et al., Salt Stress Responses of Higher Plants: The Role of Proton Pumps and Na/H+-Antiporters, *Plant Physiol.*, 148:425-433, (Jan. 1996).

Rea, P.A. and Turner, J.C., "Tonoplast Adenosine Triphosphatase and Inorganic Pyrophosphatase," *Method in Plant Biochemistry*, 3:385-405, (1997).

Rea, P.A., et al., "Vacuolar H(+)-Translocating Pyrophosphatases: A New Category of Ion Translocase," *Trends Biochem. Sci.*, 17:348-353 (1992).

Rodriguez-Navarro, A. and Ramos, J., "Dual System for Potassium Transport in *Saccharomyces cerevisiae*," *Journal of Bacteriology*, 159(3):940-945, (1984).

Sanchez-Calderon, L., et al., "Characterization of Low Phosphorus Insensitive Mutants Reveals a Crosstalk Between Low Phosphorus-Induced Determinate Root Development and Activation of Genes Involved in the Adaptation of *Arabidopsis* to Phosphorus Deficiency," *Plant Physiol.*, 140:879-889 (2006).

Sandler, S.J., et al., "Inhibition of Gene Expression in Transformed Plants by Antisense RNA," *Plant Molecular Biology*, 11(3):301-310, (1988).

Sarafian, V., et al., "Molecular cloning and sequence of cDNA encoding the pyrophosphate-energized vacuolar membrane proton pump of *Arabidopsis thaliana*," *Proc. Natl. Acad. Sci. USA*, 89:1775-1779 (Mar. 1, 1992).

Sarafian, V., et al., "Radiation-Inactivation Analysis of Vacuolar Proton Atpase and Proton Pyrophosphatase From Beta-Vulgaris L. Functional sizes for Substrate Hydrolysis and for Proton Transport," *Biochemical Journal*, 283(2): 493-497 (1992).

Sato, M.H., et al., "The *AtVAM3* Encodes a Syntaxin-Related Molecule Implicated in the Vacuolar Assembly in *Arabidopsis thaliana*," *J. Biol. Chem.* 272(39):24530-24535 (Sep. 26, 1997).

Schiefelbein, et al., Pollen Tube and Root-Hair Tip Growth is Disrupted in a Mutant of *Arabidopsis thaliana*, *Plant Physiol.*, 103:979-985, (1993).

Schneider, B.L., et al., "Use of Polymerase Chain Reaction Epitope Tagging for Protein Tagging in *Saccharomyces cerevisiae*," *Yeast*, 11(13):1265-1274, (1995).

Schumaker, K. S. and Sze, H., "A $Ca^{2+}/H^+$ Anitport System Driven by the Proton Electrochemical Gradient of a Tonoplast $H^+$-ATPase From Oat Roots," *Plant Physiol.*, 79: 1111-1117 (1985).

Schwappach, B., et al., "Golgi Localization and Functionally Important Domains in the $NH_2$ and COOH Terminus of the Yeast CLC Putative Chloride Channel Geflp," *J. of Biol. Chem.*, 273(24):15110-15118 (1996).

Serrano, R., and Gaxiola, R., "Microbial Models and Salt Stress Tolerance in Plants," *Critical Reviews in Plant Sciences*, 13(2):121-138 (1994).

Shen, H., et al., "Root Plasma Membrane H+-Atpase Is Involved in the Adaptation of Soybean to Phosphorus Starvation," *J. Exp. Bot.*, 57(6):1353-1362 (2006).

Sheveleva, E., et al., "Increased Salt and Drought Tolerance by D-Ononitol Production in Transgenic *Nicotiana tabacum L.,*" *Plant Physiol.*, 115:1211-1219, (1997).

Smart, L.B., et al., "Genes Involved in Osmoregulation During Turgor-Driven Cell Expansion of Developing Cotton Fibers Are Differentially Regulated," *Plant Physiol.*, 116:1539-1549 (1998).

Sorin, A., et al., "PMR1, a $Ca^{2+}$-AtPase in Yeast Golgi, Has Properties Distinct From Sarco/Endoplasmic Reticulum and Plasma Membrane Calcium Pumps," *The Journal of Biological Chemistry*, 272(15):9895-9901, (1997).

Stitt, M., "Pyrophosphate as an Energy Donor in the Cytosol of Plant Cells: an Enigmatic Alternative to ATP," *Bot. Acta 111*:167-175 (1998).

Sugita, K., et al., "A Transformation Vector for the Production of Marker-Free Transgenic Plants Containing a Single Copy Transgene at High Frequency," *Plant Journal*, 22(5): 461-469 (2000).

Sze, et al. "Energization of Plant Cell Membranes by $H^+$-Pumping ATPases: Regulation and Biosynthesis,", *The Plant Cell*, 11:677-689, (Apr. 1999).

Tanaka, Y., et al., "Molecular Cloning of cDNA for Vacuolar Membrane Proton-Translocating Inorganic Pyrophosphatase in Hordeum Vulgare," *Biochem & Biophys. Res. Comm.*, 190(3):1110-1114 (1993).

Topfer, R., et al., "A Set of Plant Expression Vectors for Transcriptional and Translational Fusions," *Nucleic Acid Res. 15*(14):5890 (Jul. 24, 1987).

Tsiantis, M.S., et al., "Salt regulation of transcript levels for the c subunit of a leaf vacuolar H+-ATPase in the halphyte *Mesembryanthemum crystallinum*," *The Plant Journal*, 9(5):729-736 (1996).

van der Krol, A.R., et al., "Inhibition of Flower Pigmentation by Antisense CHS Genes: Promoter and Minimal Sequence Requirements for the Antisense Effect," *Plant Mol. Biol.* 14:457-466 (Apr. 1990).

Vance, C.P., et al., "Phosphorus Acquisition and Use: Critical Adaptations by Plants for Securing a Nonrenewable Resource," *New Phytologist*, 157:423-447 (2003).

Vitale, A., and Raikhel, N.V., "What do proteins need to reach different vacuoles?," *Trends in Plant Science*, 4:148-154 (1999).

Ward, J., et al., "Dissociation and Reassembly of the Vacuolar H+-ATPase Complex From Oat Roots," *Plant Physiol.*, 99:161-169 (1992).

Wu, S.J., et al., "SOS1, A Genetic Locus Essential for Salt Tolerance and Potassium Acquisition," *The Plant Cell*, 8:617-627, (1996).

Xiang, C., et al., "A Mini Binary Vector Series for Plant Transformation," *Plant Mol. Biol.*, 40:711-717 (1999).

Xie, X.S., et al., "Isolation and Reconstruction of the Chloride Transporter of Clathrin-Coated Vesicles," *J. Biol. Chem. 264*(32): 18870-18873 (Nov. 1989).

Yan, F., et al., "Adaptation of H+-Pumping and Plasma Membrane H+ ATPase Activity in Proteoid Roots of White Lupin Under Phosphate Deficiency," *Plant Physiol.*, 129:50-63 (2002).

Zemo, D.A. and McCabem, J.T., "Transcriptional Responses of the Rat Vasopressin Gene to Acute and Repeated Acute Osmotic Stress," *Neuroscience Research*, 44:45-50, (2002).

Zhang, J., et al., "Improving Drought Tolerance in Medicago Truncatula Via Translational Genomics," *Plant Biology*, (Jul. 2007)[online]. Retrieved from the Internet: URL: <http://abstracts.aspb.org/pb2007/public/P09/P09019.html>.

Zhen, R.G., et al., "Acidic Residues Necessary for Pyrophosphate-Energized Pumping and Inhibition of the Vacuolar H+-pyrophosphatase by N,N'-Dicyclohexylcarbodiimide," *J. Biol. Chem. 272*(35):22340-22348 (Aug. 29, 1997).

Zhen, R.G., et al., "Aminomethylenediphosphonate: A Potent Type=Specific Inhibitor of Both Plant and Phototrophic Bacterial $H^+$-Pyrophosphatases," *Plant Physiol.*, 104:153-159, (1994).

Zhen, R.G., et al., "Localization of Cytosolically Oriented Maleimide-Reactive Domain of Vacuolar $H^+$-Pyrophosphatase," *The Journal of Biological Chemistry*, 269(37):23342-23350, (1994).

Zhen, R.G., et al., "The Molecular and Biochemical Basis of Pyrophosphate-Energized Proton Translocation at the Vacuolar Membrane," *Advances in Botanical Research, The Plant Vacuole*, 25:298-337, (1997).

Zhu, Y., et al., "A Link Between Citrate and Proton Release by Proteoid Roots of White Lupin (*Lupinus albus* L.) Grown Under Phosphorus-Deficient Conditions," *Plant Cell Physiol.*, 46(6):892-901 (2005).

International Preliminary Report on Patentability, PCT/US2008/009091, issued Feb. 9, 2010.

Hung, S. et al., "Vacuolar H+-pyrophosphatase cDNA (Accession No. U31467) from Etiolated Mung Bean Seedlings (1)," *Plant Physiol.* 109:1125 (1995) Retrieved from the internet May 13, 2008, http://www.ebi.ac.uk/~textman/pgr-htdocs/pgr/PGR95-085.html.

Ikeda, M. et al., "A Vacuolar H+-pyrophosphatase in *Acetabularia acetabulum*: Molecular Cloning and Comparison with Higher Plants and a Bacterium," *Journal of Experimental Botany*, 50(330):139-140 (1999).

Maruyama, C. et al., "Structural Studies of the Vacuolar H+-Pyrophosphatase: Sequence Analysis and Identification of the Residues Modified by Fluorescent Cyclohexylcarbodiimide and Maleimide," *Plant Cell Physiol.* 39(10):1045-1053 (1998).

Nakanishi, Y. and Maeshima, M., "Molecular Cloning of Vacuolar H+-Pyrophosphatase and Its Developmental Expression in Growing Hypocotyl of Mung Bean," *Plant Physiol.* 116:589-597 (1998).

Nakanishi, Y. et al., "Molecular Cloning and Sequencing of the cDNA for Vacuolar H+-pyrophosphatase from *Chara coralline*," *Biochimica et Biophysica Acta* 1418:245-250 (1999).

Sakakibara, Y. et al., "Identification of the Gene Structure and Promoter Region of H+-translocating Inorganic Pyrophosphatase in Rice (*Oryza sativa* L.)," *Biochimica et Biophysica Acta* 1444:117-124 (1999).

Sakakibara, Y. et al., "Isolation and Characterization of cDNAs Encoding Vacuolar H+-pyrophosphatase Isoforms from Rice (*Oryza sativa* L.)," *Plant Molecular Biology* 31:1029-1038 (1996).

Suzuki, Y. et al., "Molecular Cloning of Vacuolar H+-pyrophosphatase and Its Expression during the Development of Pear Fruit," *Plant Cell Physiol.* 40(8):900-904 (1999).

Yelenosky, G. and Guy, C.L., "Freezing Tolerance of Citrus, Spinach, and Petunia Leaf Tissue," *Plant Physiol.* 89:444-451 (1989).

International Preliminary Report on Patentability, International Application No. PCT/US2008/009091, Dated: Feb. 9, 2010.

Office Action, U.S. Appl. No. 11/135,165, Dated: Oct. 31, 2006.
Office Action, U.S. Appl. No. 11/135,165, Dated: Jul. 25, 2007.
Office Action, U.S. Appl. No. 11/135,165, Dated: Jun. 6, 2008.
Office Action, U.S. Appl. No. 11/135,165, Dated: Oct. 22, 2009.
Office Action Made Final, U.S. Appl. No. 11/135,165, Dated: Aug. 2, 2010.
Office Action Made Final, U.S. Appl. No. 11/119,683, Dated: Mar. 16, 2010.
Office Action, U.S. Appl. No. 11/119,683, Dated: Sep. 17, 2009.
Office Action, U.S. Appl. No. 11/119,683, Dated: Jul. 18, 2008.
Office Action, U.S. Appl. No. 11/119,683, Dated: Nov. 30, 2007.
Office Action Made Final, U.S. Appl. No. 11/119,683, Dated: Jul. 10, 2007.
Office Action, U.S. Appl. No. 11/119,683, Dated: Oct. 5, 2006.
Office Action Made Final, U.S. Appl. No. 11/890,795, Dated: May 26, 2010.
Office Action, U.S. Appl. No. 11/890,795, Dated: Oct. 13, 2009.
Office Action Made Final, U.S. Appl. No. 11/890,795, Dated: Apr. 29, 2009.
Office Action, U.S. Appl. No. 11/890,795, Dated: Sep. 15, 2008.
Office Action, Canada Application No. 2,418,127, Dated: Mar. 10, 2009.
Office Action, Canada Application No. 2,390,719, Dated: Mar. 10, 2009.
Office Action, Canada Application No. 2,419,901, Dated: Mar. 16, 2009.
Office Action, Canada Application No. 2,390,719, Dated: Nov. 12, 2010.
Office Action, Canada Application No. 2,418,127, Dated: Nov. 12, 2010.
Office Action, Canada Application No. 2,419,901, Dated: Nov. 18, 2010.
Notice of Abandonment, U.S. Appl. No. 09/934,088, Dated: Jul. 27, 2005.
Office Action, U.S. Appl. No. 09/934,088, Dated: Jul. 27, 2005.
Office Action, U.S. Appl. No. 09/934,088, Dated: Dec. 22, 2004.
Office Action, U.S. Appl. No. 09/934,088, Dated: Sep. 24, 2003.
Office Action, U.S. Appl. No. 11/119,683, Dated: Apr. 11, 2011.
Office Action—Pre Appeal Conf. Decision, U.S. Appl. No. 11/119,683, Dated: Sep. 16, 2010.
Office Action—Pre Appeal Conf. Decision, U.S. Appl. No. 11/119,683, Dated: Mar. 4, 2009.
Notice of Allowance, U.S. Appl. No. 10/344,658, Dated: Jan. 16, 2009.
Office Action—Advisory Action, U.S. Appl. No. 10/344,658, Dated: Dec. 9, 2008.
Office Action—Interview Summary, U.S. Appl. No. 10/344,658, Dated: Oct. 27, 2008.
Office Action, U.S. Appl. No. 10/344,658, Dated: Sep. 18, 2008.
Examiner-Initiated Interview Summary—Office Action, U.S. Appl. No. 10/344,658, Dated: Mar. 18, 2008.
Office Action Made Final, U.S. Appl. No. 10/344,658, Dated: Mar. 10, 2008.
Office Action, U.S. Appl. No. 10/344,658, Dated: Aug. 6, 2007.
Office Action, U.S. Appl. No. 10/344,658, Dated: Nov. 14, 2006.
Interview Summary—Office Action, U.S. Appl. No. 10/344,658, Dated: Aug. 1, 2006.
Office Action Made Final, U.S. Appl. No. 10/344,658, Dated: May 17, 2006.
Office Action, U.S. Appl. No. 10/344,658, Dated: Nov. 3, 2005.
Office Action—Notice of Panel Decision from Pre-Appeal Brief Review, U.S. Appl. No. 11/890,795, Dated: Mar. 28, 2011.
Office Action, U.S. Appl. No. 11/135,165, Dated: Feb. 28, 2011.

\* cited by examiner

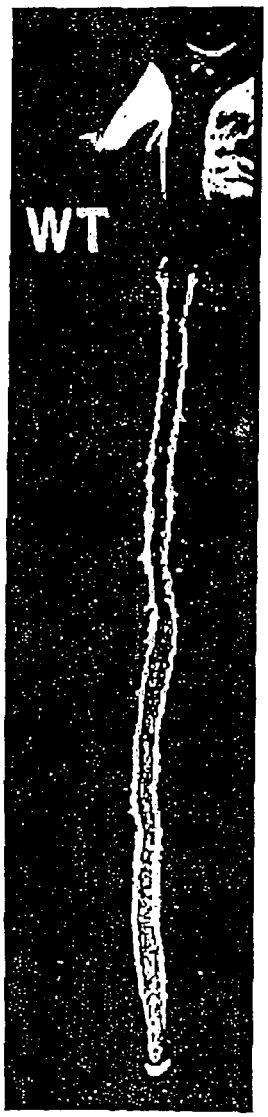  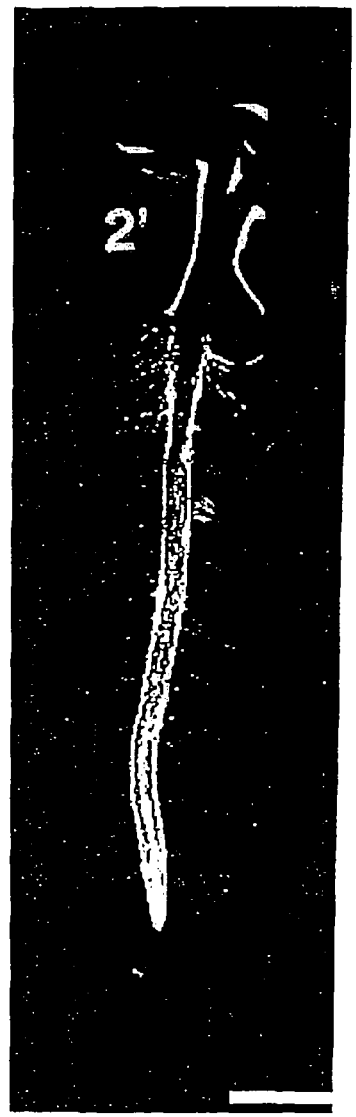
FIG. 1B(1)   FIG. 1B(2)   FIG. 1B(3)

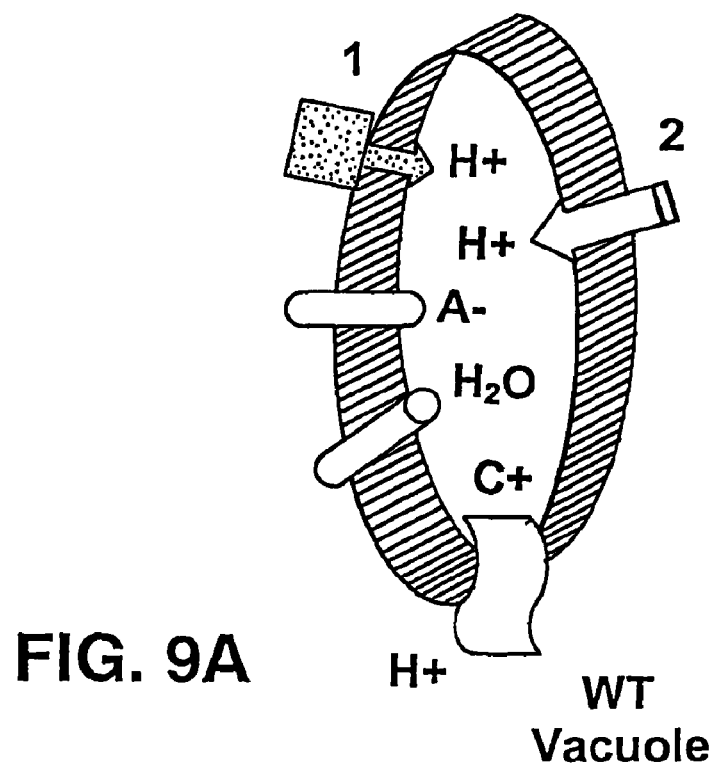
FIG. 9A  WT Vacuole
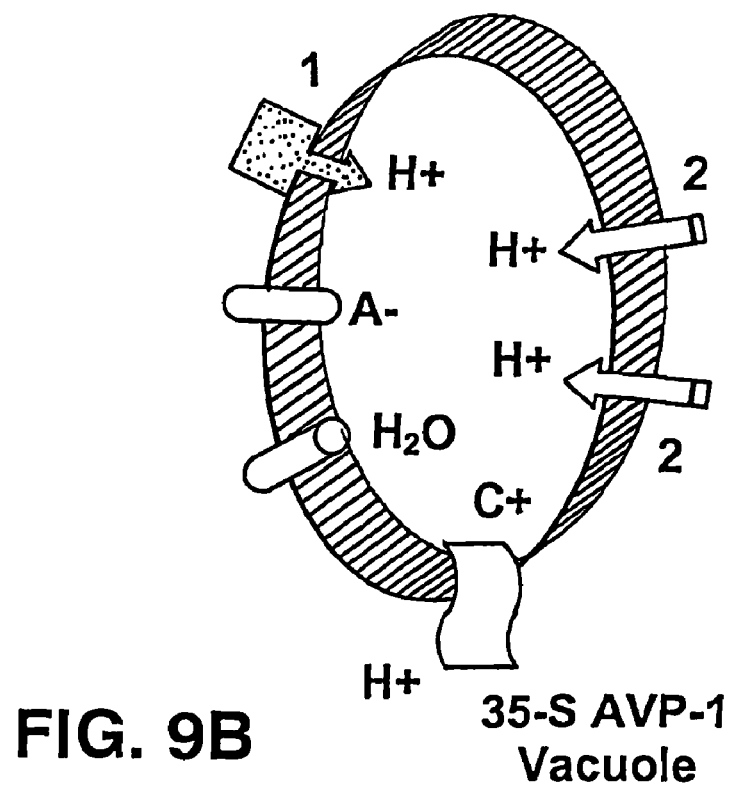
FIG. 9B  35-S AVP-1 Vacuole

_US 8,003,852 B2_

TRANSGENIC PLANTS OVEREXPRESSING A PLANT VACUOLAR PYROPHOSPHATASE

RELATED APPLICATIONS

This application is a Continuation of U.S. application Ser. No. 10/344,658, filed Feb. 13, 2003, now U.S. Pat. No. 7,534,933, which is the U.S. National Stage application of International Application No. PCT/US01/09548, filed on Mar. 24, 2001, published in English, which claims priority to PCT/US00/30955, filed Nov. 10, 2000, which claims priority to U.S. application Ser. No. 09/644,039, filed on Aug. 22, 2000 (now abandoned), which claims the benefit of 60/226,223, filed Aug. 18, 2000, and 60/164,808, filed Nov. 10, 1999.

The entire teachings of the above applications are incorporated herein by reference.

GOVERNMENT SUPPORT

The invention described herein was supported, in whole or in part, by Grants GM52414, DK54214, DK43495, DK51509, DK34854 and GM35010 from the National Institutes of Health and by Grant MCB9317175 from the National Science Foundation. The Government has certain rights in the invention.

BACKGROUND OF THE INVENTION

1. Field of the Invention

The present invention relates to genetically-altered plants that are hardy with respect to environmental stresses, such as drought and/or freezing, oversized with respect to vegetative and/or sexual structure (as compared to their normal phenotypic counterparts), and capable of growing in media of high salinity. Such plants also display high meristematic activity, and increased in cellular division activity.

2. Background of the Related Art

The prospects for feeding humanity as we enter the new millennium are formidable. Given the every increasing world population, it remains a major goal of agricultural research to improve crop yield. It also is a major goal of horticultural research to develop non-crop plants which are hardier, such as ornamental plants, grasses, shrubs, and other plants found useful or pleasing to man.

Until recently crop and horticultural improvements depended on selective breeding of plants having desirable characteristics. Such selective breeding techniques, however, were often less than desirable as many plants have within them heterogenous genetic complements that do not result in identical desirable traits of their parents.

Advances in molecular biology have allowed mankind to manipulate the germplasm of animals and plants. Genetic engineering of plants entails the isolation and manipulation of genetic material (typically in the form of DNA or RNA) and the subsequent introduction of that genetic material into a plant. Such technology, has led to the development of plants with increased pest resistance, plants that are capable of expressing pharmaceuticals and other chemicals, and plants that express beneficial traits. Advantageously such plants not only contain a gene of interest, but remain fertile.

One area of interest of late in plant sciences has been the development of plants with improved stress resistance. In general, plants possess and maintain adaptive mechanisms to ensure survival during periods of adverse environmental conditions. Two commons stresses that plants commonly encounter are freezing and drought, both of which are associated with cellular dehydration. It is known that certain plants contain genes turned on by exposure to cold or prolonged periods of dehydration that encode for products that are directly or indirectly responsible for providing greater resistance to drought and/or freeze than many of their counterparts. A number of genes responsive to heat and water stress have now been characterized (See, e.g., U.S. Pat. Nos. 5,837,545, 5,071,962, 4,707,359). These genes are believed by many to produce certain proteins, such as "Water Stress Proteins", that are postulated to aid the plants survival. For example, certain plants exposed to stress conditions produce a hormone called abcisic acid (ABA) which helps plants close their stromata, thereby reducing the severity of the stress. Unfortunately, ABA is known to inhibit the formation of new leaves, to cause flowers and fruit to drop off, and to lead to a reduction in yield.

Most tropical plants are not believed to have evolved the ability to tolerate prolonged drought and/or freezing. Conversely, many temperate plants are known to have developed at least some ability to tolerate such conditions. The productivity of plant varieties in dry conditions, and after freeze, differ dramatically. For example, tobacco (_Nicotiana_ spp.) produces fresh leaves that are highly sensitive to drought, and cannot be produced commercially in areas with a limited water supply and high degree of evaporation. In contrast to water stress, very little is known about proteins and genes which participate in freezing tolerance. However, it has been hypothesized that a major component of freeze tolerance may involve tolerance to dehydration (See, e.g., Yelenosky, G. C., Guy, L. (1989) Plant Physiol. 89: 444-451).

Another particular area of interest of late has been the development of plants with improved abilities to grow in salinized soil. Salinization of soil occurs when water supplies contain dissolved salt. Upon evaporation of water from such supplies, salts gradually accumulate in the soil. The progressive salinization of irrigated land compromises the future of agriculture in many of the most productive areas of our planet (Serrano, R., et al., _Crit. Rev. Plant Sci._, 13:121-138 (1994)). For example, arid regions offer optimal photoperiod and temperature conditions for the growth of most crops, but suboptimal rainfall. Artificial irrigation has solved the problem only in the short term as it has been found that soils in such environments frequently are rapidly salinized. To grow in salinized environments, plants must maintain a much lower ratio of $Na^+/K^+$ in their cytoplasm than that present in the soil, preventing the growth of a number of plants, including food crops.

Physiological studies suggest that salt exclusion in the root, and/or salt sequestration in the leaf cell vacuoles, are critical determinants for salt tolerance (Kirsch, M., et al., _Plant Mol. Biol._, 32:543-547 (1996)). Toxic concentrations of sodium chloride (NaCl) build up first in the fully expanded leaves where NaCl is compartmentalized in the vacuoles. Only after their loading capacity is surpassed, do the cytosolic and apoplasmic concentrations reach toxic levels, ultimately leading to loss of turgor, ergo plant death. It has been suggested that hyperacidification of the vacuolar lumen via the V-ATPase provides extra protons required for a $Na^+/H^+$ exchange-activity leading to the detoxification of the cytosol (Tsiantis, M. S., et al., _Plant J._, 9:729-736 (1996)). Salt stress is known to increase both ATP- and pyrophosphate (PPi)-dependent $H^+$ transport in tonoplast vesicles of, for example, sunflower seedling roots. Salt treatments also induce an amiloride-sensitive $Na^+/H^+$ exchange activity (Ballesteros, E., et al., _Physiologia Plantarum_, 99:328-334 (1997)). In the halophyte _Mesembryanthemum crystallinum_, high NaCl stimulates the activities of both the vacuolar $H^+$-ATPase (V-ATPase) and a vacuolar $Na^+/H^+$ antiporter in leaf cells.

Yet another area of agricultural interest is to improve the yield of crop plants and to improve the aesthetic qualities of certain decorative plants. The yield of a plant crop, and the aesthetics of certain decorative plants, may be improved by growing plants that are larger than the wild-type plant in vegetative and/or reproductive structure, as well as improving the growth rate of plants.

A number of compounds have been touted in the prior art as improving the rate of plant growth and biomass production in useful components of the plant. For example, cyclodextrins applied to tissue culture media has been asserted to improve the rate of cell tissue culture growth by mechanisms including increased cell division (See, e.g., U.S. Pat. No. 6,087,176). Certain plant growth hormones, such as auxins (which promote, among other things, root growth), cytokinins, and gibberellic acid (which promotes, among other things, stem growth) when applied to plant tissues are also known to promote increased cellular division. It also is known in the art that certain growth factors may be used to increase plant and/or plant flower size. Unfortunately, isolation and application of such growth hormones and factors is costly and time consuming.

U.S. Pat. No. 5,859,338 discloses that modification of the CLAVATA1 gene of *Arabidopsis thaliana* causes a loss normal control of cell division in shoot apical meristems and floral meristems. In either case, the loss of control is said to cause an enlargement of the meristem. In flowers, the enlargement is said to lead to an increase in the number of floral organs, including an increase in carpel number, which increases fruit size and seed number. U.S. Pat. No. 5,859,338 provides clavatal nucleic acids and proteins, and modified clavatal nucleic acids and proteins, to result in altered meristem phenotypes.

U.S. Pat. No. 5,750,862 discloses a method for controlling plant cell growth comprising modulating the level and or catalytic activity of a cell cycle control protein in the plant. In particular the patent discloses that by elevating levels of the protein p34$^{cdc2}$, regeneration into plants of single or groups of cells can be facilitated. Control of regeneration may also be effectuated by control of regulatory elements which indirectly result in modulation of p34$^{cdc2}$ activity.

A need, therefore, exists for plants having improved stress resistance to drought and/or freeze, possessing larger size attributes than wild-type counterpart varieties, and having increased tolerance to salt in the soil in which they are growing, and which provide for increased biomass of useful components.

SUMMARY OF THE INVENTION

The present invention discloses a transgenic plant having upregulated expression of vacuolar pyrophosphatase. It has been found that plants displaying such upregulated activity are generally larger than wild-type counterparts, demonstrate improved stress resistance to drought and/or freeze, have increased tolerance to salt in the media in which they are growing, and display higher meristematic activity (cell division) leading to greater biomass in certain plant parts as compared to wild type plants.

Any suitable exogenous nucleic acid molecule which alters expression of vacuolar pyrophosphatase in the plant can be used to transform the transgenic plants in accord with the present invention. The exogenous nucleic acid can comprise nucleic acid that encodes a vacuolar pyrophosphatase protein (an exogenous vacuolar pyrophosphatase), such as AVP1, a functional portion thereof (peptide, polypeptide), or a homologue thereof, and/or nucleic acid that alters expression of the endogenous vacuolar pyrophosphatase of the plant into which the exogenous nucleic acid is introduced. By "exogenous nucleic acid" it is meant a nucleic acid from a source other than the plant cell into which it is introduced, or into a plant or plant part from which the transgenic part was produced. The exogenous nucleic acid used for transformation can be RNA or DNA, (e.g., cDNA, genomic DNA). In addition, the exogenous nucleic acid can be circular or linear, double-stranded or single-stranded molecules. Single-stranded nucleic acid can be the sense strand or the anti-sense strand. By a "functional portion" of a nucleic acid that encodes a vacuolar pyrophosphatase protein it is meant a portion of the nucleic acid that encodes a protein or polypeptide which retains a functional characteristic of a vacuolar pyrophosphatase protein. In a particular embodiment, the nucleic acid encodes AVP1, a functional portion or a homologue thereof. The AVP1 nucleic acid may be obtained, for example, from *Arabidopsis* or any other plant, or synthetically synthesized.

Nucleic acid that alters expression of the endogenous vacuolar pyrophosphatase of the plant into which the exogenous nucleic acid is introduced includes regulatory sequences (e.g., inducible, constitutive) which function in plants and antisense nucleic acid. Examples of regulatory sequences include promoters, enhancers. The nucleic acid can also include, for example, polyadenylation site, reporter gene and/or intron sequences and the like whose presence may not be necessary for function or expression of the nucleic acid but can provide improved expression and/or function of the nucleic acid by affecting, for example, transcription and/or stability (e.g., of mRNA). Such elements can be included in the nucleic acid molecule to obtain optimal performance of the nucleic acid.

The nucleic acid for use in the present invention can be obtained from a variety of sources using known methods. For example, the nucleic acid encoding a vacuolar pyrophosphatase (e.g., AVP1) for use in the present invention can be derived from a natural source, such as tobacco, bacteria, tomato or corn. In one embodiment, the nucleic acid encodes a vacuolar pyrophosphatase that corresponds to a wild type of the transgenic plant. In another embodiment, the nucleic acid encodes a vacuolar pyrophosphatase that does not correspond to a wild type of the transgenic plant. Nucleic acid that alters expression of the endogenous vacuolar pyrophosphatase of the plant into which the exogenous nucleic acid is introduced (e.g., regulatory sequence) can also be chemically synthesized, recombinantly produced and/or obtained from commercial sources.

A variety of methods for introducing the nucleic acid of the present invention into plants are known to those of skill in the art. For example, *Agrobacterium*-mediated plant transformation, particle bombardment, microparticle bombardment (e.g., U.S. Pat. No. 4,945,050; U.S. Pat. No. 5,100,792) protoplast transformation, gene transfer into pollen, injection into reproductive organs and injection into immature embryos can be used. The exogenous nucleic acid can be introduced into any suitable cell(s) of the plant, such as root cell(s), stem cell(s) and/or leaf cell(s) of the plant.

Any suitable plant, including angiosperms, monocots and dicots, and gynmosperms, and algae can be used to produce the transgenic plants, tissue cultures or cell cultures of the present invention. For example, tomato, corn, tobacco, rice, sorghum, cucumber, lettuce, turf grass, ornamental (e.g., larger flowers, larger leaves) and legume plants can be transformed as described herein to produce the transgenic plants of the present invention. In addition, the transgenic plants of the present invention can be grown in any medium which supports plant growth such as soil or water (hydroponically).

A transgenic plant of the present invention is preferably tolerant to high salt concentrations in soil. By the term "salt" it is meant to include any salt, that is a compound formed when hydrogen of an acid is replaced by a metal or its equivalent, and includes, without limitation, salts comprising monovalent and divalent toxic cations, NaCl, KCl, $CaCl_2$, MgCl, CdCl, ZnCl, and sulfide salts.

Salt tolerance may be introduced into a plant of the present invention by transforming plant cells with exogenous nucleic acid which alters the expression of vacuolar pyrophosphatase in the plant such that expression is upregulated. Any suitable vacuolar pyrophosphatase, several of which have been cloned, can be used in the compositions and methods of the present invention (e.g., Sarafian, V., et al., *Proc. Natl. Acad. Sci., USA,* 89:1775-1779 (1992); Lerchl, J., et al., *Plant Molec. Biol.,* 29: 833-840 (1995); Kim, Y., et al., *Plant Physiol.,* 106:375-382 (1994)). In a particular embodiment, the present invention relates to a transgenic plant which is tolerant to salt comprising an exogenous nucleic acid construct which is designed to overexpress AVP1 (Sarafian, V., et al, *Proc. Natl. Acad. Sci., USA,* 89:1775-1779 (1992)). Transformation of the plant cells may be carried out in a whole plant, seeds, leaves, roots or any other plant part. Such transgenic plants are preferably altered such that they grow in a concentration of salt that inhibits growth of a corresponding non-transgenic plant. Transgenic progeny of the transgenic plants, seeds produced by the transgenic plant and progeny transgenic plants grown from the transgenic seed, which are also the subject of the present invention, advantageously carry such salt tolerant trait. Plants may be regenerated from transformed cells to yield transgenic plants, which may be screened for certain levels of salt tolerance. In a preferred embodiment, the exogenous nucleic acid encodes AVP1, or a homologue thereof. Preferably expression of the vacuolar pyrophosphatase in the plant is enhanced to an extent that the transgenic plant is tolerant to sodium chloride (NaCl) when the NaCl concentration is from about 0.2M to about 0.3M. A transgenic plant capable of growing in salt water may also be produced by introducing into one or more cells of a plant nucleic acid which upregulates expression of vacuolar pyrophosphatase in the plant to yield transformed cells. As used herein, "salt water" includes water characterized by the presence of salt, and preferably wherein the concentration of salt in the water is from about 0.2M to about 0.4M. In one embodiment, salt water refers to sea water.

The transgenic plants of the present invention can also be used to produce double transgenic plants which are tolerant to salt (about 0.2M to about 0.4M salt concentration). In one embodiment, the present invention relates to a double transgenic plant which is tolerant to salt comprising one or more plant cells transformed with exogenous nucleic acid which alters expression of a vacuolar pyrophosphatase and an $Na^+/H^+$ antiporter in the plant. The vacuolar pyrophosphatase in an advantageous construct is AVP1, or a homologue thereof, and the $Na^+/H^+$ antiporter is AtNHX1, or a homologue thereof. The present invention also encompasses transgenic progeny of the double transgenic plant, as well as seeds produced by the transgenic plant and a progeny transgenic plant grown from the seed.

Drought and/or freeze tolerance may also be introduced into plants by transforming plant cells with exogenous nucleic acid which alters the expression of vacuolar pyrophosphatase in the plant such that such expression is upregulated. In a preferred embodiment there is provided a substantially drought and/or freeze resistant transgenic plant which comprises a genome having one or more exogenously introduced vacuolar $H^+$-translocating pump genes. A particularly preferred fertile transgenic plant eliciting drought and/or freeze tolerance, as well as the ability to grow in saline soils, comprises an isolated exogenous chimeric DNA construct encoding vacuolar $H^+$-translocating pump, preferably operably linked to a promoter, such as the 35-S promoter or any other strong promoter, including, without limitation, tissue specific promoters. The transgenic plant may contain a polynucleotide sequence comprising an exogenous tonoplast pyrophosphate $H^+$ pump gene operably linked to a promoter. In yet another particularly preferred drought and/or freeze resistant transgenic plant having the capacity to grow in saline soils, the polynucleotide sequence comprises an exogenous tonoplast pyrophosphate $H^+$ pump gene operably linked to a double tandem enhancer of the 35S promoter. A particularly preferred tonoplast pyrophosphate $H^+$ pump gene is the AVP1 gene.

Upregulation of expression of vacuolar pyrophosphatase by the methods described above may also be used to provide a plant having larger vegetative and/or sexual organs than wild type counterpart plants. That is, the present invention provides for a method of increasing the yield of a plant comprising introducing into one or more cells of a plant nucleic acid which alters expression of vacuolar pyrophosphatase in the plant to yield transformed cells, thereby increasing the yield of the plant. The method can further comprise regenerating plants from the transformed cells to yield transgenic plants and selecting a transgenic plant which is larger than its corresponding wild type plant, thereby producing a transgenic plant which is larger than its corresponding wild type plant. Also encompassed by the present invention is a method of making a transgenic plant (e.g., an ornamental plant) having increased flower size compared to its corresponding wild type plant comprising introducing into one or more cells of a plant nucleic acid which alters expression of vacuolar pyrophosphatase in the plant to yield transformed cells.

Upregulation of expression of vacuolar pyrophosphatase by the methods described above may also be used to provide a plant with meristematic activity cell division rate which is enhanced over wild-type counterpart plants. As would be recognized by one of ordinary skill in the art, meristems are central to higher plant development, as almost all post-embryonic organs, including roots, leaves, flowers and axillary meristems and cambium are initiated by either shoot or root meristems. Increased meristematic activity results in higher biomass in one or more aspects of plant structure, as evidenced by dry weight of plant structure, root structure as well as stem structure. Increased meristemic activity is hypothesized to result in increased rate of shoot regeneration in root, leaf, hypocotyl, and cotyledon explants, and increased overall plant growth rate.

The present inventor has discovered that overexpression of a pyrophosphate driven proton ($H^+$) pump at the vacuole leads to a greater proton pumping capacity that results in a greater ion uptake into the vacuoles that lowers the osmotic potential of the cells, and also leads to an increase in the capacity of plant cells to divide and multiply. As would be understood by one of ordinary skill in the art, such finding can have great commercial importance, e.g., reducing time for wood, corn etc. production by transforming cells so as to overexpress such pumps, and enhancing shoot regeneration capacity in plants with poor or slow regeneration capacity, such as woody plants, crops, e.g. corn, and ornamentals e.g., orchids. Overexpression so as to produce such enhanced cell division and multiplication may be performed using any of the construct described herein. While a number of inducible promoters and tissue specific promoters may be used to trigger overexpression of the gene and/or homologues of the gene, a preferred construct includes a tonoplast pyrophosphate driven $H^+$ pump gene (AVP-1) operably linked to a chimeric promoter (e.g., double tandem enhancer of 35S promoter) designed to overexpress AVP-1.

There is also disclosed in the present invention novel gene cassettes including cassettes comprising a tonoplast pyrophosphate driven $H^+$ pump gene operably linked to a chimeric promoter. A novel gene cassette comprising an exogenous tonoplast pyrophosphate driven $H^+$ pump gene operably linked to a promoter, as well as novel coding sequences comprising an exogenous tonoplast pyrophosphate driven $H^+$ pump gene operably linked to a double tandem enhancer of the 35S promoter. Preferably such coding sequence is designed to overexpress AVP1.

There is also disclosed in the present invention novel expression vectors including an expression vector containing a polynucleotide sequence comprising a exogenous tonoplast pyrophosphate driven $H^+$ pump gene operably linked to a double tandem enhancer of the 35S promoter and further operatively linked to a multiple cloning site, and an expression vector containing a polynucleotide sequence comprising a exogenous tonoplast pyrophosphate driven $H^+$ pump gene operably linked to a double tandem enhancer of the 35S promoter and further operatively linked to a heterologous coding sequence.

It is recognized by the present inventor, that the disclosed invention may have application to any plant, including, without limitation, crop plants, ornamental plants, grasses, shrubs, or any other plant found useful or pleasing to man, including having application to monocots, dicots, angiosperms, gymnosperms, and algae.

BRIEF DESCRIPTION OF THE DRAWINGS

The above description, as well as further objects, features and advantages present invention will be more fully understood with reference to the following detailed description when taken in conjunction with the accompanying drawings, wherein:

FIGS. 1B(1), 1B(2) and 1B(3) are a photomicrographs of the root and root hairs of representative five day old seedlings obtained from representative WT, 1' and 2' of FIG. 1A grown parallel to the surface on vertical plant nutrient agar plates;

FIGS. 9A and 9B are illustrations demonstrating the 35SAVP-1 theorized mechanism for a higher accumulation of solids into vacuoles via a proton driven function versus that of WT vacuoles.

Figure 1A:
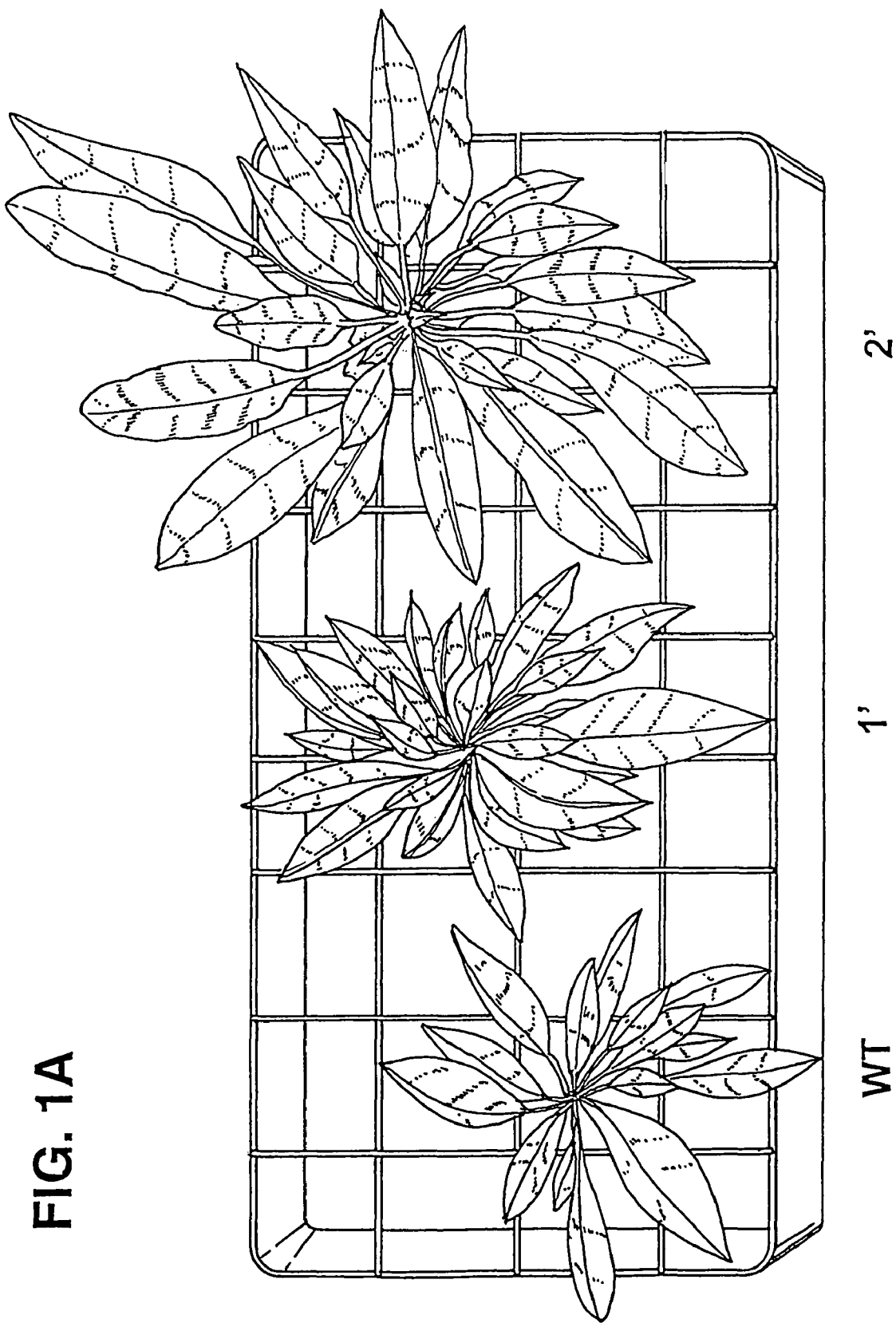
FIG. 1A is an overhead view of representative (out of 10 plants each) wild type (WT) and two independent transgenic lines (1' and 2') grown hydroponically for seven weeks on a 10 hour light/dark cycle.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Since plant vacuoles constitute 40 to 99% of the total intracellular volume of a mature plant cell, changes in the size of the vacuole have dramatic effects upon cell size (R. G. Zhen, E. J. Kim, P. A. Rea, in The Plant Vacuole. (Academic Press Limited, 1997), vol. 25, pp. 298-337). The volume of the vacuole is controlled by ion and water fluxes mediated by pumps and transporters. In plants the driving force that triggers the movement of ions, solutes and water across membranes is a proton gradient. The activity of the vacuolar $H^+$-pumps results in luminal acidification and the establishment of a $H^+$ electrochemical potential gradient across the vacuolar membrane, which powers the secondary active transporters of inorganic ions, sugars, and organic acids. The activity of these transporters modulates cellular pH and ion homeostasis and leads to the accumulation of solutes required to generate the osmotic potential that promotes vacuolar expansion (H. Sze, X. Li, M. G. Palmgren, The Plant Cell 11, 677-689 (1999)).

There are three distinct pumps that generate proton electrochemical gradients. One at the plasma membrane that extrudes $H^+$ from the cell (PM $H^+$-ATPase) and two at the vacuolar membrane or other endomembrane compartments that acidify their lumen (the vacuolar type $H^+$-ATPase and $H^+$-PPase) (R. A. Leigh, in The Plant Vacuole L. a. Sanders, Ed. (Academic Press, San Diego, Calif., 1997), vol. 25, pp. 171-194.).

Previous work has shown that a decrease in the levels of the A subunit of the vacuolar $H^+$-ATPase of carrot, using an antisense construct, resulted in a plant with reduced cell expansion and altered leaf morphology (J. P. Gogarten, et al., The Plant Cell 4, 851-864 (1992)). The present inventor has hypothesized that an increased supply of $H^+$ into the vacuole could accelerate cell expansion. Recently, based on the theory that as the availability of protons in the vacuolar function of ion accumulation, it has been hypothesized by the same inventor that accumulation of solids in the vacuoles might be useful to protect against draught and to provide for a more freeze resistant plants.

The present inventor has recognized that plants have a number of vacuolar $H^+$-translocating pumps, and that by upregulating their activity, increasing their expression, upregulating their transcription and/or translation, or increasing their copy number that one can increase accumulation of solids in the vacuole due to an increase in the availability of protons in the vacuoles. The inventor tested this hypothesis by increasing the copy number of the vacuolar $H^+$-translocating pump, the inorganic pyrophosphatase or V-PPase that consists of a single polypeptide (R. G. Zhen, E. J. Kim, P. A. Rea, in The Platt Vacuole. (Academic Press Limited, 1997), vol. 25, pp. 298-337). In Arabidopsis the V-PPase encoded by the AVP-1 gene is capable of generating a $H^+$ gradient across the vacuole membrane (tonoplast) similar in magnitude to that of the vacuolar $H^+$-ATPase (V. Sarafian, Y. Kim, R. J. Poole, P. A. Rea, Proc. Natl. Acad. Sci. 89, 1775-1779 (1992)). As would be understood by one of ordinary skill in the art, similar genes in other plants should function in a similar manner.

It is known that $H^+$-PPase is the main proton pump of vacuolar membranes in growing tissue. The later may be due to the fact that in growing tissue, nucleic acids, DNA, RNAs, proteins and cellulose etc. are actively being synthesized for the construct of the new cells, and as a result, a large amount of PPi is produced as a by-product of these metabolic processes. The energy stored in the PPi molecule may be transformed into a different source of energy, namely a $H^+$-gradient across the vacuolar membrane. This $H^+$-gradient constitutes the driving force for the vacuolar accumulation of solutes that generate the sufficient osmotic differential that enables the plant cell to initiate growth. While the present invention is not limited in any manner to any particular hypothesis for the increased growth effects seen, the present inventor has hypothesized that in transgenic plants overexpressing AVP-1 that the greater number of $H^+$-PPiases has a positive effect on the velocity of the generation of the $H^+$ gradient, rendering a more active meristem.

In one embodiment, a construct comprising a vacuolar pyrophosphatase gene operably linked to a promoter designed to overexpress the vacuolar pyrophosphatase (e.g., an expression cassette) is used to produce the transgenic plants of the present invention. As used herein the term "overexpression" refers to greater expression/activity than occurs in the absence of the construct. In a particular embodiment, a construct comprising an AVP1 gene operably linked to a chimeric promoter designed to overexpress AVP1 is used to produce the transgenic plants of the present invention. More particularly, the present invention relates to a construct wherein the AVP1 gene is operably linked to a double tandem enhancer of a 35S promoter.

The transgenic plants of the present invention may find utility other than those associated with the food value or ornamental value, industrial value such as, for example, wood production. For example, the transgenic plants of the present invention may uptake different or more ions than their wild-type counterparts. As discussed below, studies with mutant yeast strains (ena1) demonstrates that $H^+$-translocating pumps at the vacuole plays an important role in cation detoxification in higher plants (the plant components involved in an intracellular cation detoxification system being identified by complementing salt-sensitive mutants of the budding yeast Saccharomyces cerevisiae). Transgenic plants and/or progeny thereof comprising exogenous nucleic acid which alters expression of vacuolar pyrophosphatase in the plant in accord with such studies may be used to bioremediate soil and growth medium. Such plants can be used to remove cations (e.g., monovalent and/or divalent cations) from a medium which can support plant growth (e.g., soil, water). For example, transformed plants of the present invention can be used to remove sodium (Na), lead (Pb), manganese (Mn) and/or calcium (Ca) ions from a medium which supports plant growth.

To demonstrate the effect that an increased supply of $H^+$ into the vacuole would have on resistance to drought and/or freeze, and tolerance to salt growth, as well as size of the plants, the present inventor generated transgenic plants containing extra copies of a vacuolar proton pump, AVP-1.

Arabidopsis thaliana plants were transformed with constructs containing the AVP-1 gene. Transgenic lines containing extra copies of this gene were then isolated. The AVP-1, open reading frame was cloned into the Xma1 site of a modified pRT103 [R. Topfer, V. Matzeit, B. Gronenborn, J. Schell and H-H. Steinbiss, Nucleic acid Research 15, 5890 (1987)]. This vector contains a tandem repeat of the 35-S promoter. A HindIII fragment containing the 35-S tandem promoter, AVP-1 ORF and the polyadenylation signal was subcloned into the HindIII site of the pPZP212 vector [P. Hajdukiewicz, Z. Svab and P. Maliga, Plant Molecular Biology 25, 989-994 (1994)]. Agrobacterium-mediated transformation was performed via vacuum infiltration of flowering Arabidopsis thaliana (ecotype columbia). Transgenic plants were selected by plating seeds of the transformed plants on plant nutrient agar plates supplemented with 25 mg/liter kanamycin. Plants were subsequently selected for two generations to identify transgenic plant homozygous for the transgene.

FIG. 1A is an overhead picture of representative (out of 10 plants each) wild type (WT) and two independent transgenic lines (1' and 2') grown hydroponically for seven weeks on a 10 hour light/dark cycle. As can be seen in FIG. 1A, a visual comparison of transgenic line 2', which expresses the AVP-1 protein at highest level, transgenic line 1', and wild type (WT), demonstrates that the amount of AVP-1 correlates with the size of the plants. The mass of the transgenic plants was found to be greater than that of wild type. The dry weight of the entire transgenic plants, measured after 24 hours at 75° C. (n=4), for transgenic lines 1' and 2' was found to be 1.5 and 3 times greater then that of wild-type (WT).

FIG. 1B(1), FIG. 1B(2) and FIG. 1B(3) are photomicrographs (magnification: times 40; bar length on photograph=2 mm) of the root and root hairs of representative five day old seedlings obtained from representative WT, 1' transgenic and 2' transgenic of FIG. 1A grown parallel to the surface on vertical plant nutrient agar plates. Seedlings of both transgenic lines 1' and 2' showed root hairs with an average length 40 and 70% larger than wild-type (WT) root hairs (FIG. 1B) (Root hair length along the whole root was determined from five members of each set of seedlings. An average of 80 root hairs per plant were measured). The length of the root hairs is correlated with the size of the vacuole, so the increased size of the root hair is likely to result from increased vacuolar volume. This compares with the *Arabidopsis* mutant rdh3 which has been reported to have reduced vacuolar volume and is a short plant with abnormally short root hairs (M. E. Galway, J. W. J. Heckman, J. W. Schiefelbein, *Planta* 201, 209-218 (1997)). It is recognized that the increased root structure will have a positive impact on soil erosion, nitrogen fixation in legumes, and will aid in water and nutrient uptake by the plant.

Figure 1C:
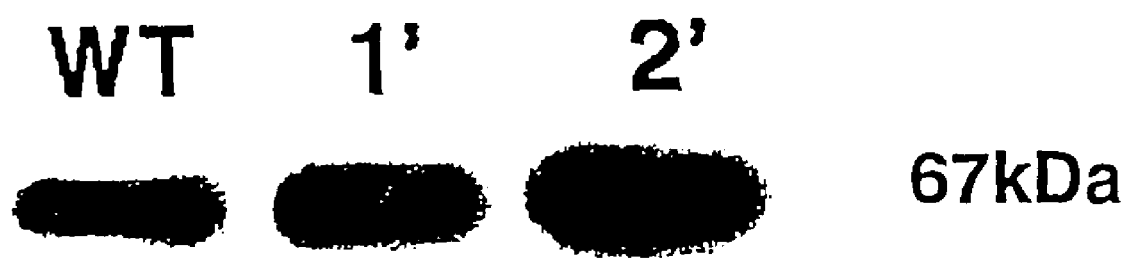
FIG. 1C is an immunoblot of membrane fractions isolated from wild type (WT) and two independent transgenic lines (1' and 2') overexpressing AVP-1.

FIG. 1C is an immunoblot of membrane fractions isolated from wild type (WT) and two independent transgenic lines (1' and 2') overexpressing AVP-1. Total membrane fractions were isolated from shoots of eight week old wild type (WT) and AVP-1 transgenic plants (1' and 2') grown in a hydroponic media for 8 weeks. Homogenate of plant shoots were sequentially centrifuged for 15 and 30 min at 8,000 and 100,000 rpms respectively. The 100 mg membrane pellet was re-suspend in 10 mM Tris, pH 7.5, 150 mM NaCl, 1 mM EDTA, 10% glycerol and 1 mM PMSF Protein (10 ug) was separated on a 10% SDS-PAGE, electroblotted and immunostained with antibodies raised against a KLH-conjugated synthetic peptide corresponding to the putative hydrophilic loop IV of the AVP-1 protein (V. Sarafian, Y. Kim, R. J. Poole, P. A. Rea, Proc. Natl. Acad. Sci. 89, 1775-1779 (1992)). PPase was detected by chemiluminescence. FIG. 1C illustrates that the transgenic lines (1' and 2') express AVP-1 protein at higher levels than the wild type (WT) (that is, 1'=1.6 fold increase and 2'=2.4 fold increase over WT).

As wheat that has been deprived of water is rendered more drought tolerant by an increase in cell $K^+$ content (from 100 mM to 300 mM) (S. Gupta, G. Berkowitz, P. Pier, Plant Physiol 89, 1358-1365 (1989)), it is hypothesized (but the invention is not hereby limited by such theory) that the increased drought resistance of the AVP-1 transgenic plants may be a consequence of their higher vacuolar concentration of potassium that results in a increased water retention capability. Laboratory tests appear to confirm this.

Figure 2:
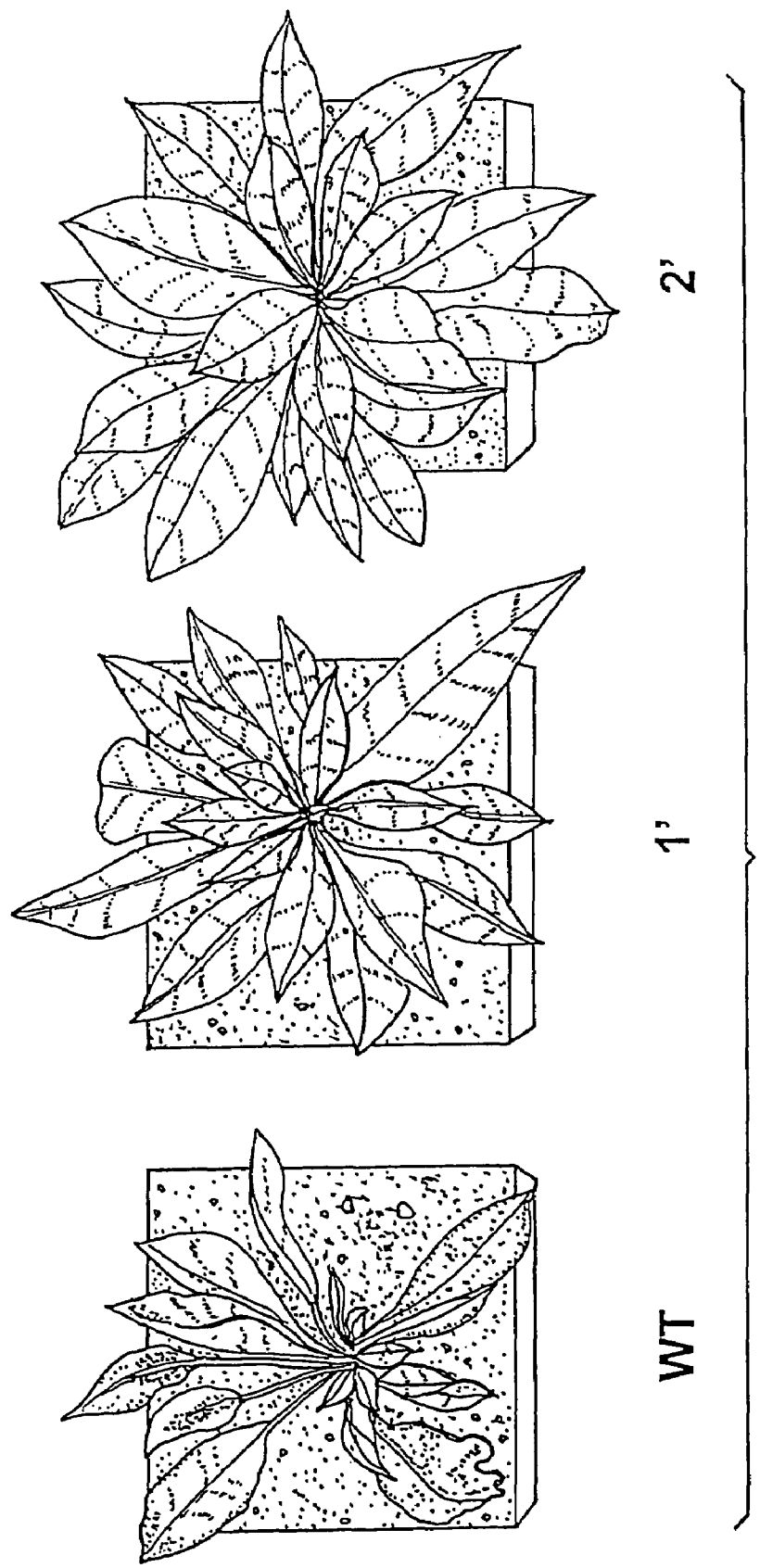
FIG. 2 is an overhead view of a representative wild type plant (WT) versus representative transgenic plants overexpressing AVP-1 (1' and 2') after exposure to 7 days of water deficit stress.

FIG. 2 is an overhead view of a representative wild type plant (WT) versus representative transgenic plants overexpressing AVP-1 (1' and 2') after exposure to 7 days of water deficit stress. Wild type and transgenic plants overexpressing AVP-1 (FIG. 3A) were tested for drought tolerance (24°.C.). After 7 days of water deficit stress wild type (WT) plants withered, whereas plants from both 35S AVP-1 transgenic lines (1' and 2') were turgid and alive. Furthermore, when the drought stressed plants were then watered, transgenic plants pursued normal growth, bolted and set seeds, whereas wild type plants died. The relative water content of leaves from wild type and 35S AVP-1 transgenic plants were determined along the water deficit stress, demonstrating increased water retention by the transgenic lines as compared to the WT plants.

Figure 6:
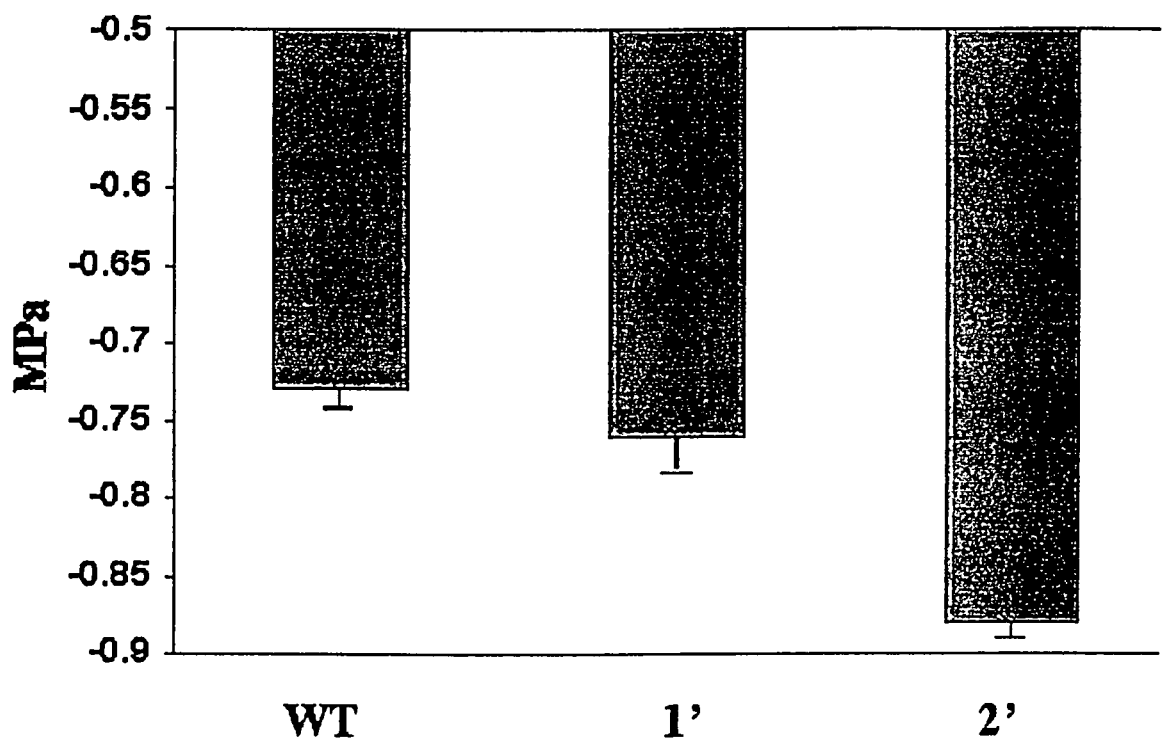
FIG. 6 is bar graph of osmotic potential in megapascals (MPa) of fully hydrated leaves from WT and two AVP-1 overexpressing lines (1' and 2') from Arabidopsis plants. The leaf osmotic potential was measured by using a Wescor (Logan, Utah) 5500 osmometer.

FIG. 6 is bar graph of osmotic potential of fully hydrated leaves from wild-type (WT) and two AVP-1 overexpressing lines (1' and 2') from *Arabidopsis* plants. The decreased osmotic potential in leaves of transgenic plants measured at a constant water content is consistent with the contention that AVP-1 overexpression results in increased solute accumulation, and therefore enhancing water retention capability.

While not illustrated in the accompanying illustrations, similar results may be seen with respect to freeze challenge (<0° C.) over a 24 hour or more period for a number of plant species. While not limited to such hypothesis, transgenic plants overexpressing AVP-1 (1' and 2') are believed to provide enhanced protection from freeze as compared to wild type (WT) plants due to the higher amounts of cations in the vacuoles. Higher amounts of cations confer a greater osmotic pressure that leads to a greater water retention capability endowing the plants not only with the ability to withstand low soil water potentials, but also providing greater protection from freezing that leads to significant desiccation of the plants.

Figure 3:
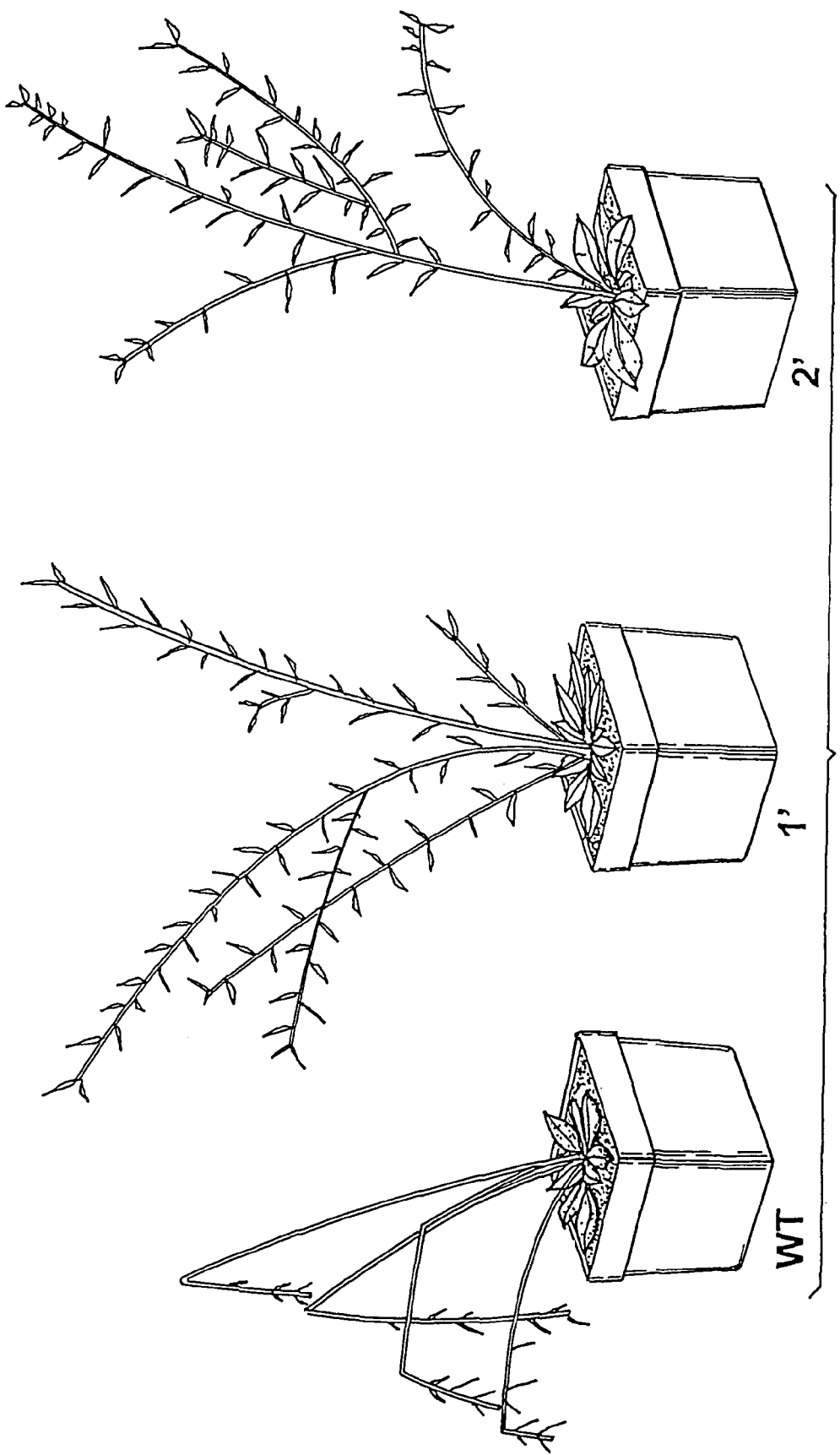
FIG. 3 is a perspective view of wild-type plants (WT) versus representative transgenic plants overexpressing AVP-1 (1' and 2') grown in salty soil.

FIG. 3 is a perspective view of wild type plants (WT) versus representative transgenic plants overexpressing AVP-1 (1' and 2') grown in salty soil. Five wild-type plants (WT) and five of the two AVP-1 overexpressing transgenic lines (1' and 2') were grown on soil in a 10 hour light/dark cycle. Plants were watered with a diluted nutrient solution (1/8 MS salts) for six weeks and subsequently watered with a diluted nutrient solution supplemented with NaCl. The concentration of NaCl began with, 100 mM and was increased every four days by 50 mM. The illustrations in FIG. 3 corresponds to representative plants at the tenth day in the presence of 300 mM NaCl. FIG. 3 illustrates that the two AVP-1 plant types (1' and 2') were significantly hardier in salty soil as compared to wild-type plants. The fact that genetically engineered *Arabidopsis thaliana* plants that overexpress either AVP1 (the pyrophosphate-energized vacuolar membrane proton pump, this work) or AtNHX1 (the $Na^+/H^+$ antiporter, (Apse, M., et al., *Science,* 285:1256-1258 (1999)) and this work) are capable of growing in the presence of high NaCl concentrations strongly supports the strategy described herein. A double transgenic plant would be expected to demonstrate a further enhanced salt-tolerant phenotype. These *Arabidopsis thaliana* transporters or their counterparts may perform similar function in important agricultural crops. The increased size of $^{35}S$ AVP1 *Arabidopsis* transgenic plants also contribute to potential yield increases in genetically engineered crops.

A Working Model of Cation Homeostasis in Plant Organelles

While the present invention is not limited to any particular hypothesis, the present inventor have developed a working model for cation homeostasis in plant organelles which may explain the unexpected results discovered with respect to the transgenic plants disclosed herein.

In plants, most of the transport processes are energized by the primary translocation of protons. $H^+$-translocating pumps located at the plasma membrane and tonoplast translocated $H^+$ from the cytosol to extracellular and vacuolar compartments, respectively (Rea, P. A., et al., Tonoplast Adenosine Triphosphate and inorganic Pyrophosphatase. In: *Methods Plant Biochem*., pp. 385-405, Academic Press Limited, London (1990)). The plant tonoplast contains two $H^+$-translocating pumps; the V-ATPase and the inorganic pyrophosphatase or V-PPase. Their action results in luminal acidification and the establishment of a $H^+$ electrochemical potential gradient across the tonoplast (Davies, J. M., et al., The Bioenergetics of Vacuolar H+ Pumps. In: *Plant Vacuole*, pp. 340-363, Leigh, R. A., Sanders, D. (eds.), Academic Press, San Diego (1997)). The vacuolar membrane is implicated in a broad spectrum of physiological processes that include cytosolic pH stasis, compartmentation of regulatory $Ca^{2+}$, sequestration of toxic ions such as $Na^+$, turgor regulation, and nutrient storage and retrieval. The vacuole constitute 40 to 99% of the total intracellular volume of a mature plant cell. The vacuolar proton pumping pyrophosphatase is a universal and abundant component of plant tonoplast capable of generating a steady-state trans-tonoplast $H^+$ electrochemical potential similar or greater than the one generated by the V-ATPase (Rea, P. A., et al., Tonoplast Adenosine Triphosphate and Inorganic Pyrophosphatase. In: *Methods Plant Biochem.*, pp. 385-405, Academic Press Limited, London (1990)). Pyrophosphate (PPi) is a by-product in the activation or polymerization steps of a wide range of biosynthetic pathways and in plants serves as an alternative energy donor to ATP for sucrose mobilization via sucrose synthetase, for glycolysis via PPi: fructose-6-phosphate phosphotransferase and for tonoplast energization via the vacuolar proton pumping pyrophosphatase (Stitt, M., Bot. Acta 111:167-175 (1998)).

Most of intracellular organelles, including clathrin-coated vesicles, endosomes, Golgi membranes and vacuoles have acidic interiors (Xie, X. S., et al., *J. Biol. Chem.*, 264:18870-18873 (1989)). This acidification is mediated by a proton-translocating electrogenic ATPase and in plant vacuoles also via a pyrophosphate-driven proton pump V-PPase (Davies, J. M., et al., The Bioenergetics of Vacuolar H+ Pumps. In: Leigh R. A., Sanders, D., (eds) *The Plant Vacuole*, pp. 340-363, Academic Press, San Diego (1997); Zhen, R. G., et al., "The Molecular and Biochemical Basis of Pyrophosphate-Energized Proton Translocation at the Vacuolar Membrane Academic Press Limited (1997)). There exists a requirement of anion transport to maintain net electroneutrality (al-Awqati, A., *Curr. Opin. Cell. Biol.*, 7:504-508 (1995)).

Figure 4A:
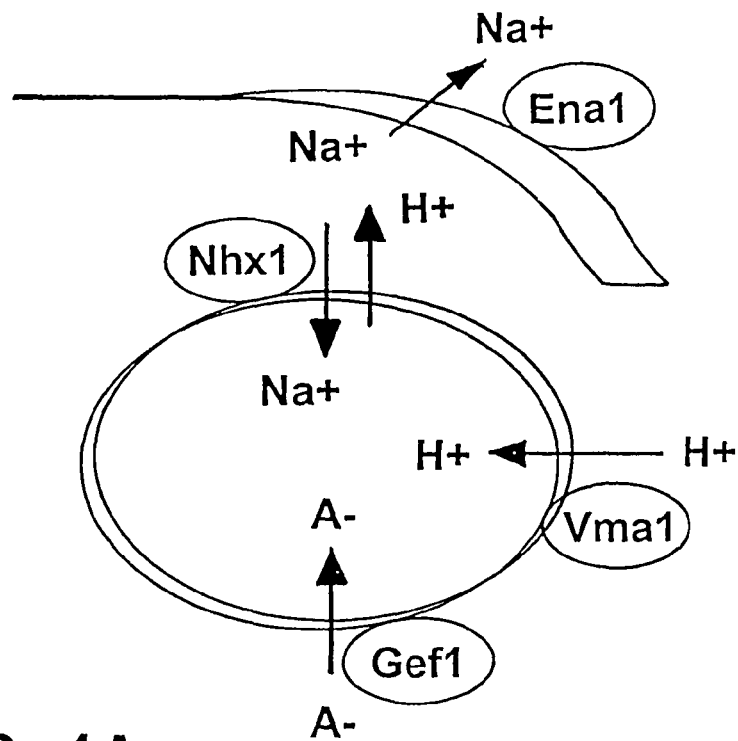
FIG. 4A is a schematic representation of a working model of the transporters involved in sodium sequestration at the yeast pre-vacuolar compartment; Nhx1 ($Na^+/H^+$ antiporter), Vma1 (vacuolar membrane $H^+$-ATPAse), Gef1 (yeast CLC chloride channel), Ena1 (plasma membrane $Na^+$-ATPase).
Figure 4B:
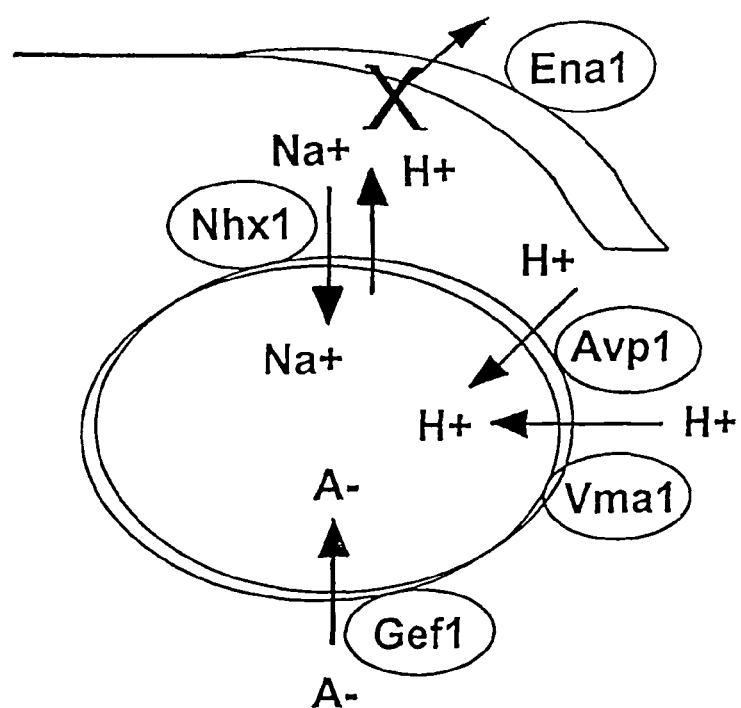
FIG. 4B is a schematic representation of a working model of the transporters involved in sodium sequestration at the yeast pre-vacuolar compartment shown in FIG. 4A, which also includes Avp1 (A. thaliana vacuolar pyrophosphate-energized proton pump).

FIG. 4A is a schematic representation of a working model of the transporters involved in sodium sequestration at the yeast pre-vacuolar compartment; Nhx1 ($Na^+/H^+$ antiporter), Vma1 (vacuolar membrane $H^+$-ATPase), Gef1 (yeast CLC chloride channel), Ena1 (plasma membrane $Na^+$-ATPase). The yeast member of the CLC voltage-gated chloride channel superfamily, Gef1, is required for copper loading in late-Golgi vesicles and for cation sequestration in the pre-vacuolar compartment in yeast (Gaxiola, R. A., et al., *Proc. Natl. Acad. Sci. USA*, 95:4046-4050 (1998); Gaxiola, R. A., et al., *Proc. Natl. Acad. Sci. USA*, 96:1480-1485 (1999); Example 1). Furthermore, it has been shown that the defects of gef1 mutants can be suppressed by the introduction of the prototype member of the CLC superfamily, the *Torpedo marmorata* CLC-0 or by the introduction of *Arabidopsis thaliana* CLC-c and CLC-d chloride channel genes (Hechenberger, M., et al., J. Biol. Chem., 271:33632-33638 (1996); Gaxiola, R. A., et al., *Proc. Natl. Acad. Sci. USA*, 95:4046-4050 (1998)). FIG. 4B is a schematic representation of a working model of the transporters involved in sodium sequestration at the yeast pre-vacuolar compartment shown in FIG. 4A, which also includes Avp1 (*A. thaliana* vacuolar pyrophosphate-energized proton pump).

While not wishing to be bound by theory, two observations led to the proposal of the model for $Na^+$ sequestration in yeast illustrated in FIGS. 4A and 4B. First, gef1 mutants are sensitive to high NaCl concentrations. Second, the $Na^+/H^+$ exchanger Nhx1 is localized to the pre-vacuolar compartment (Nass, R., et al., *J. Biol. Chem.*, 273:21054-21060 (1998)). The model proposed in FIGS. 4A and 4B posits that $Na^+$ sequestration by Nhx1 depends on the vacuolar $H^+$-ATPase and Gef1, the chloride channel. Gef1-mediated anion influx allows the establishment by the vacuolar $H^+$-ATPase of a proton gradient sufficient in magnitude to drive the uphill accumulation of $Na^+$ via $Na^+/H^+$ exchange.

Based on such models, it was theorized that increasing the influx of protons into the postulated endosomal compartment should improve $Na^+$ sequestration via the Nhx1 exchanger. In order to increase the $H^+$ availability the *A. thaliana* gain-of-function mutant gene AVP1-D that codes for the vacuolar pyrophosphate-energized proton pump was expressed (FIG. 3B) (Zhen, R. G., et al., *J. Biol. Chem.*, 272:22340-22348 (1997)). This plant pump expressed in yeast restored the $Na^+$ resistance of the test strain, but only if the strain had functional NHX1 and GEF1 genes. Furthermore, Gef1p and Nhx1p co-localize within a common organelle, the pre-vacuolar compartment (Gaxiola, R. A., et al., *Proc. Natl. Acad. Sci. USA*, 96:1480-1485 (1999)). These results strongly support the model in FIGS. 4A and 4B and indicate that the yeast pre-vacuolar compartment can be used to identify the elusive plant transporters involved intracellular sodium detoxification.

The model set forth in FIGS. 4A and 4B is entirely consistent with the physiological data on the role of the vacuole in cation detoxification in higher plants. Yeast and plant cells share pathways and signals for the trafficking of vesicles from the Golgi network to the vacuole (Neuhaus, J. M., et al., *Plant Mol. Biol.*, 38:127-144 (1998); (Paris, N., et al., *Plant Physiol.*, 115:29-39 (1997); Sato, M. H., et al., *J. Biol. Chem.*, 272:24530-24535 (1997); Vitale, A. V., et al., *Trends Plant Sci.*, 4:148-154 (1999)). Studies were therefore undertaken in yeast to identify the role of the vacuole in cation detoxification in higher plants.

Studies of Cation Sequestration Mechanism in Yeast

Example 1

Functionality of AtNhx1 and Avp1 in Yeast Strains

To test the sequestration models set forth in FIGS. 4A and 4B, mutant yeast strains (ena1) lacking the plasma membrane sodium efflux pump, which therefore must rely on the internal detoxification system in order to grow on high salt, were constructed. The sequestration model (Nass, R. and Rao, R., *J. Biol. Chem.*, 273:21054-21060 (1998) and, Gaxiola, R. A., et al., *Proc. Natl. Acad. Sci. USA*, 95:4046-4050 (1998)) of FIGS. 4A and 4B predicts that the ena1 strain would become salt tolerant if one could enhance the availability of protons in the postulated endosomal compartment, that is with increased influx of protons, cytoplasmic $Na^+$ would be sequestered via the Nhx1 exchanger.

The yeast vacuolar ATPase is a multisubunit protein, so it is difficult to increase its activity by overexpressing any one of its subunits. Instead the same effect was achieved by increasing the influx of protons by expressing the *A. thaliana* AVP1 gene in yeast. This gene encodes a single polypeptide that, when expressed in yeast, is capable of pumping protons into the lumen of the vacuole (Kim, E. J., et al., *Proc. Natl. Acad. Sci. USA*, 91:6128-6132 (1994)). To ensure maximum activity of this proton pump, the E229D gain-of-function mutant of the AVP1 gene (AVP1-D) that has enhanced $H^+$ pumping capability was expressed (Zhen, R. G., et al., *J. Biol. Chem.*, 272:22340-22348 (1997)). Intracellular sodium and potassium content was determined for mutant and wild-type cells after growth on SD-ura medium with high NaCl content.

Materials and Methods

Yeast Strains and Plasmids

Strains isogenic to W303 (ura3-1 can1-100 leu2-3, 112trp1-1 his3-11, (Gaxiola, R. A., et al., *EMBO J.,* 11:3157-3164 (1992)) were employed. Plasmids pRG52 (*gef1::HIS3) (Gaxiola, R. A., et al., *Proc. Natl. Acad. Sci. USA,* 95:4046-4050 (1998)) and pRG197 (*nhx1::HIS3) were used to construct the deletions of GEF1 and NHX1 genes, yielding strains RGY85 and RGY296, respectively. The ena1::HIS3 mutant was obtained from Fink Lab collection (L5709).

Method of Transformation

Transformation of yeast cells was performed by using the lithium acetate method (Gietz, D., et al., *Nucleic Acids Res.,* 20:1425 (1992)). Double mutants RGY324 (gef1::HIS3 ena1::HIS3), RGY326 (nhx1::HIS3 ena1::HIS3), and RGY343 (gef1::HIS3 nhx1::HIS3) were obtained by crossing the single-mutant strains. Double mutants were identified among the meiotic progeny by scoring for the phenotypes associated with each of the single mutants. Sporulation, tetrad dissection, and mating types were scored as described (Guthrie C. and Fink, G. R., Guide to Yeast Genetics and Molecular Biology (Academic, San Diego (1991)). Cells were grown in YPD (1% yeast/2% peptone/2% dextrose; DIFCO), YPGAL (1% yeast/2% peptone/2% galactose; DIFCO), SD (DIFCO; Synthetic medium with 2% Dextrose), or APG (APG is a synthetic minimal medium containing 10 mM arginine, 8 mM phosphoric acid, 2% glucose, 2 mM $MgSO_4$, 1 mM KCl, 0.2 mM $CaCl_2$, and trace minerals and vitamins) (Rodriguez-Navarro, A. and Ramos, J., J. Bacteriol., 159:940-945 (1984)). $MnCl_2$ (Sigma), tetramethylammonium chloride (Sigma), NaCl (Sigma), or hygromycin-B (Sigma were added as indicated.

Wild type, L5709 (ena1::HIS3), RGY324 (gef1::HIS3 ena1::HIS3), and RGY326 (nhx1::HIS3 ena1::HIS3) strains were transformed with pYES2 vector (Invitrogen) and plasmid pYES2-AVP1-E229D described in Zhen, R. G., et al., *J. Biol. Chem.,* 272:22340-22348 (1997). The strain RGY343 (gef1::HIS3 nhx1::HIS3), used for histochemical analysis, was transformed with pRG151 (GEF1-GFP) (Gaxiola, R. A., et al. *Proc. Natl. Acad. Sci. USA,* 95:4046-4050 (1998)) and with pRIN73 [NHX1-$(HA)_3$] (Nass, R., and Rao, R., *J. Biol. Chem.,* 273:21054-21060 (1998)).

Wild-type and RGY296 (nhx1::HIS3) strains were transformed with vector pAD4 (Ballester, R., et al., *Cell,* 59:681-686 (1989)). RGY296 (nhx1::HIS3) was transformed with pRG308 (ADH1::AtNHX1) (see Cloning of AtNHX1).

Determination of Intracellular Sodium and Potassium Content

Cells were grown overnight in SD-ura medium (DIFCO; synthetic medium with 2% dextrose without uracil). YPGAL (1% yeast extract/2% peptone/2% galactose; DIFCO) media was inoculated with the overnight stocks and grow to an $A_{600}$ of 0.6. At this OD, NaCl was added to a final concentration of 0.7 M. The cells were incubated for 6 h, harvested by centrifugation, washed two times with 1.1 M sorbitol and 20 mM $MgCl_2$, and entracted with water for 30 min at 95° C.

The amount of $Na^+$ and $K^+$ in cells was determined at the University of Georgia Chemical Analysis Laboratory by an Inductively Coupled Plasma-MS. Intracellular cation concentrations were estimated as described (Gaxiola, R. A., et al., *EMBO J.,* 11:3157-3164 (1992)) by using the intracellular water value calculated for cells grown in 1 M NaCl.

Immunofluorescence

The strain RGY343 (gef1::HIS3 nhx1::HIS3) was grown in SD-ura, -leu medium (DIFCO; synthetic medium with 2% dextrose without uracil and leucin) to mid-logarithmic phase, 0.1 mg/ml hygromycin B was added, and the culture was incubated for 1 h at 30° C. Cells were fixed with 3.7% formaldehyde (Sigma) for 45 min at room temperature without agitation. Spheroplast formation, permeablization, washing, and antibody incubation was performed as described (Pringle, J., et al., in *Immunofluorescence Methods for Yeast,* eds. Guthrie, C. And Fink, G. F. (Academic, Sand Diego), Vol. 194 pp. 565-602 (1991)). MAB HA11 used as first antibody was from Babco (Richmond, Calif.). Cy3-conjugated goat anti-mouse IgG was from Jackson Immunoresearch. 4',6-Diamidino-2-phenylin-dole (Sigma) was added to mounting medium to stain mitochondrial and nuclear DNA.

Subcellular Fractionation and Western Analysis

The strain RGY343 (gef1::HIS3 nhx1::HIS3) was grown in APG medium (pH 7.0), and lysates fractionated on a 10-step sucrose density gradient as described (Nass, R. and Rao, R., J. Biol. Chem., 273:21054-21060 (1998)). Aliquots of individual fractions (100 μg) were subjected to SDS/PAGE and transferred to nitrocellulose as described (Nass, R. and Rao, R., J. Biol. Chem., 273:21054-21060 (1998)). Western blots were probed with monoclonal anti-GFP (green fluorescent protein) antibody (1:10,000 dilution; CLONTECH), anti-hemagglutinin antibody (1:10,000 dilution: Boehringer Mannheim), and peroxidase-coupled goat anti-mouse antibody (1:5,000;) and developed by using the ECL enhanced chemiluminescence system (Amersham Pharmacia).

Cloning of AtNHX1

AtNHX1 was cloned from a phage cDNA library of *A. thaliana* (Kieber, J. J., et al., *Cell,* 72:427-441 (1993)) (obtained from the *Arabidopsis* Biological Resource Center) by probing with an expressed sequence tag (Arabidopsis Biological Resources Center, DNA Stock Center) containing a partial clone. A full-length clone (2.1 kB) was ligated into vector pSK2 (STRATAGENE) at the NotI sit, generating plasmid pRG293. The AtNHX1 ORF was amplified via PCR by using pRG293 as template and GGCCCGGGATGGATTCTCTAGTGTCGAAACTGCCTTCG (SEQ ID NO: 1) (italicized bases correspond to nucleotides 1-30 of the ORF) and T7 oligonucleotides. The PCR product was then digested with XbaI and SalI and ligated into pAD4 vector generating plasmid pRG308. The AtNHX1 ORF was sequenced to verify the fidelity of the PCR product. The full-length sequence is longer than the ORF reported by the: *Arabidopsis* Genome Initiative (A TM021B04.4), and has been deposited in GenBank (accession no. AF106324).

Cloning of AVP1-D

Vector pYES2 (Invitrogen) was introduced into wild-type, ena1, ena1 nhx1, and ena1 gef1 mutants. Plasmid pYes2-AVP1-D (Zhen, R. G., et al., *J. Biol. Chem.,* 272:22340-22348 (1997)) was introduced into ena1, ena1 nhx1, and ena1 gef1 mutants. Five-fold serial dilutions (starting at $10^5$ cells) of each strain were plated on YPGAL (1% yeast extract/2% peptone/2% galactose) with or without 0.5 M NaCl and incubated at 30° C. for 2 days. Exponentially growing cells (wild-type and ena1 transformed with pYES2 vector and ena1, ena1 nhx1, and ena1 gef1 mutants carrying pYes2-AVP1-D) were exposed to 0.7M NaCl for 6 hours. Total cell extracts were prepared, and $Na^+$ and $K^+$ concentrations were determined.

Results

The ena1 mutant of the above construct lacks the plasma membrane sodium efflux pump and therefore must rely on the internal detoxification system to overcome sodium toxicity. Growth of the ena1 strain is sensitive to low concentrations of sodium (200 mM), concentrations that do not inhibit the growth of wild-type strains. Overexpression of AVP1-D restored salt tolerance to salt-sensitive ena1 mutants. The restoration of salt tolerance to an ena1 strain by AVP1-D requires functional NHX1 and GEF1 genes: ena1nhx1 AVP1-D and ena1 gef1 AVP1-D strains are salt sensitive.

Figure 5A:
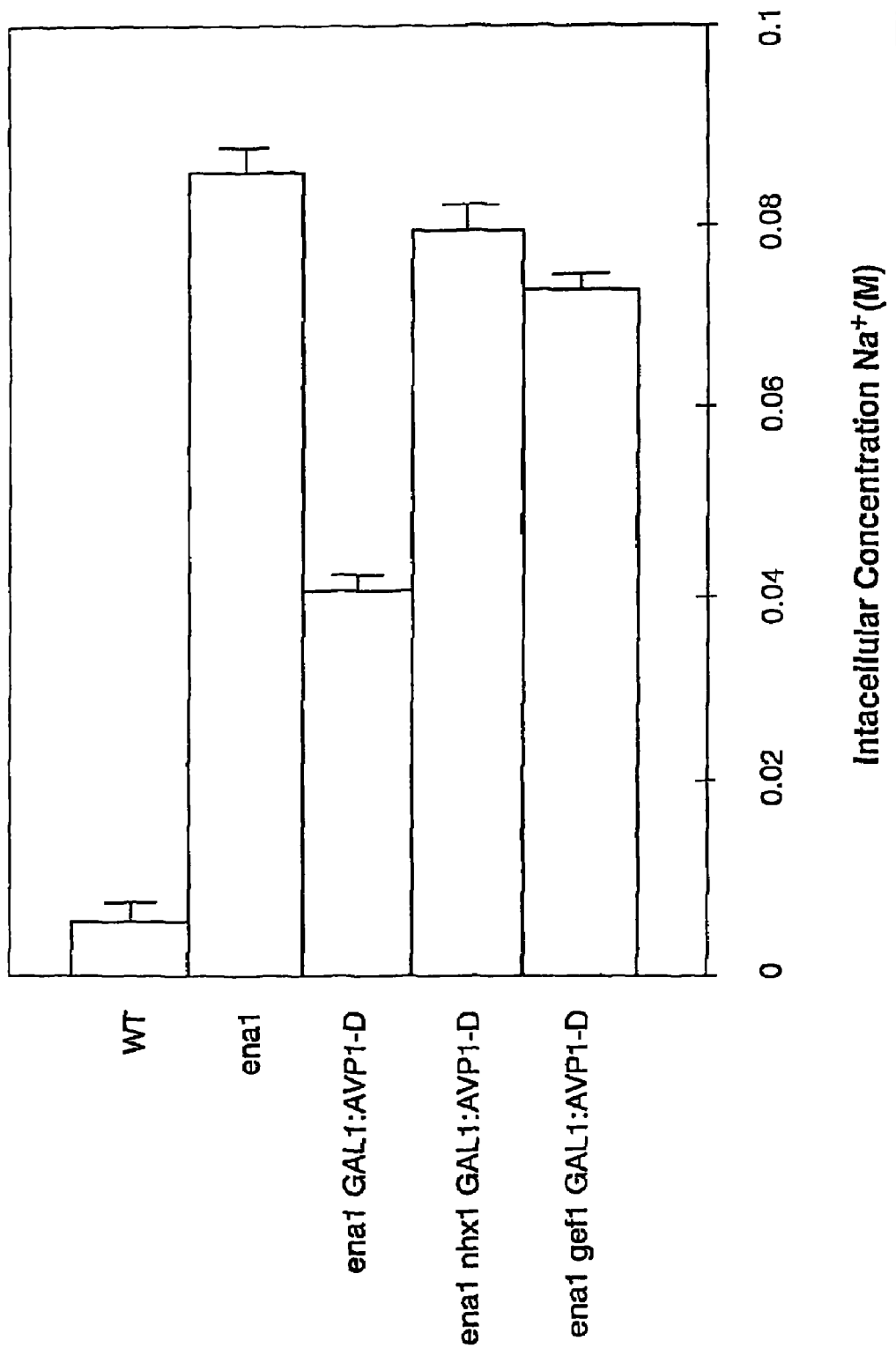
FIG. 5A and FIG. 5B are bar graphs showing the intracellular $Na^+$ and $K^+$ contents of wild-type yeast strains and of yeast strains carrying various mutations affecting sodium tolerance wherein the values are the mean of two determinations, and the bars represent the standard deviations.
Figure 5B:
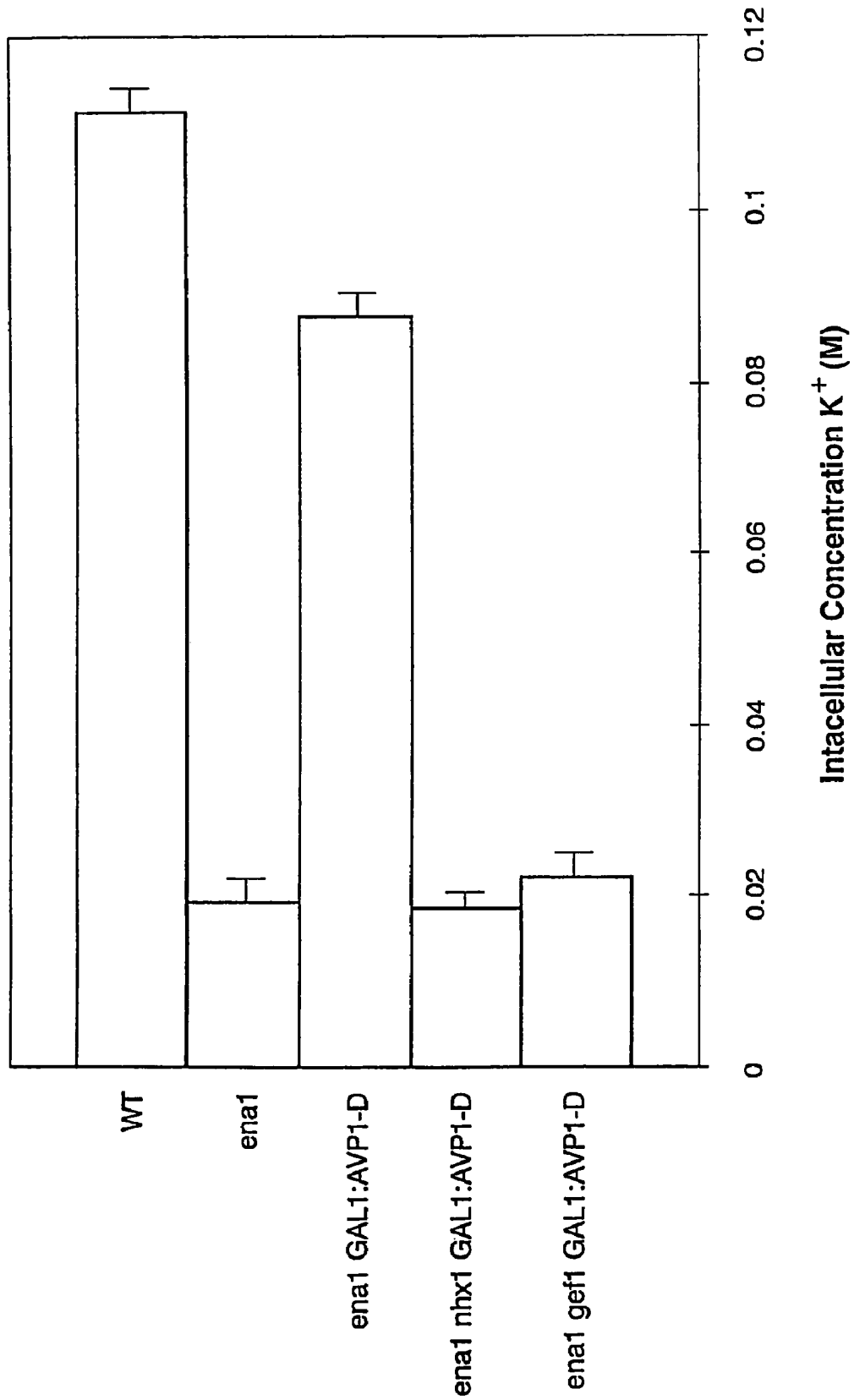

FIG. 5A and FIG. 5B are bar graphs showing the intracellular Na$^+$ and K$^+$ contents of wild-type yeast strains and of yeast strains carrying various mutations affecting sodium tolerance wherein the values are the mean of two determinations, and the bars represent the standard deviations. The intracellular Na$^+$ and K$^+$ contents of wild-type strains and of strains carrying various mutations affecting sodium tolerance were determined after 6 h of exposure to media supplemented with 0.7 M NaCl. The intracellular Na$^+$ content in the ena1 mutant was seen to be 8-fold higher than in the wild-type strain. There was seen to be a consistent reduction in total cell Na$^+$ in the ena1 AVP-D strain. The reason for this reduction is unknown. The ena1 AVP-D strain was found to be salt-resistant, even though its intracellular Na$^+$ content was 4-fold higher than that of the wild type. In ena1 AVP1-D strains lacking either gef1 or nhx1 (i.e., ena1 gef1 or ena1 nhx1), the Na$^+$ content was not reduced to the extent that it was in the GEF1 NHX1 strain. Taken together, the genetic and physiological data are consistent with the model that Nhx1, Gef1 and Avp1 cooperate to sequester sodium internally. As can be seen in the graphs, the *Arabidopsis* Vacuolar H$^+$-Pyrophosphatase (Avp1) was evidenced to confer salt tolerance to yeast ena1 mutants.

The intracellular K$^+$ content was found to correlate with salt tolerance and is inversely correlated with the Na$^+$ content of the strains (FIG. 4B). The wild-type K$^+$ concentration was at 100 mM, but was reduced to 20 mM in the ena1 mutant. Interestingly, in an ena1 strain that overexpresses the AVP1-D gene, the intracellular concentration of K$^+$ was restored almost to wild-type levels (FIG. 4B). However, AVP1-D overexpression failed to restore wild-type levels of intracellular potassium unless both NHx1 and GEF1 were functional (See, the double mutants ena1 nhx1 or ena1 gef1 in FIG. 4B).

As shown herein, intracellular Na$^+$ detoxification in yeast requires functional Na$^+$/H$^+$ exchanger (Nhx1) and chloride channel (Gef1), and they co-localize to a pre-vacuolar compartment (Gaxiola, R. A., et al., *Proc. Natl. Acad. Sci. USA*, 96:1480-1485 (1999)). When the *Arabidopsis thaliana* homologue of the yeast NHX1 gene (AtNHX1) was cloned and its function in the nhx 1 yeast mutant tested, the AtNHX1 gene was found to be able to suppress partially the cation sensitivity phenotypes of nhx1 mutants.

Example 2

Functionality of, and Co-Localization of Gef1p and Nhx1p in Yeast Strains

The NHX1 and GEF1 genes, which have been identified as important in sodium detoxification, are also required for the detoxification of other cations. An investigation was made with respect to the viability of yeast strains mutant with respect to gef1 and nhx 1 (ena1) in the presence of toxic cations, in light of the model set forth in FIGS. 4A and 4B.

The sequestration model postulates not only a functional connection between the anion channel Gef1 and sodium exchanger Nhx1 but also predicts that these two proteins co-localize within a common compartment. Because previous studies indicated that Nhx1 localizes to a pre-vacuolar compartment (Nass, R. and Rao, R., J. Biol. Chem., 273: 21054-21060 (1998)), experiments were also performed to determine whether Gef1 and Nhx1 proteins co-localize to this compartment.
Materials and Methods The strain RGY419 (gef1 nhx 1) was transformed with plasmids pRG151; GEF1-GFP and pRIN73; NHX1-(HA)$_3$. Transformants were grown in SD (DIFCO; synthetic medium with 2% dextrose). To determine the sensitivity of such transformants to toxic cations, five-fold serial dilutions (starting at 10$^5$ cells) of the indicated strains were grown at 30° C. for 2 days on YPD (1% yeast extract/2% peptone/2% dextrose) with the addition of either 3 mM MnCl$_2$, 0.45 M tetramethylammonium (TMA), or 0.05 mg/ml hygromycin B (HYG) as indicated.

Two studies were undertaken to demonstrate co-localization of Gef1p and Nhx1p.

Distribution of fluorescence and immunodetection of subcellular fractions in gef1 nhx1 cells transformed with two constructs: a GEF1-GFP fusion and a NHX1-(HA)$_3$-tagged fusion were determined. When the cells reached OD$_{600}$=0.5, hygromycin B (Sigma) was added to a final concentration of 0.1 mg/ml and the cells were incubated for 40 min at 30° C. Cells were fixed and stained with antibodies to HA epitope and 4',6-diamidino-2-phenylindole (DAPI). Cells were viewed by charge-coupled device microscopy and optically sectioned by using a deconvolution algorithm (Scanalytics, Billerica, Mass.) (Kennedy, B. K., et al, Cell, 89:381-391 (1997)); (Bar=1·m.).

The migration properties of the Gef1p and Nhx1p in sucrose gradients was also determined to provide evidence of co-localization of Nhx1 (HA)$_3$ and GEF1-GFP. The strain RGY419 (gef1 nhx 1) was transformed with plasmids pRG151; GEF1-GFP and pRIN73; NHX1-(HA)$_3$ and grown in APG medium (Rodriguez-Navarro, A. and Rea, P. A., J. Biol. Chem., 159:940-945 (1984)). Such was converted to spheroplasts, lysed, and fractionated on a 10-step sucrose gradient (18-54%) as described (Sorin, A., et al., *J. Biol. Chem.*, 272:9895-9901 (1997) and Antebi, A. and Fink, G. R., *Mol. Biol. Cell*, 3:633-654 (1992)). Western blots showed the distribution of Gef1-GFP and Nhx1-HA.
Results Gef1 mutants were found to be sensitive to 3 mM MnCl$_2$, 0.45 M tetramethylammonium chloride and to 0.05 μg/ml hygromycin-B. The nhx1 mutant was also found to be sensitive to tetramethylammonium chloride and hygromycin. The extreme sensitivity of the nhx-1 mutant to hygromycin may provide an important tool for assaying nhx1 function.

It was found that hemagglutinin (HA)-tagged Nhx1 and Gef1-GFP fusion protein co-localize as shown via epifluorescence deconvolution microscope. Persistence of signal coincidence on 90° rotation of the image further supports co-localization of the two transporter proteins in these cells. The co-localization of Nhx1 (HA)$_3$ and GEF1-GFP is also supported by the co-migration of the two proteins in sucrose density gradients of membrane preparations obtained from cells expressing the tagged proteins. The sedimentation behavior of the membrane fraction containing both proteins is consistent with that of a pre-vacuolar compartment (Nass, R. and Rao, R., J. Biol. Chem., 273:21054-21060 (1998)). Gef1-GFP (but not Nhx1) is also present in Golgi fractions, consistent with previous studies (Gaxiola, R. A., et al., *Proc. Natl. Acad. Sci. USA*, 95:4046-4050 (1998), Schwappach, B., et al., *J. Biol. Chem.*, 273:15110-15118 (1998)).

Example 3

Capacity of *A. thaliana* Homolog of NHX1 to Suppress Hygromycin Sensitivity of Mutant Yeast The yeast strain described herein provides an important tool for identifying genes that mediate salt tolerance in other organisms. To test the utility of this system, a sequence from *Arabidopsis* (See Materials and Methods) with very high homology to the *S. cerevisiae* NHX1 ORF was identified and used an expressed sequence tag (see Materials and Methods) to obtain a full-length clone of this *Arabidopsis* gene. An alignment of the amino acid sequences of Nhx1 homologues from *Arabidopsis* (AtNhx1), human (HsNhe6), and yeast (ScNhx1) reveals segments of amino acid identity and similarity within predicted transmembrane domains (FIGS. 6A-C). However, it is important to note that despite these relationships, neither the C-terminal regions of AtNhx1 and ScNhx1 show a high degree of homology (FIGS. 6A-C).

A characteristic of mammalian $Na^+/H^+$ antiporters is their inhibition by amiloride. A putative amiloride binding site ($^{163}$DVFFLFLLPP$^{173}$) (SEQ ID NO: 4) has been defined via point mutants in the human NHE1 antiporter gene (Counillon, L., et al., *Proc. Natl. Acad. Sci. USA*, 90:4508-4512 (1993)). AtNhx1, HsNhe-6 and ScNhx1 have an almost identical sequence (FIG. 6). However, attempts to inhibit the activity of either Nhx1 or AtNhx1 in yeast cultures with amiloride were unsuccessful.

The extreme sensitivity of yeast nhx 1 mutants to hygromycin permitted the testing of whether the cloned *Arabidopsis* AtNHX1 ORF could provide $Na^+/H^+$ exchange function in yeast. Vector pAD4 (Ballester, R., et al., *Cell*, 59:681-686 (1989) was introduced into wild-type and nhx1 strains. Plasmid pRG308; ADH; AtNHX1 was introduced into nhx1 mutants as indicated. Five-fold serial dilutions (starting at $10^5$ cells) of the indicated strains were grown at 30° C. for 2 days on YPD (−) or on YPD supplemented with 0.05 mg/ml hygromycin (+). Serial dilutions of the same strains were grown on APG medium (see Materials and Methods) (−) or on APG supplemented with 0.4 M NaCl (Rodriguez-Navarro, A. and Ramos, J., *J. Bacteriol.*, 159:940-945 (1984).

The At NHX1 gene is capable of suppressing the hygromycin sensitivity of the nhx1 mutant. The AtNHX1 gene also suppressed the NaCl sensitivity of nhx1 mutant but only under conditions in which the $K^+$ availability was reduced. However, AtNHX1 was not capable of rescuing the $Na^+$-sensitive growth phenotype of the double mutant ena1 nhx1 overexpressing the AVP1-D gene.

Example 4

Generation of Gain-of-Function Yeast AtNHX Mutants Materials and Methods

Gain of function mutants of the AtNHX that enhance salt tolerance may be generated in the ena1 yeast by mutagenizing the cloned gene to make a mutant library. This library may be used to transform the salt sensitive yeast mutant ena1 and clones with an enhanced salt tolerant phenotype.

Other genes that show similarity to the AtNHX1 gene, as reported by the *Arabidopsis* Genome Initiative (AGI), may also be expressed in the mutant yeast to form gain-of-function mutants. It is believed that some of these AtNHX1 homologues are plasma membrane transporters, so their function in yeast are frequently pH dependent, requiring precise composition and pH of the medium used for screening for success. Identification of plasma membrane transporters helps to engineer plants with an enhanced salt tolerance due to a reduced sodium uptake. In addition, plant cDNA expression libraries in yeast may be used to identify other families of transporters involved in NaCl detoxification.

To generate gain of function mutants of the AtNHX a method for introducing random mutations developed by Stratgene (Epicurian Coli XL1-Red competent Cells Cat#200129) may be used. The method involves the propagation of a cloned gene into a strain deficient in the three primary DNA repair pathways. The random mutation rate in this strain is about 5000-fold higher than that of wild-type. A library of the mutated AtNHX gene may be transformed into the ena1 yeast mutant and screened for salt tolerance. Yeast transformation was performed as described by Schiestl and coworkers (Gietz, D., et al., *Nucl. Acid Res.* 20:1425 (1992), incorporated by reference in its entirety herein). An alternative to the XL1-Red random mutagenesis strategy is a PCR approach described by Fink and coworkers (Madhani, H. D., et al., *Cell*, 91:673-684 (1997)).

To test AtNHX1 homologues the same strains and conditions may be as described in Gaxiola, R. A., et al., *Proc. Natl. Acad. Sci. USA*, 96:1480-1485 (1999). However, others may be employed. When dealing with plasma-membrane ATNHX1 homologues pH conditions of the assay media may be crucial.

Results

The overexpression of the *A. Thaliana* gain-of-function mutant gene AVP1-D increases the intracellular detoxification capability in yeast (Gaxiola, R. A., et al., *Proc. Natl. Acad. Sci. USA*, 96:1480-1485 (1999)). It is hypothesized (although the inventors are not limited by such hypothesis) that the latter is due to an increased influx of $H^+$ into the vacuolar compartment thereby improving $Na^+$ sequestration via the Nhx1 exchanger.

Conclusions from Yeast Cation Sequestration Studies

The yeast studies described above provide evidence for the importance of the pre-vacuolar pH for intracellular $Na^+$ sequestration in yeast. Overexpression of the plant $H^+$-pyrophosphatase (Avp1) confers salt tolerance to yeast only in those strains containing a functional chloride channel (Gef1) and the $Na^+/H^+$ exchanger (Nhx1).

These data support a model in which the Nhx1 $Na^+/H^+$ exchanger acts in concert with the vacuolar ATPase and the GEF1 anion channel to sequester cations in a pre-vacuolar compartment. Several studies suggest that the pre-vacuolar compartment may be derived both from the plasma membrane and the late Golgi. These vesicles are likely involved in the assembly of the vacuole or delivery of cargo to this organelle. It is reasonable to expect that these pre-vacuolar vesicles detoxify cations by sequestration, thereby lowering their concentrations in the cytoplasm and in other organelles.

The yeast system described herein permits the functional assessment of diverse heterologous proteins in salt tolerance: chloride channels, $H^+$ pumps, and $Na^+/H^+$ exchangers and other cation/$H^+$ exchangers or cation/bicarbonate symporters. The system is robust and flexible. The function of the *Arabidopsis* chloride channels (Gaxiola, R. A., et al, Proc. Natl. Acad. Sci. USA, 95:4046-4050 (1998), Hechenberger, M., et al., *J. Biol. Chem.*, 271:33632-33638 (1996)), $H^+$ pump, and $Na^+$ exchanger can be assayed in the corresponding yeast mutant. Despite the inability of At NHX1 to suppress all the phenotypes of the yeast nhx1 mutant, the fact that it suppresses some phenotypes, coupled with the DNA homology between AtNHX1 and yeast NHX1, indicates that the plant gene carries out a similar function to that of the yeast homologue. The observation that the AtNHX1 gene suppresses the sensitivity of the nhx1 mutant to hygromycin but provides only a weak $Na^+$ detoxification phenotype could be a consequence either of differential regulation of the transporters in the two organisms or of distinct cation transport selectivities.

The regulation of AtNHX1 by salt and the ability of the plant gene to suppress the yeast nhx1 mutant suggest that the mechanism by which cations are detoxified in yeast and plants may be similar. Indeed, previous work suggested that vacuolar sodium accumulation in salt-tolerant plants may be mediated by a tonoplast $Na^+/H^+$ antiporter that utilizes the proton-motive force generated by the vacuolar H$^+$-ATPase (V-ATPase) and/or H$^+$-translocating pyrophosphatase (V-Ppase; refs. Barkla, B. J., et al., *Symp. Soc. Exp. Biol.*, 48:141-153 (1994), Zhen, R. G., et al., The Molecular and Biochemical Basis of Pyrophosphate-Energized Proton Translocation at the Vacuolar Membrane (Academic, San Diego), Kirsh, M, et al., *Plant Mol. Biol.*, 32:543-547 (1996)).

The finding described herein that both gef1 and nhx1 mutants are hypersensitive to hygromycin indicate that the level of resistance to hygromycin depends on the function of the vacuolar and pre-vacuolar organelles. Yeast mutants impaired in K$^+$ uptake (trk1) are hypersensitive to hygromycin (Madrid, R., et al., *J. Biol. Chem.*, 273:14838-14844 (1998)); reduced K$^+$ uptake hyperpolarizes the plasma membrane potential and drives the uptake of alkali cations such as hygromycin. Mutations that reduce the H$^+$ pumping activity of the plasma membrane H$^+$-ATPase, Pmal, depolarize the plasma membrane potential and confer resistance to hygromycin (McCusker, J. H., et al., *Mol. Cell. Biol.*, 7:4082-4088 (1987)). Thus, mutants such as gef1 or nhx1 that affect the pH or membrane potential of the vacuolar and pre-vacuolar compartments may be expected to affect hygromycin compartmentation.

Transgenic Plants with Unregulated Vacuolar H$^+$-Translocating Pump Activity

Further support for the role of the *Arabidopsis* AtNHX1 gene in salt homeostasis is provided by the observation that its expression is induced in salt-stressed plants (Gaxiola, R. A., et al., *Proc. Natl. Acad. Sci. USA*, 96:1480-1485 (1999)). *Arabidopsis thaliana*, in particular, has been used as a host model plant; to demonstrate that overexpression of these genes results in salt tolerance in the plant. A recent report shows that the overexpression of AtNHX1 gene in transgenic *Arabidopsis thaliana* promotes sustained growth in soil watered with 200 mM NaCl plus 1/8 M.S. salts under short-day cycle conditions (Apse, M., et al., *Science*, 285:1256-1258 (1999)). It is worth noting that every addition of 1/8 M.S. salts provides 2.5 mM potassium reducing the stringency of the NaCl stress, and that a short-day cycle reduces oxidative stress.

Example 5

Enhanced Expression of AtNHX1 Gene in Salt-Stressed Plants Materials and Methods

*A. thaliana* plants (ecotype Columbia) were grown aseptically on unsupplemented plant nutrient agar without sucrose (Haughn, G. W. and Somerville, C., Mol. Gen. Genet., 204: 430-434 (1986)) for 15 days at 19° C. and under continuous illumination. NaCl or KCl was added to a final concentration of 250 mM, and the plants were incubated for 6 h. Total RNA from tissue of salt-treated and untreated plants was isolated (Niyogi, K. K. and Fink, G. R., Plant Cell, 4:721-733 (1992)), HYBOND-N (Amersham) membranes were hybridized with a $^{32}$P-Labeled DNA probe from plasmid pRG308. Hybridization was performed at 65° C. overnight. Washes were performed at 65° C. with 0.2% standard saline citrate (SSC)/0.1% SDS (Ausebel, F., et al., *Curr. Protocols in Mol. Biol.* (Wiley, N.Y.) (1988)). 18S probe was used as loading control (Unified, I., et al., *Nucleic Acids Res.*, 17:7513 (1989)). MACBAS 2.4 program was used to quantify the relative amount of RNA.

Results

The NaCl stress increased AtNHX1 mRNA levels 4.2-fold, whereas KCl promoted only a 2.8-fold increase. This increase in mRNA level produced by sodium resembles that described for the yeast NHX1 gene (Nass, R. and Rao, R., J. Biol. Chem., 273:21054-21060 (1998)). RNA tissue blot hybridized with AtNHX1. Ten micrograms of total RNA from 15-day old plants exposed to 250 mM NaCl or KCl for 6 h and a control grown without salt was subjected to electrophoresis on a denaturing formaldehyde gel. The blot was hybridized with a probe internal to AtNHX1 ORF. An 18S ribosomal probe was used as a loading control.

Example 6

Salt Tolerance of Transgenic Plants Overexpressing AtNHX1

Transgenic plants that overexpress the AtNHX1 show sustained growth in soil watered with 200 mM sodium chloride. (Apsem M., et al., *Science*, 285:1256-1258 (1999).

Example 7

Salt Tolerance of Transgenic Plants Overexpressing 35SAVP1

Materials and Method

A transgenic *Arabidopsis thaliana* plant was engineered to overexpress the AVP1 wild-type gene using the double tandem enhancer of the 35S promoter (Topfer, R., et al., *Nucl. Acid Res.*, 15:5890 (1987)). AVP1 encodes the pyrophosphate-energized vacuolar membrane proton pump from *Arabidopsis* (Zhen, R. G., et al., *J. Biol. Chem.*, 272:22340-22348 (1997)). Previous investigations suggest that the AVP1 gene is present in a single copy in the genome of *Arabidopsis* (Kim, Y., et al., *Plant Physiol.*, 106:375-382 (1994)), however, a sequence homologous, but not identical, to AVP1 on chromosome one has been tentatively designated as ORF F9K20.2 on BAC F9K20 by the *Arabidopsis* Genome Initiative (AGI).

Transgenic plants that overexpress AVP1 were generated using *Agrobacterium*-mediated plant transformation. The transgenic AVP1 was expressed using a double tandem enhancer of the 35S promoter of CaMV (Topfer, R., et al., *Nucl. Acid Res.*, 15:5890 (1987)). 15 wild-type plants and 15 35SAVP1 transgenics were grown on a 24 hours-day cycle for 16 days. During this period plants were watered every 4 days with a diluted nutrient solution (1/8 M.S. salts). 200 mM NaCl was added to the watering solution at day 17 and at day 27 plants were watered with nutrient solution containing 250 mM NaCl. Plants were photographed 10 days after the last NaCl treatment. Identical conditions and treatment as described in Example 6 were used.

Results

Five different lines of 35SAVP1 plants showed an enhanced salt tolerance as compared to wild-type plants in the T2 stage. However, the most dramatic phenotype was apparent in the homozygous T3 plants. These transgenic plants are larger than wild-type plants. Furthermore, homozygous 35SAVP1 plants showed sustained growth in the presence of 250 mM NaCl plus 1/8 M.S. salts when grown in a 24 hours light regimen. When 35SAVP1 plants were grown under short-day cycle conditions (12 hour day/light cycle) sustained growth in the presence of 300 mM NaCl plus 1/8 M.S. salts was observed.

Example 8

Growth of Wild Type Plants and 35SAVP1 Transgenic Plants in Hydroponic Solution

The reduced availability of fresh water for standard agriculture may force the use of alternative agricultural arts. It is conceivable that with salt tolerant crops the use of hydroponics with seawater will create a new era in crop production. Hydroponic culture has been reported to increase plant growth and provide stress-free root and shoot material (Gibeaut, D. M., et al., *Plant Physiol*, 317-319 (1997)). Another important advantage of hydroponic culture is that it allows one to alter the ionic composition in a more accurate manner than in soil. These advantages could be important for the physiological studies of salt stress.

Conditions for hydroponics culture of *Arabidopsis* plants were established and their performance in increasing concentrations of NaCl in their media were tested.

Materials and Methods

In one test, wild type and 35SAVP1 transgenic plants were hydroponically grown. Wild type and 35SAVP1 transgenic plants were grown in solution culture on a 12 hour light cycle for 65 days.

In another test, wild type and 35SAVP1 transgenic plants were grown in solution culture on a 12 hours light cycle for 20 days. Starting at day 21, NaCl concentration was increased in a stepwise fashion by 50 mM increments every 4 days. Plants were photographed after 4 days in the presence of 200 mM NaCl.

And yet in another hydroponic test, transgenic plants were challenged with a commercial seawater formula that contains the complete ionic composition present in the oceans. 35SAVP1, 35SAtNHX1 single and double transgenics were grown together with wildtype *Arabidopsis thaliana* plants under hydroponic conditions for four weeks in a short day illumination cycle (Gibeaut, D. M., et al., *Plant Physiol.*, 317-319 (1997)). Then every four days an equivalent to 50 mM NaCl of TROPIC MARIN sea salt is added. This artificial sea water mix includes all of the other major and trace elements present in real sea water. Growth was monitored and physiological parameters, such as sodium content and distribution may be monitored.

Results

When wild type and 35SAVP1 transgenic plants were grown hydroponically the size differences in root, leaves and stems among wild type and 35SAVP1 transgenic plants were found to be dramatic, with 35SAVP1 transgenic plant parts being much larger.

When NaCl concentration were increased stepwise by 50 mM every 4 days (Apse, M., et al., *Science*, 285:1256-1258 (1999), 35SAVP1 transgenic plants appeared healthy in the presence of 200 mM NaCl while wild type controls showed severe deleterious effects in their leaves and stems.

35SAVP1, 35SAtNHX1 single and double transgenics that were grown together with wildtype *Arabidopsis thaliana* plants under hydroponic conditions for four weeks in a short day illumination cycle (Gibeaut, D. M., et al., *Plant Physiol.*, 317-319 (1997)) and then challenged every four days with an equivalent to 50 mM NaCl of TROPIC MARIN sea salt were found to grow in the sea salt solution better than wildtype *Arabidopsis thaliana* plants.

Example 9

Effect of Overexpression of *Arabidopsis thaliana* Proton Transporters in Tomato Plants The effects of the overexpression of these *Arabidopsis thaliana* proton transporters (AVP1 and AtNHX1) in a more agriculturally important plant, the tomato plant, may be examined. It is believed that increasing the salt-tolerance of tomato plants will likely have important economic repercussions.

The tomato homologues of AVP1 and AtNHX1 may be isolated and the corresponding chimeras to overexpress them may be constructed (Bidone, S., et al., *Eur. J. Biochem.*, 253: 20-26 (1998); Burbidge, A., et al., *J. Exper. Botany*, 48:2111-2112. (1997)). The genes may be introduced via *Agrobacterium*-mediated infection of calli. Tissue culture methods may be used to regenerate transformed plants. The plants may be assayed for salt tolerance as well as physiological parameters, such as sodium content and distribution.

Tomato transformation with 35S AVP1 and with 35S AtNHX1 constructs may be performed as described by McCormick (McCormick, S., Transformation of tomato with *Agrobacterium tumefaciens*. In: Plant Tissue Culture Manual, pp. 1-9, Lindsey, K. (ed.), Kluwer Academic Publishers, Dordrecht, The Netherlands (1991)). T0 and T1 transgenics may be analyzed by polymerase chain reaction and DNA gel blotting for the presence and copy number of AVP1 and ATNHX1 transgenes. Heterozygous and homozygous plants may be identified after segregation analysis of each transgenic within T1 seeds. Homozygous plants may be assayed for salt tolerance and as well as physiological parameters, such as sodium content and distribution. Degenerated oligos based on conserved sequences present in AVP1 and AtNHX1 homologues may be designed. These degenerated primers may be used in RT-PCR reactions with cDNAs made from poly(A)+RNA from tomato. The resulting PCR fragments may be used as probes to isolate the full length cDNA clones from commercial libraries (i.e. STRATAGENE Cat#936004). A similar strategy was described by Caboche and coworkers (Quesada, A., et al., *Plant Mol. Biol.*, 34:265-274 (1997)).

Results

Positive test results would indicate that the sequestration model described herein is also applicable to an important crop.

Figure 7A:
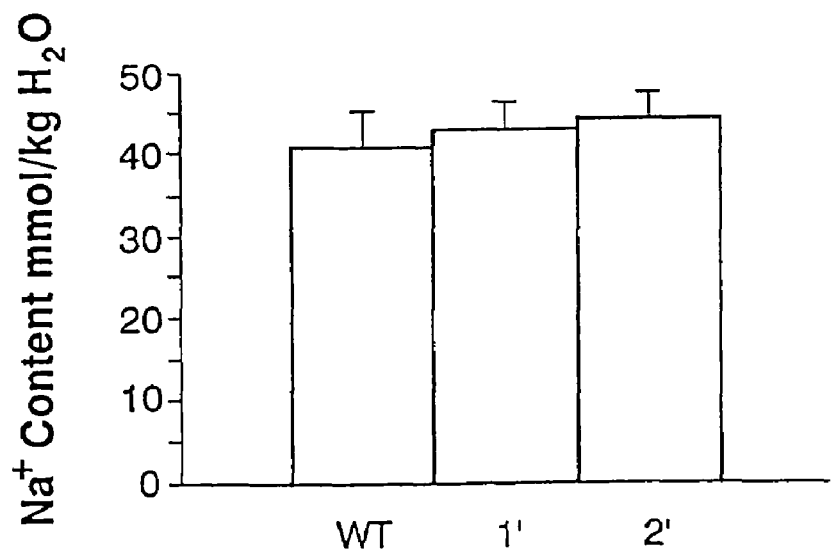
FIG. 7A is a bar graph of $Na^+$ content of wild-type plants (WT) versus representative transgenic plants overexpressing AVP-1 (1' and 2') grown in salty soil.
Figure 7B:
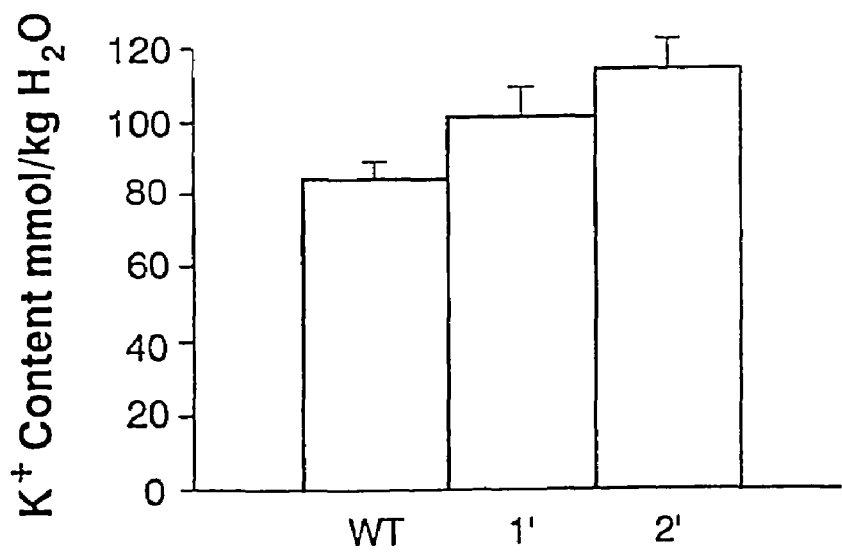
FIG. 7B is a bar graph of $K^+$ content of wild-type plants (WT) versus representative transgenic plants overexpressing AVP-1 (1' and 2') grown in salty soil.

FIG. 7 is a graph of $Na^+$ and $K^+$ content of wild-type plants (WT) versus representative transgenic plants overexpressing AVP-1 (1' and 2') grown in salty soil. Five wild-type plants (WT) and two AVP-1 overexpressing transgenic lines (1' and 2') were grown on soil in a 10 hour light/dark cycle. Plants were watered with a diluted nutrient solution (1/8 MS salts) for six weeks and subsequently watered with a diluted nutrient solution supplemented with NaCl. The concentration of NaCl began with 100 mM and was increased every four days by 50 mM. The photograph corresponds to plants at the tenth day in the presence of 300 mM NaCl. Parts of the plant above, ground were harvested after 24 hours in the presence of 200 mM NaCl and their fresh weigh measured. After 48 hours at 75° C., the dry weight was measured. $Na^+$ and $K^+$ content was determined by atomic absorption. Values in the graphs of FIG. 4 are the mean .+/−. SE (n=4). As can be seen from the graphs $Na^+$ and $K^+$ content in the transgenic lines (1' and 2') was significantly higher than that of wild-type counterparts.

Figure 8:
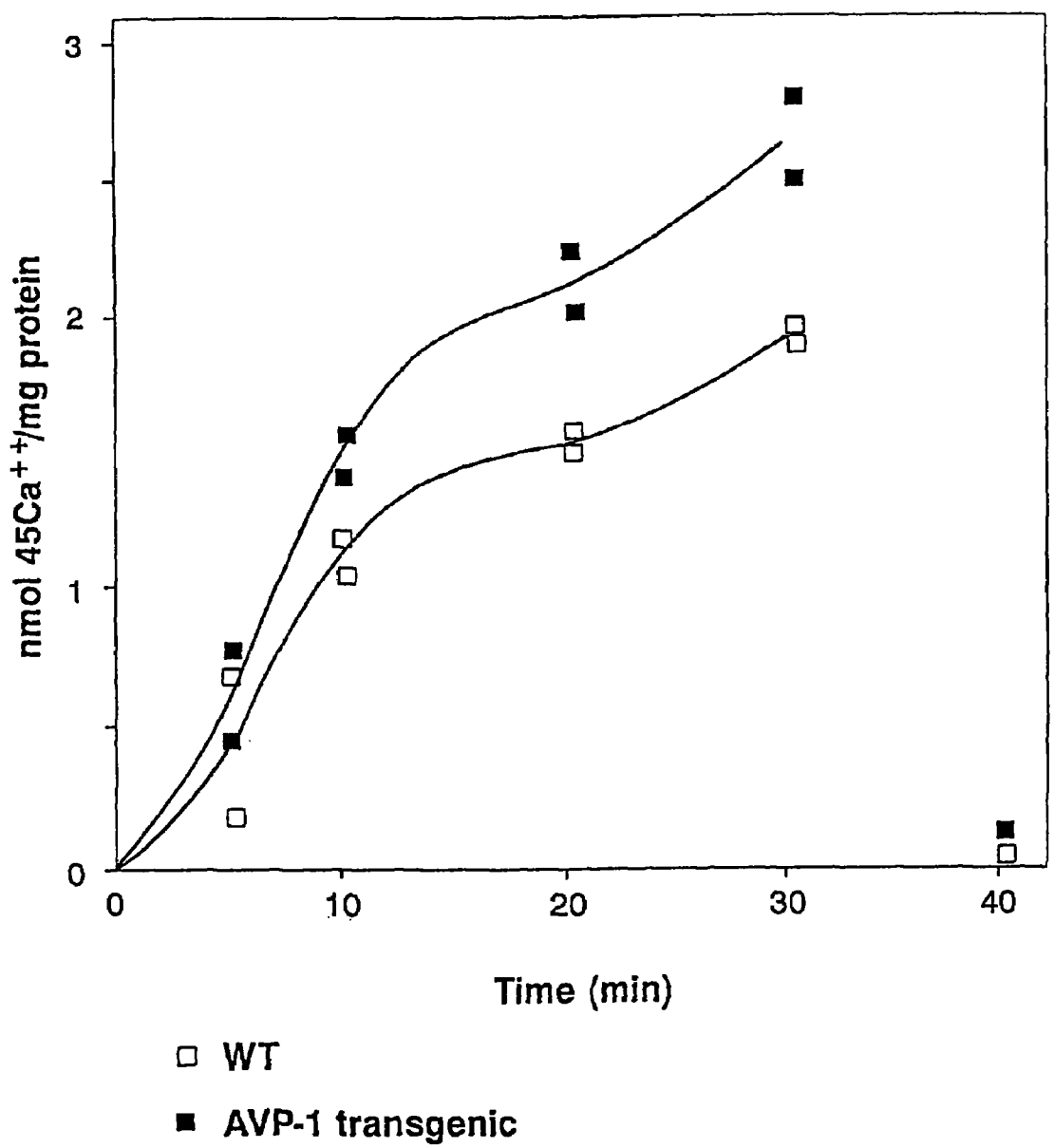
FIG. 8 is a graph of the uptake of calcium into the 35SAVP-1 transgenic vacuolar membrane vesicles (squares) of 2' of FIG. 3 versus calcium uptake into vesicles obtained from wild type (WT) of FIG. 3.

FIG. 8 is a graph of the uptake of calcium into the 35SAVP-1 transgenic vacuolar membrane vesicles (squares) of 2' of FIG. 4 versus calcium uptake into vesicles obtained from wild type (WT) of FIG. 4. Wild-type plants (open circles) and transgenic plants from line 2' of FIG. 4 were grown hydroponically for nine weeks on a 10 hour light cycle. Vacuolar membrane vesicles were added to buffer containing 250 mM sorbitol, 25 mM BTP-Hepes pH 8.0, 50 mM KCl, 1.5 nM $MgSO_4$ and 10 μM $Ca^{++}$. This mix was incubated at 20° C. for 10 minutes before adding 200 μM PPi to trigger the reaction. $Ca^{++}$ ionophore A23187 was added to a final concentration of 5 μg/ml to dissipate the $Ca^{++}$ gradient. Aliquot (200 μl) were filtered at the indicated times and washed with cold buffer as described (11). As is evidenced by the graphs, the transgenic plants from line 2' have greater calcium uptake than wild-type plants.

The above data is consistent with the hypothesis that transgenic plants overexpressing AVP-1 have an enhanced $H^+$ pumping capability at their tonoplast and that an enhanced $H^+$ supply results in greater ion accumulation in the vacuole through the action of $H^+$-driven ion transporters. To further support this theory, $Ca^{++}$ uptake capability of wild type and transgenic vacuolar membrane vesicles was determined.

It is well documented that $Ca^{++}$ enters the plant vacuole via a $Ca^{++}/H^+$ antiporter (K. S. Schumaker, H. Sze, Plant Physiol. 79, 1111-1117 (1985)). Furthermore, the genes encoding the *Arabidopsis thaliana* $Ca^{++}/H^+$ antiporters CAX1 and CAX2 have been isolated and characterized (K. D. Hirschi, R.-G. Zhen, K. W. Cunningham, P. A. Rea, G. R. Fink, Proc. Natl. Acad. Sci. USA 93, 8782-8786 (1996)). FIG. 8 shows that $Ca^{++}$ uptake in the 35SAVP-1 transgenic vacuolar membrane vesicles is 36% higher than it is in vesicles obtained from wild type. Application of the $Ca^{++}$ ionophore A23 lowered the $^{45}Ca^{++}$ counts to background levels demonstrating the tightness of the vesicles (FIG. 8) (K. S. Schumaker, H. Sze, Plant Physiol 79, 1111-1117 (1985)).

While not limited by such theory, a model consistent with the enhanced drought and freeze tolerance of the transgenic plants overexpressing the AVP-1 gene is depicted in FIGS. 9A and 9B. The model depicts how an increase in the number of AVP-1 pumps in the vacuole of transgenic plants can provide more $H^+$ that will permit the secondary transporters to import greater amounts of cations into the lumen of the vacuoles. Higher amounts of cations confer a greater osmotic pressure (See, FIG. 6) that leads to a greater water retention capability endowing plants to withstand low soil water potentials.

Example 10

Double Transgenic Plant with 35SAVP1 and 35S AtNHX1

Overexpression of the pyrophosphate-energized vacuolar membrane proton pump AVP1 likely increases the availability of $H^+$ in the lumen of the vacuole, and the AtNHX1 $Na^+/H^+$ antiporter uses these $H^+$ to sequester $Na^+$ cations into the vacuole. Therefore, higher expression of these transporters likely maximizes the sequestration capability of the vacuole.

To generate transgenic *Arabidopsis* plants that overexpress both genes AVP1 and AtNHX1, T3 35S AVP1 plants may be used as females and T3 35S AtNHX1 plants may be used as males. Female plants may be hand-emasculated and anthers from freshly opened flowers of donor plants are harvested. With these anthers the emasculated plants may be pollinated by touching the anthers onto the stigmas. The pollinated flowers may be labeled and any remaining opened or unopened flowers from the same female plant removed to avoid any confusion at harvest. The harvested seeds should be sterilized using a 50% sodium hypochloride solution and mixed vigorously for 5 minutes and rinsed with water thoroughly. The sterilized seeds may be stored in soft agar over night at 4° C. Then they may be sprinkled onto solidified kanamycin-hygromycin selective medium. The 35S AVP1 construct has the neomycin phosphotransferase II gene that confers kanamycin tolerance in plants while the 35S AtNHX1 construct has a modified hygromycin B phosphotransferase that confers hygromycin tolerance in plants. The resistant seedlings may be transplanted into soil and to the hydroponic media to be tested for their salt-tolerant phenotype.

A transgenic *Arabidopsis thaliana* plant to overexpress the *A. thaliana* gain-of-function mutant gene AVP1-D (Zhen, et al., *J. Biol. Chem.*, 272:22340-22348 (1997)) may be engineered using the same double tandem enhancer of the 35A promoter described above (Topfer, R., et al., *Nucl. Acid Res.*, 15:5890 (1997)). Plants overexpressing the gain of function mutant gene will likely show an enhanced phenotype. These plants may be characterized in parallel with the 35SAVP1, 35S AtNHX singles and doubles transgenics. The *A. thaliana* gain-of-function mutant gene AVP1-D may be subcloned into plasmid pRT103 carrying the 35S promoter and the polyadenylation signal of CaMV (Topfer, R., et al., *Nucl. Acid Res.*, 15:5890 (1997)). A HindIII fragment containing the chimeric 35SAVP-D gene may be subcloned into pBIBhyg (Becker, D., *Nucl. Acid Res.*, 18:203 (1990)). The resulting T-DNA vector may be transformed into *Agrobacterium tumefaciens* strain GV3101 via electroporation, and may be used for subsequent vacuum infiltration of *Arabidopsis thaliana* ecotype Columbia (Bechtold, N., et al., C. R. *Jeances Acad. Sci. Ser. III Sci. Vie*, 316:1194-1199 (1993)). Integration may be confirmed on Southern blots of T3 plants and expression monitored on Northern blots of positive T3 plants.

Example 11

Comparative Transport Study with Vacuoles from the Roots of Wild-Type and 35S AVP1 Transgenic Plants A study may be undertaken to determine if the vacuoles of 35S AVP1 transgenic plants show a higher proton transport activity dependent on pyrophosphate. These determinations may be done with root and shoot tissues separately from plants grown hydroponically. The transgene could show a tissue-specific regulation despite the 35S promoter.

In order to compare the PPI-dependent $H^+$ translocation activities of wild-type and 35S AVP1 transgenic plants sealed tonoplast-enriched vesicles from roots and leaves of the above plants may be prepared. The homogenization and differential centrifugation procedure described by Rea and Turner (Rea, P. A., et al., Tonoplast Adenosine Triphosphate and Inorganic Pyrophosphatase. In: *Meth. Plant Biochem.*, pp. 385-405, Academic Press Limited, London (1990)) may be followed. $H^+$ translocation may be assayed fluorimetrically using acridine orange (2.5 µM) as transmembrane pH difference indicator in assay media containing vacuole membrane-enriched vesicles as described by Rea and coworkers (Zhen, R. G., et al., *J. Biol. Chem.*, 272:22340-22348 (1997)). The assay media contains 300-µM Tris-PPi, 50 mK KCl, 2.5 µM acridine orange, 5 mM Tris-Mes (pH 8.0). Intravesicular acidification may be triggered with the addition of 1.3 mM MgSO4 and terminated with the addition of the protonophore FCCP at 2.5 µM. Fluorescence may be measured at excitation emission wavelengths of 495 and 540 nM, respectively, at a slit width of 5 nM (Zhen, R. G., et al., *J. Biol. Chem.*, 269: 23342-23350 (1994)). A further test to support that the $H^+$ translocation is AVP1 driven may be the addition of the specific inhibitor aminomethylenediphosphonate (Zhen, R. G., et al., *Plant Physiol.*, 104:153-159 (1994)).

Example 12

Determination of the $Na^+/K^+$ Ratios in Leaves and Stems of the Transgenic Plants Toxic concentrations of NaCl build up first in the fully expanded leaves where NaCl is compartmentalized in the vacuoles. Exposure to NaCl can disrupt or reduce $K^+$ uptake leading to K+ deficiency and growth inhibition (Wu, S. J., et al., *Plant Cell,* 8:617-627 (1996). A cytosolic consequence of reduced K+ content and high Na+ is the inhibition of important enzymes. An example of such enzymes is the 3'(2'),5'-bisphosphate nucleotidase of yeast whose activity is more sensitive to Na+ when K+ content is low (Murguia, J. R., et al., *Science,* 267:232-234 (1995).

Measurements may be taken to demonstrate that the transgenic plants described herein have an increased vacuolar capacity to sequester Na+ in their leaves cells or elsewhere. To determine the Na+/K+ ratios in leaves and stem S wild-type and 35S AVP1/35S AtNHX1 double and single transgenics in hydroponic conditions (Gibeaut, D. M., et al., *Plant Physiol.,* 317-319 (1997) may be grown. NaCl may be added to the growth media in a stepwise fashion starting with 50 mM up to 250 mM (Apse, M., et al., *Science,* 285:1256-1258 (1999). At every point the rosette and the stems of the treated plants may be collected and their weight determined. The samples should be dried out in an oven at 80° C. and their dry weight determined. The dry samples may be boiled in a determined volume of water and their Na+ and K+ contents determined via atomic absorption spectrophotometry (Apse, M., et al., *Science,* 285:1256-1258 (1999); Gaxiola, R., et. al., *Embo J.,* 11:3157-2164 (1992)).

Example 13

Determination of Whether 35S AVP1 Transgenic Plants are Larger Because their Cells are Larger or Because they have More Cells, or Both The shoot meristems labeling index may be compared with one of the wild-type plants. Morphological and anatomical observations measuring and counting cells of leaves, roots and stems may be performed. To determine if 35S AVP1 transgenic plants are larger because they have more cells, their shoot meristems labeling index may be compared with the one of wild-type plants.

To measure the DNA synthesis or cell proliferation 5-Bromo-2'-deoxy-uridine (BrdU) that can be incorporated into DNA in place of thymidine may be used., Cells that have incorporated BrdU into DNA may be detected using a monoclonal antibody against BrdU monoclonal antibody and an anti-mouse Ig-alkaline phosphatase as a second antibody. The bound anti-BrdU monoclonal antibody may be visualized by light microscopy and the ratio between DAPI stained and BrdU positives established. The protocol is a modification of the one published by Chiatante and coworkers (Levi, M., et al., *Physiol. Plant.* 71:68-72 (1987)) and the BrdU labeling and detection kit II from Boehringer Mannheim. The plants may be exposed for different times to the BrdU labeling medium and then fixation, paraffin embedding and sectioning may be performed as described by Meyerowitz and coworkers (Drews, G., et al., *Plant Mol. Biol. Rep.,* 5:242-250 (1988)).

For observation of leaf tissue, fresh tissues may be embedded in 5% agarose and slice them with a microslicer. For primary root observation, seedlings may be fixed for 4 hr in 50% ethanol, 5% acetic acid, and 3.7% formaldehyde at room temperature, dehydrated in graded ethanol series, permeate them with xylene, and infiltrate them with paraffin. Eight-micrometer sections may be stained with 0.05% toluidine blue and cells may be counted under a microscope. As an alternative for the visualization and determination of cell size the method described by Greenberg and coworkers (Rate, et al., *The Plant Cell,* 11:1695 1708 (1999)) may be followed.

Results

Figure 10:
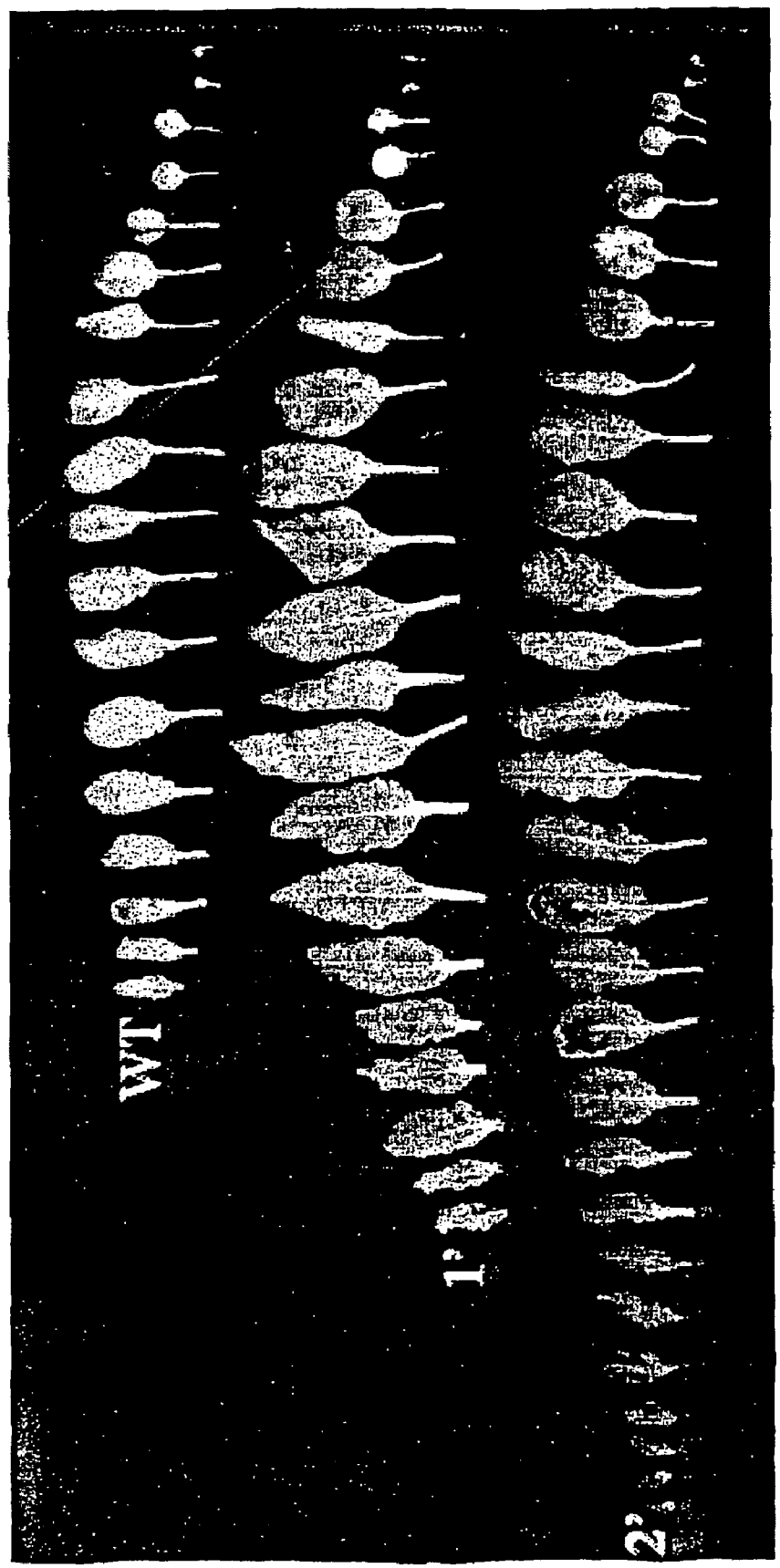
FIG. 10 is an overhead view of the leaf foliage of wild type versus transgenic (1' and 2') AVP-1 overexpressing Arabidopsis plants with leaves positioned with respect to one another according to size (X axis).

Microscopic studies indicate that the cells of the transgenic *Arabidopsis* plants are not larger, but that the number of cells is greater in the transgenics versus wild-type. Macroscopically it was seen that in the AVP-1 line-2' an average of eight more leaves in the rosette was noted over wild-type. F1 plants originated by crossing transgenic lines 1' and 2' displayed rosettes with larger leaves and increased amount of leaves than wild-type plants. FIG. 10 depicts the foliage of wild type and transgenic (1' and 2') *Arabidopsis* plants overexpressing AVP-1 grown at 20° C. under all white fluorescent light in 16 hours light/8 hours dark period cycle. Leaves depicted were carefully sectored with a scalpel when plants initiated to bolt and then ordered by size for comparison purposes. While having larger and more leaves than the wild-type plants, the transgenics, were not seen to have larger cell sizes. Such data is consistent with the hypothesis that the meristem is more active in transgenic AVP-1 overexpressers.

Dry weight of the transgenic *Arabidopsis* plants grown hydroponically, as compared to similarly grown wild-type plants, further indicates that cell mass increases irrespective any increased water uptake by the plant. An increase in dry mass weight was seen in both the root, rosette and stem structures as indicated in Table 1 below where values represent the mean values of six plants.

TABLE 1

| | Dry Weight of *Arabidopsis* Plant Parts Grown Hydroponically WILD-TYPE | | |
|---|---|---|---|
| PLANT PART | WILD TYPE (WT) | 1' TRANSGENIC | 2' TRANSGENIC |
| Roots | −.03 g | 0.05 g | 0.14 g |
| Rosette | 0.10 g | 0.20 g | 0.60 g |
| Stems | 0.40 g | 0.50 g | 0.80 g |

Example 14

Effect of Overexpression of AVP-1 on Hormonal Activity

Increased meristematic activity and/or shoot organogenesis may be produced by increasing hormone availability together with AVP-1 overexpression.

Figure 11:
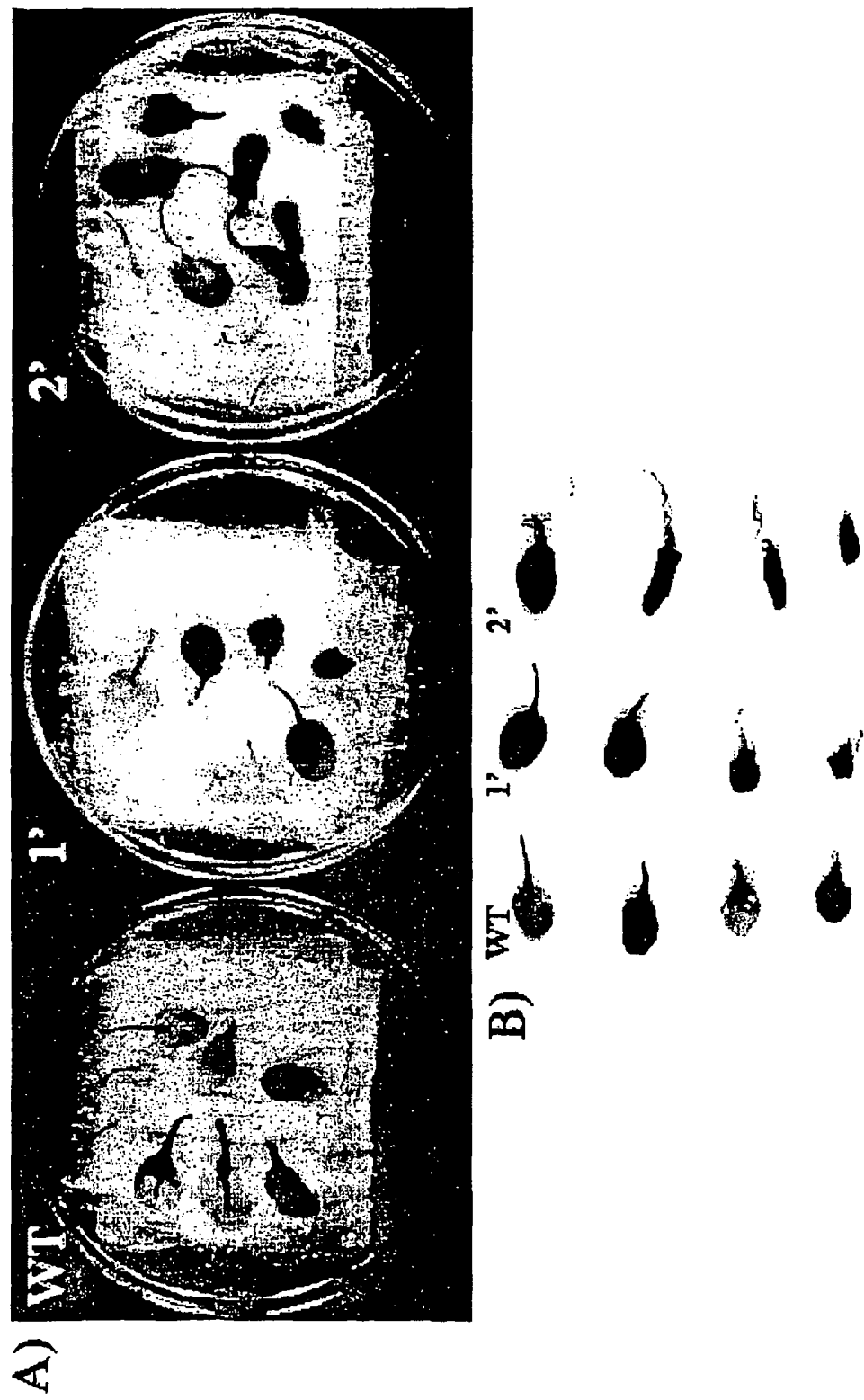
FIGS. 11A and 11B are overhead views of watered (distilled water) leaves from wild type and transgenic (1' and 2') Arabidopsis plants overexpressing AVP-1 demonstrating growth of root structures.

The effect of overexpression of AVP-1 on hormone activity was adjudged placing true leaves from wild type (WT) and transgenic (1', 2') *Arabidopsis* plants overexpressing AVP-1 by careful sectoring with a scalpel. Leaves were placed on 5 layers of filter paper saturated with distilled water in Petri dishes. The Petri dishes, were incubated at 20° C. under cool white fluorescent light in a 16 h light/8 h darkcycles. As seen in FIGS. 11A (view of leaves on the petri dishes) and 11B (view of leaves from petri dishes of FIG. 11A positioned so as to more clearly set depict root structure developing form the leaves), leaves from transgenic plants remain greener and had an enhanced rooting capability. An enhanced rooting capability suggests increased auxin content and delayed senescence consistent with increased cytokinin levels.

Example 15

Effect of Overexpression of AVP-1 on Callus Induction in Petunia Explants Method Petunia explants were incubated on MS medium which consists of MS salts (Gibco BRL), 1 mg/L nicotinic acid, 1 mg/L pyrodoxin HCl, 1 mg/L thiamine, 100 mg/L myo-inositol, 3% sucrose, 1 mg/L 2,4-D(2,4-dichlorophenoxyacetic acid) and 0.5 mg/L 6-BA (6-benzylaminopurine). The medium was solidified with 0.7% agar and was adjusted to pH 5.8 before autoclave. The culture was incubated at 25° C. in the dark in a growth chamber.

Results

Figure 15:
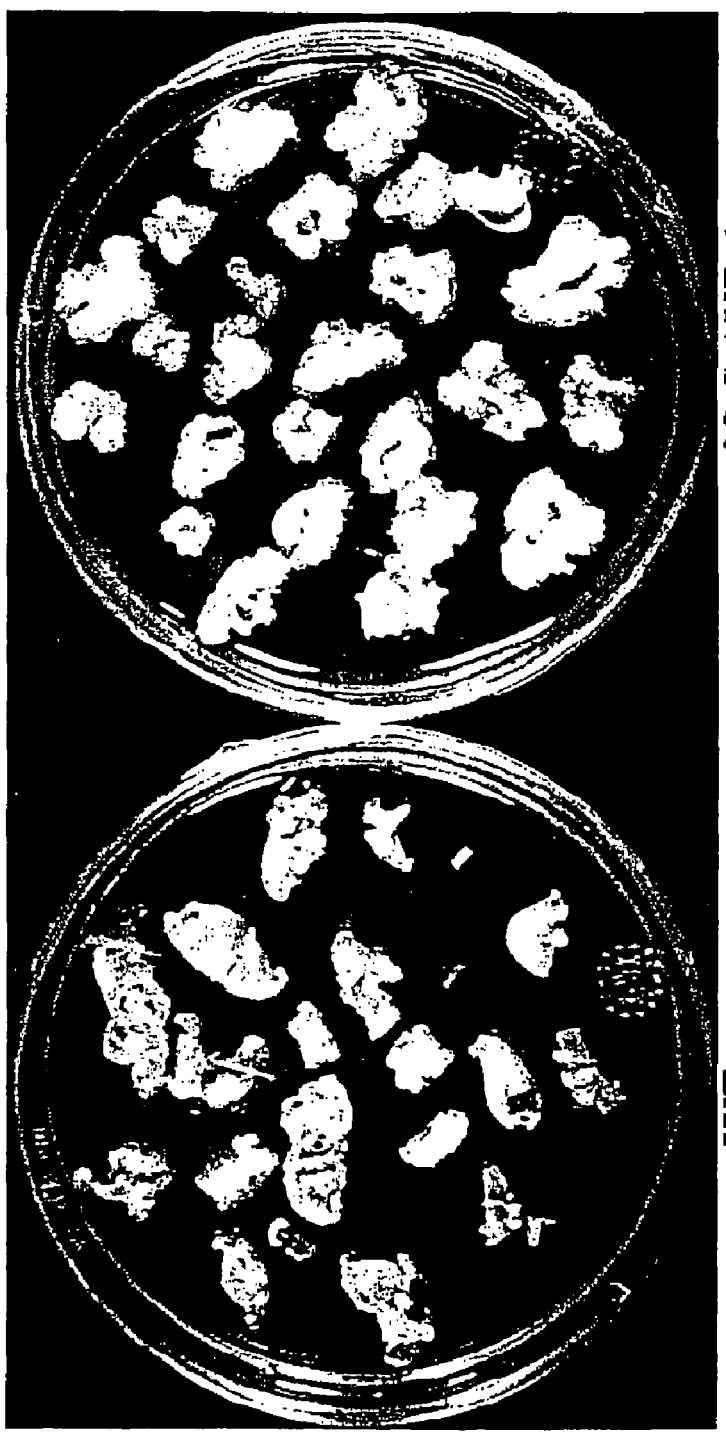
FIG. 15 is an overhead view of petunia explants incubated on MS medium showing callus induction from the explants after six weeks of incubation.

Transgenic petunia explants (35-S AVP-1) demonstrated significantly enhanced callus induction at 6 weeks of incubation as demonstrated in FIG. 15.

Example 16

Effect of Overexpression of AVP-1 on Shoot Regeneration from Leave Segments

Leave segments grown in appropriate medium are known to be capable of generating shoot growth. A study was undertaken to determine the effect of overexpression of 35-S AVP-1 on shoot regeneration in Petunia leaves.

Segments of leaves from regenerated transformed (35-S AVP-1) and control Petunia were used as explants for shoot regeneration. The leaves were cut with a sharp surgical blade into about 1 cm wide pieces. The explants were cultured in MS medium which included MS salts (Gibco), B5 vitamins (1 mg/L nicotinic acid, 1 mg/L pyrodoxin HCl, 1 mg/L-thiamine and 100 mg/L myo-inositol), 3% sucrose, 2 mg/L 6-benzylaminopurine and 0.01 mg/L napthaleneacitic acid, 0.7% agar, pH 5.8. The cultured segments were incubated at 25° C. under cool white fluorescent light in a 16 h light/8 h dark period cycle.

Figure 12:
FIG. 12 is an overhead view of shoot regeneration in representative wild type petunia leave cuttings (WT) versus representative transgenic petunia plant leave cuttings overexpressing AVP-1 (35-S AVP-1).

As shown in FIG. 12, petunia leaves transformed with the AVP-1 gene (35-S AVP-1 petri dish) under a constitutive promoter show an enhanced shoot regeneration capability over wild-type petunia leaf segment (WT) similar to results with transgenic Arabidopsis plants. These results are consistent with the idea that overexpression of this vacuolar proton pump will improve the shoot regeneration capacity of any plant.

A blast search using AVP-1 ORF as a probe showed this gene is highly conserved (rice=86% identities; tobacco=89% identities; barley=86% identities; Vitis vinifera (grapes)=82% identities, Hordeun vulgare (barley)=86% identities and Zea mays (corn)=90% identities). The latter indicates that overexpression of the AVP-1 gene would similarly cause such effects in other plant types.

Example 17

Effect of Overexpression of AVP-1 on Shoot and Root Regeneration from Arabidopsis Cotyledons With appropriate medium, it is known that shoots and roots may be regenerated from cotyledons. Shoot and root regeneration from cotyledons was adjudged for wild-type (WT) and AVP-1 transgenic Arabidopsis (1' and 2').

Five (5) day old cotyledons were used as explants for regeneration. Explants were incubated on shoot induction medium (SIM) at 20° C. under 16 h light/8 h dark period. The SIM contained MS salts (Gibco), B5 vitamins including 1 mg/L nicotinic acid, 1 mg/L pyrodoxin HCl, 1 mg 1-thiamine, and 100 mg/L myoinositol, 3% sucrose, 1 mg/L 6-(gama-gama-dimethylallylamino)purine riboside (2-iP) and 0.1 mg/L naphtaleneacitic acid and solidified with 0.7% agar. The pH of the medium was adjusted to 5.8. 2-iP was filter-sterilized and added to the medium after autoclave.

Figure 13:
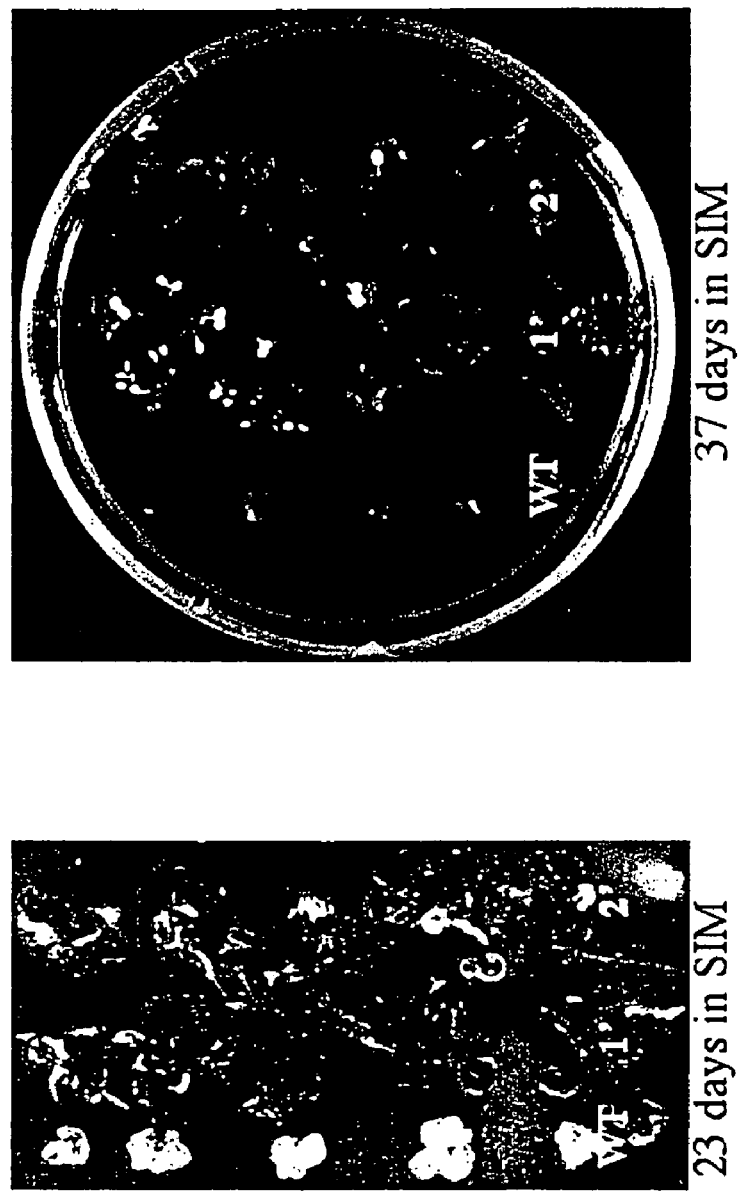
FIG. 13 is an overhead view of shoot regeneration from 5-day old cotyledons placed in SIM induction medium obtained from wild type (WT) and AVP-1 overexpressing (1' and 2') Arabidopsis plants.
Figure 14:
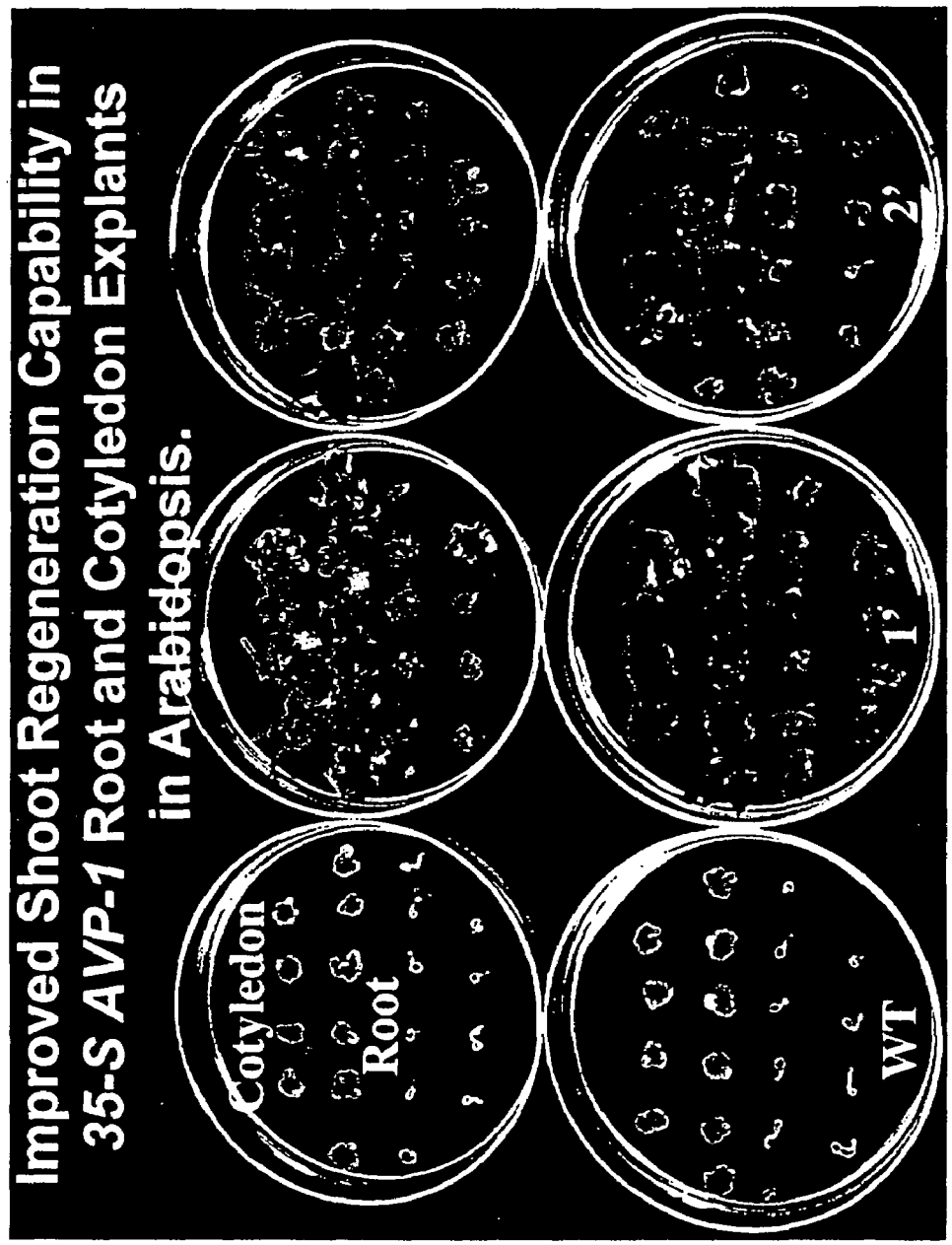
FIG. 14 is an overhead view of shoot regeneration from root and cotyledon explants from wild-type (WT) and AVP-1 overexpressing (1' and 2') Arabidopsis plants, cultured in the SIM medium of FIG. 13.

As is evidenced in the pictures of FIGS. 13A and 13B, explants from transgenic plants (1' and 2') regenerate shoots and roots at a higher frequency and earlier than wild type (WT), consistent with a higher meristematic competence. The evidence of difference between the transformed and wild-type cotyledons was dramatically evidenced at day 23 (FIG. 13A) and more so 37 days into culturing (FIG. 13B).

Example 18

Effect of Overexpression of AVP-1 on Shoot Regeneration from Root and Cotyledon Explants in Arabidopsis Plants Root and cotyledon (5 days old) explants from wild-type (WT) and transgenic (1' and 2') AVP-1 overexpressing Arabidopsis plants were placed in the shoot induction medium as described in Example. 16. As evidenced in FIG. 6, explants from the transgenic plants (1' and 2') generated new structure earlier than wild type consistent with a higher meristematic compentence.

Example 19

Isolation of Mutants in the Transporters

Genetic approaches are very powerful in analyzing complex biological traits (Serrano, R., Crit. Rev. Plant Sci., 13:121-138 (1994)) Reverse genetics is a very important new tool for plant biologists. The generation of a good collection of tagged knockouts by Sussman and coworkers (Krysan, P., et al., Proc. Natl. Acad. Sci. USA, 93:8145-8150 (1996)) has open a very important avenue for the analysis of gene disruptions in Arabidopsis.

The Arabidopsis Knock-out Facility of the University of Wisconsin Madison (world wide web at biotech.wisc.edu/NewServicesAndResearch/Arabidopsis) may be used to search among the 60,480 Arabidopsis (ecotype WS) lines that have been transformed with the T-DNA vector pD991 for the presence of T-DNA inserts within AtCLC-c, AtCLC-d, AVP1, AtNHX1 and their homologues. The phenotypes of the above knock-outs will shed light towards the understanding of the physiological roles of these transporters in normal and stress conditions. An initial characterization of the knockout plants includes testing for their salt tolerance and their $Na^+/K^+$ ratios. The generation of double knock-outs via crosses help to further understand the interaction among the transporters as well as the crosses with the 35S AVP1 and the 35S ATNHX1 transgenic plants.

To search for Arabidopsis knock-out PCR primers may be designed following the guidelines detailed in the University of Wisconsin web site. Tested primers may be sent to UW-Madison, where 62 PCR reactions that are sent to us for Southern blot analysis may be performed. Positive PCR products are sequenced. If the sequence reveals that there is a T-DNA inserted within the gene the gene specific primers are sent for another set of PCR reactions in order to determine which of the 9 possible pools of 225 contains the knockout. After identifying the pool of interest, 25 tubes of seeds are screened for the individual plant carrying the T-DNA knock-out.

Example 20

Cation Detoxification in Plant Cells

The studies described herein together with other evidence strongly indicate that yeast and plants share pathways and signals for the trafficking of vesicles from Golgi network to the vacuole (Gaxiola, R., et al., *Proc. Natl. Acad. Sci. USA*, 96:1480-1485 (1999); Marty, F., "The Biogenesis of Vacuoles: Insights from Microscopy. In: *The Plant Vacuole*, 1-42, Leigh, R. A. and Sanders, D., Academic Press, San Diego (1997); Bassham, D. C., et al., *Plant Physiol*, 117:407-415 (1998)).

Without wishing to be bound by theory, it is believe likely by the present inventor that in both systems a pre-vacuolar compartment is a dynamic entity that detoxifies the cytoplasm from toxic cations and delivers its cargo either to the vacuole, or directly to the cell exterior. Both the gef1 chloride channel and Nhx1 $Na^+/H^+$ exchanger have been localized to the yeast pre-vacuolar compartment (Gaxiola, R. A., et al., *Proc. Natl. Acad. Sci. USA*, 96:1480-1485 (1999)). The behavior of the gef1-GFP chimera in yeast cells in vivo have been monitored indicating that its localization varies depending the environmental conditions. Furthermore, it has been shown that two of the four *A. thaliana* CLC chloride channel genes CLC-c and -d are capable of suppressing gef1 mutant phenotypes implying a similar localization (Gaxiola, R. A., et al., *Proc. Natl. Acad. Sci. USA*, 95:4046-4050 (1998)).

In order to understand how and where this cation detoxification takes place in plant cells the intracellular localization of GFP chimeras of AVP1, AtNHX1 and AtCLC-c and -d (Hong, B., et al., *Plant Physiol*, 119:1165-1175 (1999)) may be monitored in vivo. Confocal microscopy may be also used to address co-localization of the different transporters. For this purpose HA-tagged versions or antibodies of the transporters under study are required (Guiltinan, M. J., et al., *Meth. Cell Biol.*, 49:143-151 (1995); Jauh, G.-Y., et al., Plant Cell, 11:1867-1882 (1999); Mullen, R. T., et al., Plant. J., 12:313-322 (1997)).

For the constructions of the GFP-chimeras the soluble versions GFP with improved fluorescence in *A. thaliana* reported by Davis and Viestra (Davies, S. J., Viestra, R. D., "Soluble derivatives of green fluorescent protein (GFP) for use in *Arabidopsis, thaliana*, http://brindabella.mrc-lmb.cam.ac.uk/IndexGFP.html (1998)). may be used. Two types of GFP-chimeras may be made, namely a set under the regulation of the native promoter and another set under the regulation of the 35S promoter. The resulting T-DNA vectors containing the GFP-chimeras are transformed into *Agrobacterium tumefaciens* strain GV3101 via electroporation, and used for subsequent vacuum infiltration of *Arabidopsis thaliana* ecotype Columbia (Bechtold, N., et al., C. R. Jeances Acad. Sci. Ser. III Sci. Vie, 316:1194-1199 (1993)).

For the hemagglutinin (HA) epitope tagging a PCR strategy designed for yeast but modified to tag plant genes expressed in yeast vectors may be used. Futcher and coworkers designed vectors containing the URA3 yeast gene flanked by direct repeats of epitope tags (HA) (Schneider, B. L., et al, *Yeast*, 11:1265-1274 (1995)). Via PCR the tag-URA3-tag cassette may be amplified such that the resulting PCR fragment possess homology at each end to the gene of interest., In vivo recombination in yeast can be then used to direct the integration of the PCR-chimera to the plasmid carrying the plant ORF of interest, transformants are selected by the $URA^+$ phenotype. The URA3 gene can be "popped out" when positive transformants are grown in the presence of 5-fluoro-orotic acid. The vector carrying the plant gene has a selection marker different than the URA3 gene.

In conclusion, the manipulation of vacuolar V-PPases in economically important crops could provide an important avenue for crop improvement. Drought and freeze tolerant cultivars could provide new agricultural approaches in areas lost due to drought or minimal rainfall, as well as to provide farmers with protection from unanticipated frosts (freezing rain etc.). Such crops may also be able to be raised on soils considered too saline for wild type crops.

While the invention has been described with respect to preferred embodiments, those skilled in the art will readily appreciate that various changes and/or modifications can be made to the invention without departing from the spirit or scope of the invention as defined by the appended claims. All references cited in this specification are herein incorporated by reference to the same extent as if each individual reference was specifically and individually indicated to be incorporated by reference.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A transgenic plant overexpressing at least one vacuolar pyrophosphatase compared to a wild-type plant of the same plant species, wherein said transgenic plant comprises transgenic plant cells containing an exogenous nucleic acid that causes overexpression of the vacuolar pyrophosphatase in said transgenic plant cells, and wherein said transgenic plant possesses at least one phenotype selected from the group consisting of: increased salt tolerance compared to said wild-type plant, increased drought tolerance compared to said wild-type plant, increased freezing tolerance compared to said wild-type plant, increased meristematic cell division compared to said wild-type plant, increased biomass compared to said wild-type plant, altered root morphology compared to said wild-type plant, improved shoot regeneration compared to said wild-type plant, and enhanced water retention capability compared to said wild-type plant.

2. A method for making a transgenic plant having at least one enhanced phenotypic trait compared to a wild-type plant of the same plant species, said method comprising:
    a) introducing exogenous nucleic acid into cells from a plant to produce transformed plant cells, said exogenous nucleic acid resulting in overexpression of a vacuolar pyrophosphatase in the transformed plant cells; and,
    b) generating a transgenic plant from the transformed plant cells, wherein said transgenic plant possesses at least one phenotype selected from the group consisting of: increased salt tolerance compared to said wild-type plant, increased drought tolerance compared to said wild-type plant, increased freezing tolerance compared to said wild-type plant, increased meristematic cell division compared to said wild-type plant, increased biomass compared to said wild-type plant, altered root morphology compared to said wild-type plant, improved shoot regeneration compared to said wild-type plant, and enhanced water retention capability compared to said wild-type plant.

3. The transgenic plant of claim 1, wherein said vacuolar pyrophosphatase is *Arabidopsis thaliana* vacuolar pyrophosphatase 1 (AVP1) or a homolog thereof, and wherein said homolog has vacuolar pyrophosphatase activity.

4. The transgenic plant of claim 3, wherein said exogenous nucleic acid comprises a nucleic acid encoding AVP1 or a homolog thereof operably linked to a promoter.

5. The transgenic plant of claim 4, wherein said promoter comprises a double tandem enhancer of the 35S promoter.

6. The transgenic plant of claim 1, wherein said transgenic plant is tomato, corn, tobacco, rice, sorghum, cucumber, lettuce, turf grass, legume or an ornamental.

7. A seed produced by the transgenic plant of claim 1, wherein said seed comprises the exogenous nucleic acid which causes overexpression of the vacuolar pyrophosphatase.

8. A transgenic progeny of the transgenic plant of claim 1, wherein said progeny comprises transgenic plant cells containing the exogenous nucleic acid which causes overexpression of the vacuolar pyrophosphatase.

9. A transgenic plant cell comprising an exogenous nucleic acid that causes overexpression of at least one vacuolar pyrophosphatase compared to a wild-type plant cell of the same plant species, wherein said transgenic plant cell possesses at least one phenotype selected from the group consisting of: increased salt tolerance compared to said wild-type plant cell, increased drought tolerance compared to said wild-type plant cell, increased freezing tolerance compared to said wild-type plant cell, and enhanced water retention capability compared to said wild-type plant cell.

10. The transgenic plant cell of claim 9, wherein said vacuolar pyrophosphatase is *Arabidopsis thaliana* vacuolar pyrophosphatase 1 (AVP1) or a homolog thereof, and wherein said homolog has vacuolar pyrophosphatase activity.

11. The transgenic plant cell of claim 10, wherein said exogenous nucleic acid comprises a nucleic acid encoding AVP1 or a homolog thereof operably linked to a promoter.

12. The transgenic plant cell of claim 9, wherein said transgenic plant cell is a root cell, stem cell or leaf cell.

13. The transgenic plant cell of claim 12, wherein said transgenic plant cell is derived from tomato, corn, tobacco, rice, sorghum, cucumber, lettuce, turf grass, legume or an ornamental plant.

* * * * *

SEQUENCE LISTING

<160> NUMBER OF SEQ ID NOS: 2

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      template oligonucleotide

<400> SEQUENCE: 1
ggcccgggat ggattctcta gtgtcgaaac tgccttcg                    38

<210> SEQ ID NO 2
<211> LENGTH: 770
<212> TYPE: PRT
<213> ORGANISM: Arabidopsis thaliana

<400> SEQUENCE: 2

```
Met Val Ala Pro Ala Leu Leu Pro Glu Leu Trp Thr Glu Ile Leu Val
 1               5                  10                  15

Pro Ile Cys Ala Val Ile Gly Ile Ala Phe Ser Leu Phe Gln Trp Tyr
            20                  25                  30

Val Val Ser Arg Val Lys Leu Thr Ser Asp Leu Gly Ala Ser Ser Ser
        35                  40                  45

Gly Gly Ala Asn Asn Gly Lys Asn Gly Tyr Gly Asp Tyr Leu Ile Glu
    50                  55                  60

Glu Glu Glu Gly Val Asn Asp Gln Ser Val Ala Lys Cys Ala Glu
65                  70                  75                  80

Ile Gln Thr Ala Ile Ser Glu Gly Ala Thr Ser Phe Leu Phe Thr Glu
                85                  90                  95

Tyr Lys Tyr Val Gly Val Phe Met Ile Phe Ala Ala Val Ile Phe
            100                 105                 110

Val Phe Leu Gly Ser Val Glu Gly Phe Ser Thr Asp Asn Lys Pro Cys
        115                 120                 125

Thr Tyr Asp Thr Thr Arg Thr Cys Lys Pro Ala Leu Ala Thr Ala Ala
    130                 135                 140

Phe Ser Thr Ile Ala Phe Val Leu Gly Ala Val Thr Ser Val Leu Ser
145                 150                 155                 160

Gly Phe Leu Gly Met Lys Ile Ala Thr Tyr Ala Asn Ala Arg Thr Thr
                165                 170                 175

Leu Glu Ala Arg Lys Gly Val Gly Lys Ala Phe Ile Val Ala Phe Arg
            180                 185                 190

Ser Gly Ala Val Met Gly Phe Leu Ala Ala Ser Gly Leu Leu Val
        195                 200                 205

Leu Tyr Ile Thr Ile Asn Val Phe Lys Ile Tyr Tyr Gly Asp Asp Trp
    210                 215                 220

Glu Gly Leu Phe Glu Ala Ile Thr Gly Tyr Gly Leu Gly Gly Ser Ser
225                 230                 235                 240

Met Ala Leu Phe Gly Arg Val Gly Gly Gly Ile Tyr Thr Lys Ala Ala
                245                 250                 255

Asp Val Gly Ala Asp Leu Val Gly Lys Ile Glu Arg Asn Ile Pro Glu
            260                 265                 270

Asp Asp Pro Arg Asn Pro Ala Val Ile Ala Asp Asn Val Gly Asp Asn
        275                 280                 285

Val Gly Asp Ile Ala Gly Met Gly Ser Asp Leu Phe Gly Ser Tyr Ala
    290                 295                 300

Glu Ala Ser Cys Ala Ala Leu Val Val Ala Ser Ile Ser Ser Phe Gly
305                 310                 315                 320

Ile Asn His Asp Phe Thr Ala Met Cys Tyr Pro Leu Leu Ile Ser Ser
                325                 330                 335

Met Gly Ile Leu Val Cys Leu Ile Thr Thr Leu Phe Ala Thr Asp Phe
            340                 345                 350

Phe Glu Ile Lys Leu Val Lys Glu Ile Glu Pro Ala Leu Lys Asn Gln
        355                 360                 365

Leu Ile Ile Ser Thr Val Ile Met Thr Val Gly Ile Ala Ile Val Ser
    370                 375                 380

Trp Val Gly Leu Pro Thr Ser Phe Thr Ile Phe Asn Phe Gly Thr Gln
385                 390                 395                 400
```

```
Lys Val Val Lys Asn Trp Gln Leu Phe Leu Cys Val Cys Val Gly Leu
                405                 410                 415
Trp Ala Gly Leu Ile Ile Gly Phe Val Thr Glu Tyr Tyr Thr Ser Asn
            420                 425                 430
Ala Tyr Ser Pro Val Gln Asp Val Ala Asp Ser Cys Arg Thr Gly Ala
        435                 440                 445
Ala Thr Asn Val Ile Phe Gly Leu Ala Leu Gly Tyr Lys Ser Val Ile
    450                 455                 460
Ile Pro Ile Phe Ala Ile Ala Ile Ser Ile Phe Val Ser Phe Ser Phe
465                 470                 475                 480
Ala Ala Met Tyr Gly Val Ala Val Ala Leu Gly Met Leu Ser Thr
            485                 490                 495
Ile Ala Thr Gly Leu Ala Ile Asp Ala Tyr Gly Pro Ile Ser Asp Asn
            500                 505                 510
Ala Gly Gly Ile Ala Glu Met Ala Gly Met Ser His Arg Ile Arg Glu
            515                 520                 525
Arg Thr Asp Ala Leu Asp Ala Ala Gly Asn Thr Thr Ala Ala Ile Gly
    530                 535                 540
Lys Gly Phe Ala Ile Gly Ser Ala Ala Leu Val Ser Leu Ala Leu Phe
545                 550                 555                 560
Gly Ala Phe Val Ser Arg Ala Gly Ile His Thr Val Asp Val Leu Thr
                565                 570                 575
Pro Lys Val Ile Ile Gly Leu Leu Val Gly Ala Met Leu Pro Tyr Trp
            580                 585                 590
Phe Ser Ala Met Thr Met Lys Ser Val Gly Ser Ala Ala Leu Lys Met
    595                 600                 605
Val Glu Glu Val Arg Arg Gln Phe Asn Thr Ile Pro Gly Leu Met Glu
    610                 615                 620
Gly Thr Ala Lys Pro Asp Tyr Ala Thr Cys Val Lys Ile Ser Thr Asp
625                 630                 635                 640
Ala Ser Ile Lys Glu Met Ile Pro Pro Gly Cys Leu Val Met Leu Thr
                645                 650                 655
Pro Leu Ile Val Gly Phe Phe Gly Val Glu Thr Leu Ser Gly Val
            660                 665                 670
Leu Ala Gly Ser Leu Val Ser Gly Val Gln Ile Ala Ile Ser Ala Ser
        675                 680                 685
Asn Thr Gly Gly Ala Trp Asp Asn Ala Lys Lys Tyr Ile Glu Ala Gly
    690                 695                 700
Val Ser Glu His Ala Lys Ser Leu Gly Pro Lys Gly Ser Glu Pro His
705                 710                 715                 720
Lys Ala Ala Val Ile Gly Asp Thr Ile Gly Asp Pro Leu Lys Asp Thr
                725                 730                 735
Ser Gly Pro Ser Leu Asn Ile Leu Ile Lys Leu Met Ala Val Glu Ser
            740                 745                 750
Leu Val Phe Ala Pro Phe Phe Ala Thr His Gly Gly Ile Leu Phe Lys
        755                 760                 765
Tyr Phe
770
```